(12) United States Patent
Grimm et al.

(10) Patent No.: US 12,094,586 B2
(45) Date of Patent: Sep. 17, 2024

(54) MATERIALS AND METHODS RELATING TO DOSAGE REGIMEN DESIGN

(71) Applicant: Hoffmann-La Roche Inc., Little Falls, NJ (US)

(72) Inventors: Hans Peter Grimm, Basel (CH); Benjamin Ribba, Basel (CH); Volker Teichgräaeber, Bottmingen (CH)

(73) Assignee: HOFFMANN-LA ROCHE INC., Little Falls, NJ (US)

( * ) Notice: Subject to any disclaimer, the term of this patent is extended or adjusted under 35 U.S.C. 154(b) by 1279 days.

(21) Appl. No.: 16/196,883

(22) Filed: Nov. 20, 2018

(65) Prior Publication Data

US 2019/0361018 A1 Nov. 28, 2019

Related U.S. Application Data

(63) Continuation of application No. PCT/EP2017/062302, filed on May 22, 2017.

(30) Foreign Application Priority Data

May 25, 2016 (EP) .................................... 16171263

(51) Int. Cl.
G16H 20/10 (2018.01)
G16H 50/50 (2018.01)

(52) U.S. Cl.
CPC .............. *G16H 20/10* (2018.01); *G16H 50/50* (2018.01)

(58) Field of Classification Search
None
See application file for complete search history.

(56) References Cited

U.S. PATENT DOCUMENTS

| 8,589,175 | B2 | 11/2013 | Glauser et al. |
| 2007/0098685 | A1 | 5/2007 | Brand |
| 2009/0123428 | A1 | 5/2009 | Hall et al. |
| 2009/0306944 | A1* | 12/2009 | Willmann ............. G16C 20/30 703/2 |
| 2012/0104039 | A1 | 5/2012 | Schreier et al. |

FOREIGN PATENT DOCUMENTS

| WO | 2015/085276 A1 | 6/2015 |
| WO | 2016/014530 A1 | 1/2016 |
| WO | 2016/025385 A1 | 2/2016 |

OTHER PUBLICATIONS

Bien, E.; Balcerska, A. Serum Soluble Interleukin 2 Receptor α in Human Cancer of Adults and Children: A Review. Biomarkers 2008, 13 (1), 1-26.*

(Continued)

*Primary Examiner* — Soren Harward
(74) *Attorney, Agent, or Firm* — Yan Qi

(57) ABSTRACT

The present invention provides materials and methods for determining optimal dosage regimens for therapeutic agents. In particular, the invention relates to dosage regimens for therapeutic agents capable of targeting IL-2 receptor, preferably interleukin 2 (IL2)-based therapeutic agents. The methods of the invention allow general dosage regimens to be determined for new IL-2R targeted therapeutic agents but also specifically tailored dosage regimens to be achieved for individuals being treated with IL-2R targeted therapeutic agents.

18 Claims, 10 Drawing Sheets
Specification includes a Sequence Listing.

(56) References Cited

OTHER PUBLICATIONS

Klein, C.; Waldhauer, I.; Nicolini, V.; Dunn, C.; Freimoser-Grundschober, A.; Danny, G.; Boerman, O.; Nayak, T.; Herter, S.; Van Puijenbroek, E.; Ast, O.; Hofer, T.; Hosse, R.; Lang, S.; Neumann, S.; Kettenberger, H.; Neubauer, M.; Gorr, I.; Tuerck, D.; Evers, S.; Gerdes, C.; Levitsky, V.; Bacac, M.; Moessner, E.*

León, K.; García-Martínez, K.; Carmenate, T. Mathematical Models of the Impact of IL2 Modulation Therapies on T Cell Dynamics. Frontiers in Immunology 2013, 4, 439:1-21.*

Mager, D. E. Target-Mediated Drug Disposition and Dynamics. Biochemical Pharmacology 2006, 72 (1), 1-10.*

Thurber, G. M.; Dane Wittrup, K. A Mechanistic Compartmental Model for Total Antibody Uptake in Tumors. Journal of Theoretical Biology 2012, 314, 57-68.*

Dua et al., "A Tutorial on Target-Mediated Drug Disposition (TMDD) Models" Syst. Pharmacol 4:324-327 (2015).

Lindstrom et al., "Nonlinear Mixed Effects Models for Repeated Measures Data" Biometrics 46:673-687 (Sep. 1990).

Lode et al., "Natural Killer Cell-Mediated Eradication of Neuroblastoma Metastases to Bone Marrow by Targeted Interleukin-2 Therapy" Blood 91(5 Suppl 1706-1715) (1998).

Peletier et al., Dynamics of Target-Mediated Drug Disposition A Mathematical Analysis Lecture slides, Systems Pharmacology School ,School of Engineering: 1-27 (2014).

"PROLEUKIN® (aldesleukin) United States Prescribing Information (USPI), pp. 1-19, Jul. 2012".

Schmidt et al., "A modeling analysis of the effects of molecular size and binding affinity on tumor targeting" Mol Cancer Ther 8(10):2861-2871 (2009).

Thurber et al., "A mechanistic compartmental model for total antibody uptake in tumors" J Theor Biol 314:57-68 (2012).

Davidian et al., "Between Dose and Response: Pharmacokinetics, Pharmacodynamics and Statistics" Scope Academy: Between Dose and Response 2008.

Gibiansky et al., "Target-mediated drug disposition model: approximations, identifiability of model parameters and applications to the population pharmacokinetic-pharmacodynamic modeling of biologics" Expert Opinion on Drug Metabolism & Toxicology 5(7):803-812 (2009).

ISR of PCT/EP2017/062302 (Date of mailing Sep. 1, 2017).

Mager et al., "Target-mediated drug disposition and dynamics" Biochemical pharmacology 72(1):1-10 (2006).

* cited by examiner

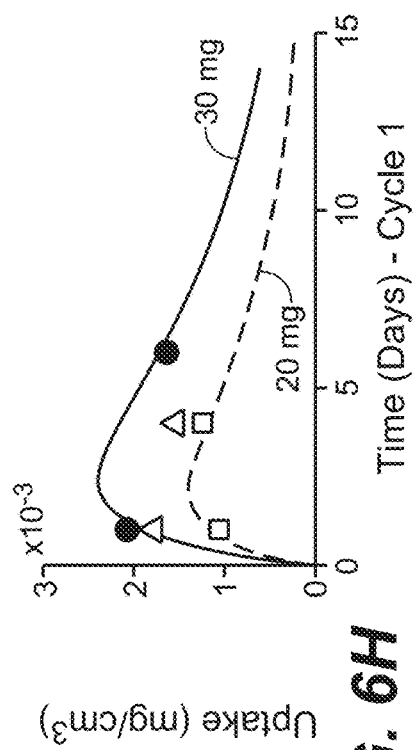
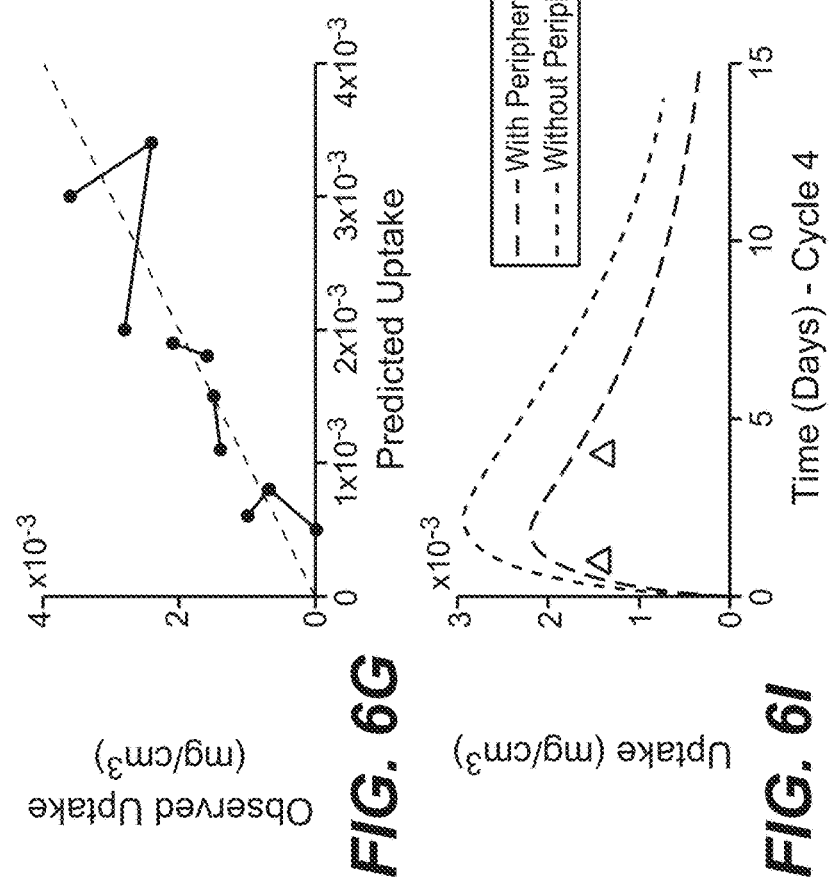

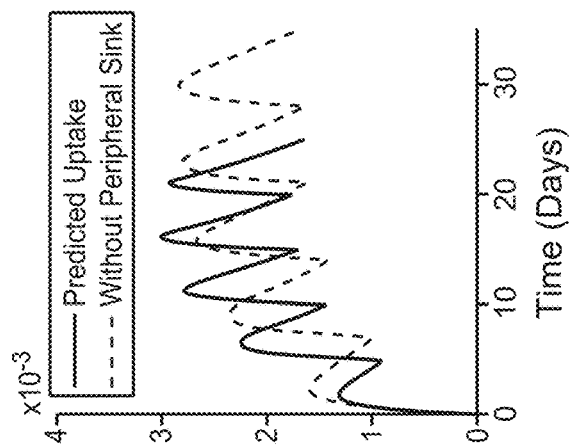
FIG. 8C
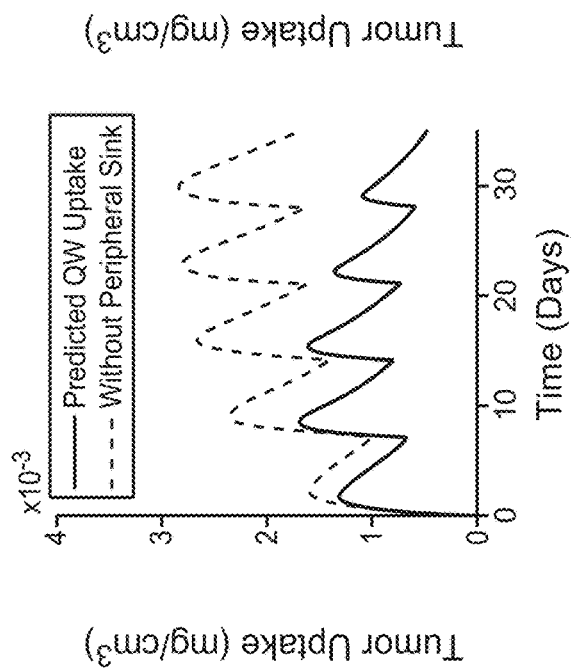
FIG. 8B
FIG. 8A
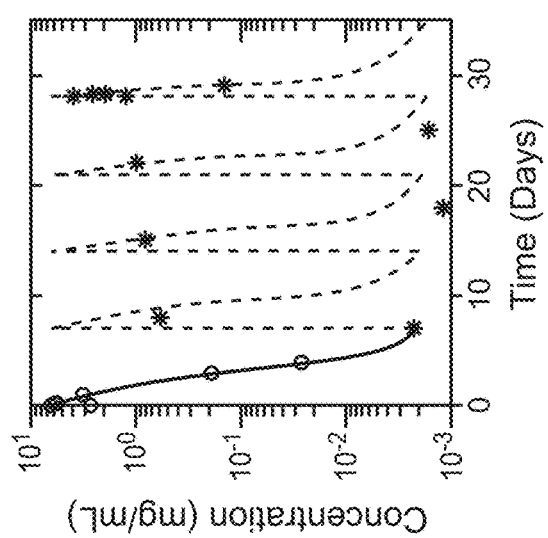

MATERIALS AND METHODS RELATING TO DOSAGE REGIMEN DESIGN

CROSS-REFERENCE TO RELATED APPLICATIONS

This application is a continuation of International Application No. PCT/EP2017/062302, filed on May 22, 2017, which claims priority from European Patent Application No. 16171263.3, filed on May 25, 2016, the contents of which are incorporated herein by reference in their entireties.

SEQUENCE LISTING

The present application contains a Sequence Listing which has been submitted electronically as a text file in ASCII format and is hereby incorporated by reference in its entirety. Said text file, created on Nov. 20, 2018, is named P33663-US_SeqListing.txt and is 32,570 bytes in size.

FIELD OF THE INVENTION

The present invention provides materials and methods for determining optimal dosage regimens for therapeutic agents. In particular, the invention relates to dosage regimens for therapeutic agents capable of targeting IL-2 receptor, preferably interleukin 2 (IL2)-based therapeutic agents. The methods of the invention allow general dosage regimens to be determined for new IL-2R targeted therapeutic agents but also specifically tailored dosage regimens to be achieved for individuals being treated with IL-2R targeted therapeutic agents.

BACKGROUND OF THE INVENTION

Recombinant wild type IL2 (Proleukin) achieves complete remission and long-lasting disease control in 5 to 10% of patients with metastatic melanoma and metastatic renal cell carcinoma. Serum half-life of Proleukin ranges from 13 to 85 minutes and requires a dense treatment schedule with three times a day (q8 h, t.i.d) infusions for up to 5 consecutive days (maximum of 14 doses) given in 2 cycles with a wash-out period of one week in between[1]. High doses of Proleukin cause major systemic toxicities and compromise the anti-tumor immunity via induction of regulatory T cells (T-reg) and activation-induced cell death (AICD) while cytokine concentrations near the tumor are too low for optimal antitumor responses[2].

Two immunoconjugates comprising an IL-2 variant (IL-2v) which binds to IL-2Rβγ but not IL-2Rα, designed to improve the pharmacological and safety profile of IL-2 and to enable local accumulation in tumors, are currently being tested in phase I clinical trials.

Generally drugs are administered in multiple doses to treat chronic diseases. The aim is to maintain a therapeutically effective concentration of the active compound over a period of time in order to provide a therapeutic benefit to the individual being treated. After a single dose of the therapeutic agent, the plasma levels of that compound rise to the effective concentration but after a period of time fall below the minimum effective concentration, which results in a decline of the therapeutic effect. Accordingly, a dosage regimen aims to provide an individual with multiple dosages of the therapeutic agent to maintain plasma levels within the narrow limits of the therapeutic window, e.g. above the minimum effective concentration and yet below the level which may result in a toxic effect for the individual. In summary, the aim of a dosage regimen is to achieve optimal clinical effectiveness for the therapeutic agent without excessive fluctuation and drug accumulation outside the therapeutic window.

There are two main parameters that can be adjusted in order to achieve optimal clinical effectiveness for the active compound, namely (1) size of the dose (i.e. amount of active compound); and (2) the time interval between doses. To calculate a dosage regimen for an active compound many factors are taken into consideration from the pharmacokinetic and pharmacodynamic data obtained during clinical trials.

Many adverse drug reactions or simply a lack of therapeutic effect are the result of individuals being prescribed the incorrect dosage: the "one size fits all" method of drug prescription. There are many variables which will give rise to differing responses to a drug.

These variables range from the more obvious such as age, sex and weight of the individual, but importantly also include genomic and proteomic differences. The elimination half-life of a drug is an important factor in determining dosage regimens as it effects not only drug accumulation (which could be toxic to the individual), but also the clinical effectiveness of the drug.

There is an on-going need to develop techniques which allow optimal dosage regimens to be determined for therapeutic agents and in particular dosage regimens which can be specifically tailored to the individual being treated.

SUMMARY OF THE INVENTION

Pharmacokinetic (PK) and pharmacodynamic (PD) data have been collected from individuals given CEA-targeted IL2v immunoconjugate (cergutuzumab amunaleukin, also referred to herein as CEA IL2v) to treat solid tumors.

Phase I clinical trial data showed nonlinear pharmacokinetics for CEA-IL2v. The inventors believe an explanation for this phenomenon is the occurrence of target-mediated drug disposition (TMDD). TMDD is a process wherein a significant proportion of a drug is bound with high affinity to a pharmacological target, such that this interaction is reflected in the pharmacokinetic properties of the drug[3]. The phase I clinical trial data also showed a reduction of serum concentrations with time following multiple dosing. The inventors believe that this reduction would be caused by IL2v-driven expansion of interleukin-2 receptor-positive (IL-2R+) peripheral cells.

Put more simply, without wishing to be bound by theory, CEA-IL2v binds to the IL2 receptor of the immune cell in blood and this drug-receptor complex is internalised. The internalisation leads to activation of the immune cell and migration to a secondary lymphoid organ (e.g. lymph node). In the lymph node, the immune cells will proliferate and the receptor expression will be upregulated. The new cells will return to the circulation. The increase in the amount of immune cells and the higher receptor expression will lead to a higher capacity to bind and eliminate CEA-IL2v from the circulation. As a result, there is a sharp decrease of immune cells as a result of CEA-IL2v-IL2 receptor binding followed by a rebound above initial cell numbers as a result of proliferation.

As a result of these observations, the inventors have developed an integrated modeling platform to quantify the impact of TMDD with target expansion on tissue (e.g. tumor) uptake of a therapeutic agent. This platform firstly provides an improved process for identifying an optimal dosing regimen for a population of patients in the context of a clinical trial; and secondly, a process for identifying an optimal dosing regimen for a single individual in the context of personalization of treatment care.

In general, the integrated modeling platform described herein may be used to determine the optimal dosing regimen (e.g. size of dose, time interval between doses) to compensate for the reduction of target tissue (e.g. tumor) uptake of a therapeutic agent due to TMDD. However, more particularly, the integrated modeling platform described herein may be used to optimize dose and schedule of the therapeutic agent in order to maximize exposure of the therapeutic agent in the target tissue microenvironment. The determined optimal dosage regimen for the therapeutic agent may be universal, i.e. for a population of individuals being treated with the therapeutic agent, or it may be individual, i.e. a dosage regimen tailored to a particular individual being treated with the therapeutic agent. In summary, the invention provides a tool for determining the required increase in a dose of a IL-2R targeting (e.g. IL2-based) therapeutic agent (whether that is an increase in the amount of the therapeutic agent in a single dose or a change, e.g. reduction, in the time interval between doses) in order to compensate for non-therapeutic target expansion (e.g. expansion of interleukin-2 receptor-positive (IL-2R+) cells) in blood following the initial or previous dose, thereby optimising the amount of therapeutic agent available for therapeutic target tissue uptake (e.g. solid tumor uptake).

In a first aspect there is provided a method for determining an optimal dosing regimen for a therapeutic agent, said process comprising
a) simulating a model, such as a pharmacokinetic (PK) or pharmacokinetic/pharmacodynamic (PKPD) model, using data obtained from one or more individuals at one or more time points following dose administration of the therapeutic agent; wherein the data includes PK data relating to the concentration of unbound therapeutic agent;
wherein the model is:

$$\frac{d[Ab]_{free}}{dt} = -k_{clear} \cdot [Ab]_{free} - (k_{on} \cdot [Ab]_{free} \cdot [IL2R]_{free} - k_{off} \cdot [Complex])$$

$$\frac{d[IL2R]_{free}}{dt} = k_{in} - k_{out} \cdot [IL2R]_{free} -$$

$$(k_{on} \cdot [Ab]_{free} \cdot [IL2R]_{free} - k_{off} \cdot [Complex]) + \eta \cdot k_{int} \cdot [Complex]$$

$$\frac{d[Complex]}{dt} = k_{on} \cdot [Ab]_{free} \cdot [IL2R]_{free} - k_{off} \cdot [Complex] - k_{int} \cdot [Complex]$$

wherein:
$[Ab]_{free}$ is the concentration of unbound therapeutic agent in plasma,
$[IL2R]_{free}$ is the concentration of unbound immune cells expressing IL2 receptor in blood and given by $k_{in}/k_{out}$. or optionally obtained from PD data,
[Complex] is the concentration of complex between the therapeutic agent and immune cells expressing IL-2 receptor (IL2R+ cells),
$k_{clear}$ is a constant rate of elimination of therapeutic agent from plasma and has a value between 0.02 and 0.04 hour$^{-1}$;
$k_{on}$ is an association rate of complex between the therapeutic agent and immune cells expressing IL-2 receptor and has a value between 0.26 and 4.5 µM$^{-1}$ h$^{-1}$;
$k_{off}$ is a dissociation rate of complex between the therapeutic agent and immune cells expressing IL-2 receptor and has a value between 0.0035 and 0.02 h$^{-1}$, $k_{in}$ is a constant influx rate of IL2R+ cells in plasma and has a value between 0.0006 and 0.0144 µM·h$^{-1}$;
$k_{out}$ is a natural decay rate of IL2R+ cells in plasma and has a value between 0.0018 and 0.069 h$^{-1}$,
$k_{int}$ is the internalization rate of the therapeutic agent and has a value between 0.0066 and 0.023 h$^{-1}$; and
η is a constant rate of expansion of IL2R+ cells in plasma as a result of the binding (internalization) of the therapeutic agent and has a value between 1.02 and 3.31;
b) providing an optimal dosage regimen based on the increase in therapeutic agent required to compensate for reduction in unbound therapeutic agent;
wherein the therapeutic agent is a compound which is capable of targeting IL2R.

The optimal dosage regimen is preferably a regimen that when simulated using the model provides the best target tissue (e.g. tumor) uptake as compared to other simulated dosing regimens. The optimal dosage regimen may comprise an increase in the amount of therapeutic agent given in a single dose administration (as compared to a previous dose administration), it may comprise a change (e.g. reduction) in the time interval between doses (as compared to the time interval between previous doses), or it may comprise a combination of both. In some embodiments, the optimal dosage regimen is a combination of an amount of therapeutic agent given per dose administration and a time interval between dose administrations.

In this first aspect, the method allows an optimal dosage regimen to be determined for a cytokine-based therapeutic agent on the basis of PK data, and optionally PD data, collected from several individuals treated with the therapeutic agent. This may provide a "universal" dosage regimen, i.e. a single dosage regimen that may be adopted by the majority of individuals being treated with the therapeutic agent subject to other clinical considerations such as weight, sex, age, general well-being etc. For such a universal dosage regimen it is preferable to collect data from a population of individuals being treated with the therapeutic agent, e.g. IL-2-based therapeutic agent. The population may comprise two or more, three or more, five or more, ten or more, fifteen or more, twenty or more, thirty or more, or fifty or more individuals each being treated with the therapeutic agent.

For this and other aspects of the invention, it is preferable to collect data from several time points following the initial dose (or a previous dose) administration of the therapeutic agent. Suggested sampling time points for both PK and PD data are discussed below in respect of this aspect and other aspects of the invention described herein.

The baseline value of $[IL2R]_{free}$ compartment is—by mathematical construction—given by $k_{in}/k_{out}$. Its evolution is then governed by the model parameters all inferred through the use of the PK observations. In this case, this compartment does not "physically" represent cells but rather a virtual compartment also called latent variable that is in there to correctly describe the PK kinetic. However, PD data relating to unbound immune cells expressing IL2 receptor may be collected and used for parameter $[IL2R]_{free}$ instead of $k_{in}/k_{out}$.

This first aspect of the invention may also be used to optimise a dosage regimen for an individual being treated with the therapeutic agent. The method may comprise a) simulating a model, such as a pharmacokinetic (PK) or pharmacokinetic/pharmacodynamic (PKPD) model, using data obtained from said individual at one or more time points following dose administration of the therapeutic agent; wherein the data includes PK data relating to the amount of unbound therapeutic agent, wherein the model is:

$$\frac{d[Ab]_{free}}{dt} = -k_{clear} \cdot [Ab]_{free} - (k_{on} \cdot [Ab]_{free} \cdot [IL2R]_{free} - k_{off} \cdot [Complex])$$

$$\frac{d[IL2R]_{free}}{dt} = k_{in} - k_{out} \cdot [IL2R]_{free} -$$

$$(k_{on} \cdot [Ab]_{free} \cdot [IL2R]_{free} - k_{off} \cdot [Complex]) + \eta \cdot k_{int} \cdot [Complex]$$

$$\frac{d[Complex]}{dt} = k_{on} \cdot [Ab]_{free} \cdot [IL2R]_{free} - k_{off} \cdot [Complex] - k_{int} \cdot [Complex]$$

wherein:
- $[Ab]_{free}$ is the concentration of unbound therapeutic agent in plasma,
- $[IL2R]_{free}$ is the concentration of unbound immune cells expressing IL2 receptor in blood and given by $k_{in}/k_{out}$ or optionally obtained from PD data,
- [Complex] is the concentration of complex between the therapeutic agent and immune cells expressing IL-2 receptor (IL2R+ cells),
- $k_{clear}$ is a constant rate of elimination of therapeutic agent from plasma and has a value between 0.02 and 0.04 hour$^{-1}$;
- $k_{on}$ is an association rate of complex between the therapeutic agent and immune cells expressing IL-2 receptor and has a value between 0.26 and 4.5 µM$^{-1}$ h$^{-1}$;
- $k_{off}$ is a dissociation rate of complex between the therapeutic agent and immune cells expressing IL-2 receptor and has a value between 0.0035 and 0.02 h$^{-1}$,
- $k_{in}$ is a constant influx rate of IL2R+ cells in plasma and has a value between 0.0006 and 0.0144 µM·h$^{-1}$;
- $k_{out}$ is a natural decay rate of IL2R+ cells in plasma and has a value between 0.0018 and 0.069 h$^{-1}$,
- $k_{int}$ is the internalization rate of the therapeutic agent and has a value between 0.0066 and 0.023 h$^{-1}$; and
- $\eta$ is a constant rate of expansion of IL2R+ cells in plasma as a result of the binding (internalization) of the therapeutic agent and has a value between 1.02 and 3.31;

b) providing an optimal dosage regimen for the individual based on the increase in therapeutic agent required to compensate for reduction in free therapeutic agent;
wherein the therapeutic agent is a compound which is capable of targeting IL2R.

The optimal dosage regimen is preferably a regimen that when simulated using the model provides the best target tissue (e.g. tumor) uptake as compared to other simulated dosing regimens. The optimal dosage regimen may comprise an increase in the amount of therapeutic agent given in a single dose administration (as compared to a previous dose administration), it may comprise a change (e.g. reduction) in the time interval between doses (as compared to the time interval between previous doses), or it may comprise a combination of both. In some embodiments, the optimal dosage regimen is a combination of an amount of therapeutic agent given per dose administration and a time interval between dose administrations.

The method may also comprise the step of obtaining the PK and/or PD data from a sample obtained from the individual.

Further, in some embodiments, the method may also include the step of obtaining a sample from the individual following the initial dose administration, or following a previous dose administration.

In a second aspect, there is provided a method of treating an individual in need thereof with an effective dose of a therapeutic agent; wherein said effective dose is calculated using a model, such as a pharmacokinetic (PK) or pharmacokinetic/pharmacodynamic (PKPD) model, said method comprising the steps of a) simulating a model using data obtained from said individual at one or more time points following a first or previous dose administration of the therapeutic agent; wherein the data includes PK data relating to the amount of unbound therapeutic agent wherein the model is:

$$\frac{d[Ab]_{free}}{dt} = -k_{clear} \cdot [Ab]_{free} - (k_{on} \cdot [Ab]_{free} \cdot [IL2R]_{free} - k_{off} \cdot [Complex])$$

$$\frac{d[IL2R]_{free}}{dt} = k_{in} - k_{out} \cdot [IL2R]_{free} -$$

$$(k_{on} \cdot [Ab]_{free} \cdot [IL2R]_{free} - k_{off} \cdot [Complex]) + \eta \cdot k_{int} \cdot [Complex]$$

$$\frac{d[Complex]}{dt} = k_{on} \cdot [Ab]_{free} \cdot [IL2R]_{free} - k_{off} \cdot [Complex] - k_{int} \cdot [Complex]$$

wherein:
- $[Ab]_{free}$ is the concentration of unbound therapeutic agent in plasma,
- $[IL2R]_{free}$ is the concentration of unbound immune cells expressing IL2 receptor in blood and given by $k_{in}/k_{out}$ or optionally obtained from PD data,
- [Complex] is the concentration of complex between the therapeutic agent and immune cells expressing IL-2 receptor (IL2R+ cells),
- $k_{clear}$ a is a constant rate of elimination of therapeutic agent from plasma and has a value between 0.02 and 0.04 hour$^{-1}$;
- $k_{on}$ is an association rate of complex between the therapeutic agent and immune cells expressing IL-2 receptor and has a value between 0.26 and 4.5 µM$^{-1}$ h$^{-1}$;
- $k_{off}$ is a dissociation rate of complex between the therapeutic agent and immune cells expressing IL-2 receptor and has a value between 0.0035 and 0.02 h$^{-1}$,
- $k_{in}$ is a constant influx rate of IL2R+ cells in plasma and has a value between 0.0006 and 0.0144 lµM·h$^{-1}$;
- $k_{out}$ is a natural decay rate of IL2R+ cells in plasma and has a value between 0.0018 and 0.069 h$^{-1}$,
- $k_{int}$ is the internalization rate of the therapeutic agent and has a value between 0.0066 and 0.023 h$^{-1}$; and
- $\eta$ is a constant rate of expansion of IL2R+ cells in plasma as a result of the binding (internalization) of the therapeutic agent and has a value between 1.02 and 3.31;

b) determining an effective dose for the individual based on the increase in therapeutic agent required to compensate for reduction in free therapeutic agent; and
c) administering said effective dose to said individual;
wherein the therapeutic agent is a compound which is capable of targeting IL2R.

The effective dose may comprise an increase in the amount of the therapeutic agent relative to the first or previous dose administered, or it may have the same or even reduced amount but be administered within a shortened time interval since the previous dose administration relative to a previous time interval between dose administrations.

In some embodiments, the individual is being treated for cancer and the therapeutic agent is an anti-cancer drug. Preferably the cancer is a solid tumor. Treatment with the therapeutic agent may be in conjunction with other anti-cancer treatment.

This second aspect of the invention further provides a method for treating an individual in need thereof with an effective dose of a therapeutic agent comprising
  a) requesting a test providing results of an analysis to determine an effective amount of said therapeutic agent for the individual; and
  b) administering said therapeutic agent to the individual at the determined effective amount;
  wherein said test comprises
  a) simulating a model, such as a pharmacokinetic (PK) or pharmacokinetic/pharmacodynamic (PKPD) model, using data obtained from the individual at one or more time points following a first or previous dose administration of the therapeutic agent; wherein the data includes PK data relating to the amount of unbound therapeutic agent;
  wherein the model is:

$$\frac{d[Ab]_{free}}{dt} = -k_{clear} \cdot [Ab]_{free} - (k_{on} \cdot [Ab]_{free} \cdot [IL2R]_{free} - k_{off} \cdot [\text{Complex}])$$

$$\frac{d[IL2R]_{free}}{dt} = k_{in} - k_{out} \cdot [IL2R]_{free} -$$

$$(k_{on} \cdot [Ab]_{free} \cdot [IL2R]_{free} - k_{off} \cdot [\text{Complex}]) + \eta \cdot k_{int} \cdot [\text{Complex}]$$

$$\frac{d[\text{Complex}]}{dt} = k_{on} \cdot [Ab]_{free} \cdot [IL2R]_{free} - k_{off} \cdot [\text{Complex}] - k_{int} \cdot [\text{Complex}]$$

wherein:
  $[Ab]_{free}$ is the concentration of unbound therapeutic agent in plasma,
  $[IL2R]_{free}$ is the concentration of unbound immune cells expressing IL2 receptor in blood and given by $k_{in}/k_{out}$. or optionally obtained from PD data,
  [Complex] is the concentration of complex between the therapeutic agent and immune cells expressing IL-2 receptor (IL2R+ cells),
  $k_{clear}$ is a constant rate of elimination of therapeutic agent from plasma and has a value between 0.02 and 0.04 hour$^{-1}$;
  $k_{on}$ is an association rate of complex between the therapeutic agent and immune cells expressing IL-2 receptor and has a value between 0.26 and 4.5 µM$^{-1}$ h$^{-1}$;
  $k_{off}$ is a dissociation rate of complex between the therapeutic agent and immune cells expressing IL-2 receptor and has a value between 0.0035 and 0.02 h$^{-1}$,
  $k_{in}$ is a constant influx rate of IL2R+ cells in plasma and has a value between 0.0006 and 0.0144 µM·h$^{-1}$;
  $k_{out}$ is a natural decay rate of IL2R+ cells in plasma and has a value between 0.0018 and 0.069 h$^{-1}$, $k_{int}$ is the internalization rate of the therapeutic agent and has a value between 0.0066 and 0.023 h$^{-1}$; and
  η is a constant rate of expansion of IL2R+ cells in plasma as a result of the binding (internalization) of the therapeutic agent and has a value between 1.02 and 3.31;
  b) determining an effective dose for the individual based on the increase in therapeutic agent required to compensate for reduction in free therapeutic agent;
  wherein the therapeutic agent is a compound which is capable of targeting IL2R.

The effective dose may comprise an increase in the amount of the therapeutic agent relative to the first or previous dose administered, or it may have the same or even reduced amount but be administered within a shortened time interval since the previous dose administration relative to a previous time interval between dose administrations.

There is further provided a therapeutic agent (e.g. an IL2-based therapeutic agent) for use in a method of treating an individual; said method comprising administering to said individual an effective amount of the therapeutic agent, wherein said effective amount has been determined by applying PK and optionally PD data to a model, such as a pharmacokinetic (PK) or pharmacokinetic/pharmacodynamic (PKPD) model, according to the following formula:

$$\frac{d[Ab]_{free}}{dt} = -k_{clear} \cdot [Ab]_{free} - (k_{on} \cdot [Ab]_{free} \cdot [IL2R]_{free} - k_{off} \cdot [\text{Complex}])$$

$$\frac{d[IL2R]_{free}}{dt} = k_{in} - k_{out} \cdot [IL2R]_{free} -$$

$$(k_{on} \cdot [Ab]_{free} \cdot [IL2R]_{free} - k_{off} \cdot [\text{Complex}]) + \eta \cdot k_{int} \cdot [\text{Complex}]$$

$$\frac{d[\text{Complex}]}{dt} = k_{on} \cdot [Ab]_{free} \cdot [IL2R]_{free} - k_{off} \cdot [\text{Complex}] - k_{int} \cdot [\text{Complex}]$$

wherein:
  $[Ab]_{free}$ is the concentration of unbound therapeutic agent in plasma,
  $[IL2R]_{free}$ is the concentration of unbound immune cells expressing IL2 receptor in blood and given by $k_{in}/k_{out}$. or optionally obtained from PD data,
  [Complex] is the concentration of complex between the therapeutic agent and immune cells expressing IL-2 receptor (IL2R+ cells),
  $k_{clear}$ is a constant rate of elimination of therapeutic agent from plasma and has a value between 0.02 and 0.04 hour$^{-1}$;
  $k_{on}$ is an association rate of complex between the therapeutic agent and immune cells expressing IL-2 receptor and has a value between 0.26 and 4.5 µM$^{-1}$ h$^{-1}$;
  $k_{off}$ is a dissociation rate of complex between the therapeutic agent and immune cells expressing IL-2 receptor and has a value between 0.0035 and 0.02 h$^{-1}$,
  $k_{in}$ is a constant influx rate of IL2R+ cells in plasma and has a value between 0.0006 and 0.0144 µM·h$^{-1}$;
  $k_{out}$ is a natural decay rate of IL2R+ cells in plasma and has a value between 0.0018 and 0.069 h$^{-1}$,
  $k_{int}$ is the internalization rate of the therapeutic agent and has a value between 0.0066 and 0.023 h$^{-1}$; and
  η is a constant rate of expansion of IL2R+ cells in plasma as a result of the binding (internalization) of the therapeutic agent and has a value between 1.02 and 3.31;
  wherein the data includes (i) PK data relating to the amount of unbound therapeutic agent; and optionally (ii) PD data relating to immune cells expressing IL2 receptor obtained from the individual at one or more time points after a first or previous dose administration of the therapeutic agent.

Still further, there is provided a method of optimising therapeutically effective treatment of an individual suffering from cancer, said method comprising
  a) administering a first or previous dose administration of a therapeutic agent (e.g. IL2-based therapeutic agent);
  b) obtaining PK and optionally PD data from said individual at one or more time points following first or previous dose administration of said therapeutic agent;
  c) applying said PK and optional PD data to a model, such as a pharmacokinetic (PK) or pharmacokinetic/pharmacodynamic (PKPD) model, to predict the loss of free circulating therapeutic agent following said first or previous dose administration;

d) providing a dosage regimen for at least a second dose administration, wherein said dosage regimen provides an adjusted amount of therapeutic agent to compensate for the predicted loss in free circulating agent by virtue of increase in amount of a single dose, a reduction in time-interval between doses or a combination of both; and e) administering said at least second dose administration in accordance with the dosage regimen;

wherein the model is $$\frac{d[Ab]_{free}}{dt} = -k_{clear} \cdot [Ab]_{free} - (k_{on} \cdot [Ab]_{free} \cdot [IL2R]_{free} - k_{off} \cdot [Complex])$$

$$\frac{d[IL2R]_{free}}{dt} = k_{in} - k_{out} \cdot [IL2R]_{free} -$$

$$(k_{on} \cdot [Ab]_{free} \cdot [IL2R]_{free} - k_{off} \cdot [Complex]) + \eta \cdot k_{int} \cdot [Complex]$$

$$\frac{d[Complex]}{dt} = k_{on} \cdot [Ab]_{free} \cdot [IL2R]_{free} - k_{off} \cdot [Complex] - k_{int} \cdot [Complex]$$

wherein:

$[Ab]_{free}$ is the concentration of unbound therapeutic agent in plasma, $[IL2R]_{free}$ is the concentration of unbound immune cells expressing IL2 receptor in blood and given by $k_{in}/k_{out}$, or optionally obtained from PD data,

[Complex] is the concentration of complex between the therapeutic agent and immune cells expressing IL-2 receptor (IL2R+ cells), $k_{clear}$ is a constant rate of elimination of therapeutic agent from plasma and has a value between 0.02 and 0.04 hour$^{-1}$;

$k_{on}$ is an association rate of complex between the therapeutic agent and immune cells expressing IL-2 receptor and has a value between 0.26 and 4.5 $\mu M^{-1}$ h$^{-1}$;

$k_{off}$ is a dissociation rate of complex between the therapeutic agent and immune cells expressing IL-2 receptor and has a value between 0.0035 and 0.02 h$^{-1}$, $k_{in}$ is a constant influx rate of IL2R+ cells in plasma and has a value between 0.0006 and 0.0144 $\mu M \cdot h^{-1}$;

$k_{out}$ is a natural decay rate of IL2R+ cells in plasma and has a value between 0.0018 and 0.069 h$^{-1}$, $k_{int}$ is the internalization rate of the therapeutic agent and has a value between 0.0066 and 0.023 h$^{-1}$; and η is a constant rate of expansion of IL2R+ cells in plasma as a result of the binding (internalization) of the therapeutic agent and has a value between 1.02 and 3.31;

and wherein the data includes (i) PK data relating to the amount of unbound therapeutic agent; and optionally (ii) PD data relating to immune cells expressing IL2 receptor.

In accordance with this and any other aspect of the invention, the therapeutic agent may be cergutuzumab amunaleukin (CEA-IL2v) or FAP-IL2v.

The PKPD model provided herein has allowed an optimised dosage regimen to be designed for cergutuzumab amunaleukin (CEA-IL2v) and FAP-IL2v.

Accordingly, the invention further provides an optimised dosage regimen for treating an individual suffering from cancer with cergutuzumab amunaleukin, said dosage regimen comprising (i) administering to said individual a first and optionally a second dose of cergutuzumab amunaleukin of up to 30 mg, preferably 20 mg, (ii) collecting PK data (and optionally PD data) from said individual after administration of said first and/or second dose and simulating a model in accordance with the first aspect of the invention to predict the TMDD using said PK data (and optionally PD data);

(iii) administering to said individual a further dose of cergutuzumab amunaleukin, said further dose having been adjusted relative to said first and optional second dose based on TMDD determined in step (ii); and (iv) optionally repeat steps (ii) and (iii).

The time interval between dose administrations may be one or two weeks, preferably one week.

The further dose in step (iii) may be the same as the previous dose(s) in individuals wherein low TMDD is predicted in step (ii).

By way of example, in one embodiment, an optimised dosage regimen for cergutuzumab amunaleukin may comprise:

(i) administering to said individual a first and a second dose (D1 and D2) of 20 mg cergutuzumab amunaleukin, and (ii) administering to said individual a third and optionally further doses (D3) of 25 mg cergutuzumab amunaleukin, wherein the time interval between dose administrations is one week or two weeks, preferably one week.

In another exemplary embodiment, an optimised dosage regimen for cergutuzumab amunaleukin may comprise:

(i) administering to said individual a first and a second dose (D1 and D2) of 20 mg cergutuzumab amunaleukin, (ii) administering to said individual a third and a fourth dose (D3 an d D4) of 25 mg cergutuzumab amunaleukin, and (iii) administering to said individual a fifth and optionally further doses (D5) of 30 mg cergutuzumab amunaleukin, wherein the time interval between dose administrations is one week or two weeks, preferably one week.

In still another embodiment, an optimised dosage regimen for cergutuzumab amunaleukin may comprise:

(i) administering to said individual a first and a second dose (D1 and D2) of 20 mg cergutuzumab amunaleukin, (ii) administering to said individual a third and a fourth dose (D3 an d D4) of 30 mg cergutuzumab amunaleukin, (iii) administering to said individual a fifth and a sixth dose (D5 and D6) of 40 mg cergutuzumab amunaleukin, and (iv) administering to said individual a seventh and optionally further doses (D7) of 45 mg cergutuzumab amunaleukin;

wherein the time interval between dose administrations is one week or two weeks, preferably one week.

The invention further provides an optimised dosage regimen for treating an individual suffering from cancer with FAP-IL2v, said dosage regimen comprising (i) administering to said individual a first and optionally a second dose of FAP-IL2v of up to 40 mg, preferably 20 mg, (ii) collecting PK data (an optionally PD data) from said individual after administration of said first and/or second dose and simulating a model in accordance with the first aspect of the invention to predict the TMDD using said PK data (and optionally PD data);

(iii) administering to said individual a further dose of FAP-IL2v, said further dose having been adjusted relative to said first and optional second dose based on TMDD determined in step (ii); and (iv) optionally repeat steps (ii) and (iii).

The time interval between dose administrations may be one or two weeks, preferably one week.

The further dose in step (iii) may be the same as the previous dose(s) in individuals wherein low TMDD is predicted in step (ii).

In a third aspect, there is provided a network system for determining an effective dose or a dosage regimen for an individual being treated with a therapeutic agent (e.g. an IL2-based therapeutic agent); said system comprising a dosage determining apparatus and an information communication terminal apparatus, said dosage determining apparatus including a control component and a memory component, said apparatuses being communicatively connected to each other via a network;

(1) wherein the information communication terminal apparatus includes (1a) a data sending unit that transmits the PK and optionally PD data derived from a sample obtained from an individual having a first dose administration of said therapeutic agent to the dosage determining apparatus;

(1b) a result-receiving unit that receives the determined effective second dose administration for the subject transmitted from the effective dose determining apparatus;

(2) wherein the effective dose determining apparatus includes (2a) a PK and optionally PD data-receiving unit that receives PK and PD data derived from the sample obtained from the individual transmitted from the information communication terminal apparatus;

(2b) a data processing unit which processes the data from the data-receiving unit using a model, such as a PK or a PKPD model;

(2c) a dose-calculating unit that determines the second effective dose required by the individual to maintain a therapeutically effective level of the therapeutic agent, based on the results of the data processing unit; and (2d) an effective dose result-sending unit that transmits the calculated effective second dose for the individual obtained by the dose-calculating unit to the information communication terminal apparatus; wherein the effective dose includes an increase in the amount of therapeutic agent in a single dose and/or a change (e.g. reduction) in the time interval between doses having the same or altered amount of therapeutic agent; wherein the model is $$\frac{d[Ab]_{free}}{dt} = -k_{clear} \cdot [Ab]_{free} - (k_{on} \cdot [Ab]_{free} \cdot [IL2R]_{free} - k_{off} \cdot [Complex])$$

$$\frac{d[IL2R]_{free}}{dt} = k_{in} - k_{out} \cdot [IL2R]_{free} -$$

$$(k_{on} \cdot [Ab]_{free} \cdot [IL2R]_{free} - k_{off} \cdot [Complex]) + \eta \cdot k_{int} \cdot [Complex]$$

$$\frac{d[Complex]}{dt} = k_{on} \cdot [Ab]_{free} \cdot [IL2R]_{free} - k_{off} \cdot [Complex] - k_{int} \cdot [Complex]$$

wherein:

[Ab]$_{free}$ is the concentration of unbound therapeutic agent in plasma,

[IL2R]$_{free}$ is the concentration of unbound immune cells expressing IL2 receptor in blood and given by $k_{in}/k_{out}$ or optionally obtained from PD data,

[Complex] is the concentration of complex between the therapeutic agent and immune cells expressing IL-2 receptor (IL2R+ cells), $k_{clear}$ is a constant rate of elimination of therapeutic agent from plasma and has a value between 0.02 and 0.04 hour$^{-1}$;

$k_{on}$ is an association rate of complex between the therapeutic agent and immune cells expressing IL-2 receptor and has a value between 0.26 and 4.5 µM$^{-1}$ h$^{-1}$;

$k_{off}$ is a dissociation rate of complex between the therapeutic agent and immune cells expressing IL-2 receptor and has a value between 0.0035 and 0.02 h$^{-1}$, $k_{in}$ is a constant influx rate of IL2R+ cells in plasma and has a value between 0.0006 and 0.0144 µM·h$^{-1}$;

$k_{out}$ is a natural decay rate of IL2R+ cells in plasma and has a value between 0.0018 and 0.069 h$^{-1}$, $k_{int}$ is the internalization rate of the therapeutic agent and has a value between 0.0066 and 0.023 h$^{-1}$; and η is a constant rate of expansion of IL2R+ cells in plasma as a result of the binding (internalization) of the therapeutic agent and has a value between 1.02 and 3.31;

and wherein the data includes (i) PK data relating to the amount of unbound therapeutic agent; and optionally (ii) PD data relating to immune cells expressing IL2 receptor obtained from the individual at one or more time points after a first or previous dose administration of the therapeutic agent.

The model may be extended to incorporate the uptake process. A last equation is then added:

$$\frac{d[Ab]_{total}^T}{dt} = \frac{2 \cdot P \cdot R_{Cap}}{R_{Kgrogh}^2}\left([Ab]_{free} - \left(\frac{Kd}{\left(\frac{[Ag]}{\varepsilon}\right)+K_D}\right)\frac{[Ab]_{total}^T}{\varepsilon}\right) -$$

$$k_e\left(\frac{\frac{[Ag]}{\varepsilon}}{\left(\frac{[Ag]}{\varepsilon}\right)+K_D}\right)[Ab]_{total}^T$$

Following the assumption that tumor uptake does not impact peripheral PK, all parameters related to peripheral PK were fixed to the population values reported above and uptake imaging data (from an imaging sub-study with Zr89-radiolabeled CEA-IL2v) were analysed using the equation above.

The parameters indicated in the equations above were estimated by formulating a mixed effect model on the basis of the three equations reported above and fitting only longitudinal PK data (concentration of unbound CEA-IL2v in blood). For these reasons, provided herein are a range for the values and a mean value and a standard deviation of the distribution of parameter values across the studied population. Note that the parameters were assumed to be log-normally distributed. The inventors also assumed a proportional error model with parameter b estimated at 0.351.

In all aspects of the present invention, the baseline value of [IL2R]$_{free}$ compartment is—by mathematical construction—given by $k_{in}/k_{out}$. Then, its evolution is governed by the model parameters all inferred through the use of the PK observations. Accordingly, there is no requirement for PD data in order to simulate the model. In this case, this compartment does not "physically" represent cells but rather a virtual compartment also called latent variable that is in there to correctly describe the PK kinetic. However, in some embodiments, PD data relating to (unbound) immune cells expressing IL2 receptor may be collected and used for parameter $[IL2R]_{free}$ instead of $k_{in}/k_{out}$.

The present invention includes the combination of the aspects and preferred features described herein except where such a combination is clearly impermissible or is stated to be expressly avoided. These and further aspects and embodiments of the invention are described in further detail below and with reference to the accompanying examples and figures. The contents of all documents mentioned herein are expressly hereby incorporated by reference.

DESCRIPTION OF THE FIGURES

FIG. 5A, FIG. 5B, FIG. 5C: Cycle 1 pharmacokinetic profiles of CEA-IL2v in patients with dose 6 mg (A, n=18); 20 mg (B, n=33); 30 mg and higher (C, n=23).

FIG. 5D: Change in exposure across first three cycles. QW regimen (continuous line, n=5) and Q2W regimen (dashed line, n=7). FIG. 5E: Uptake of CEA-IL2v in CEA+ tumor lesions at cycle 1 in patients with dose 6 mg (n=4, dashed lines) and CEA+ tumor lesions at cycle 1 in patients with dose 30 mg (n=4, continuous line).

FIG. 6A, FIG. 6B, FIG. 6C, FIG. 6D, FIG. 6E, FIG. 6F, FIG. 6G, FIG. 6H, FIG. 6I: Model performance and validation. FIG. 6A, FIG. 6B, FIG. 6C: Visual predictive check (VPC) of PK profiles in the 50 patients used for model construction. Black areas show model predicted 90, 50 and 10 percentiles. Grey lines show empirical percentiles of observed data (FIG. 6A); Normalized prediction distribution errors (NPDE) versus time (FIG. 6B); NPDE versus predictions (FIG. 6C). FIG. 6D, FIG. 6E, FIG. 6F: VPC of PK profiles in the 24 patients whose data were not used to build the model (FIG. 6D); Predicted CEA-IL2v target concentration versus observed concentration of IL2R+ cells (CD4+, CD8+ and NK cells) in blood (FIG. 6E); Predicted CEA-IL2v target exposure versus observed sCD25 exposure (FIG. 6F).

FIG. 6G, FIG. 6H, FIG. 6I: Observed versus predicted uptake in tumor lesions in the four patients CEA+ patients treated with 30 mg of CEA-IL2v (FIG. 6G); Predicted uptake in CRC CEA+ patients with 30 mg (continuous line) including observations used to calibrate the model (circles) and extrapolation to 20 mg (dashed line) together with uptake data from 2 patients (squares and triangles) at 20 mg whose data were not used to build the model (FIG. 6H); Predicted tumor uptake at cycle 4 with (dashed thick line) or without (dashed thin line) correction of prediction with expansion of target in periphery together with uptake data from 1 patient that received 20 mg at cycle 1 and 30 mg cycles 2 to 4, whose data were not used to build the model (FIG. 6I).

FIG. 7A, FIG. 7B: Predicted pharmacokinetic population profile through 4 cycles 20 mg QW (FIG. 7A); Predicting corresponding tumor uptake (FIG. 7B);

FIG. 7C: Predicted tumor uptake in QW when dose is increased by 5 mg each cycle (20, 25, 30 and 35 mg). The dashed line is the reference uptake for 20 mg QW without applying correction for target expansion.

FIG. 7D: Predicted tumor uptake for 20 mg 4 cycles when dosing interval is shortened (7 days between cycle 1 and 2, 5 days between cycle 2 and 3, and 3 days between cycle 3 and 4). The dashed line is the reference uptake for 20 mg QW without applying correction for target expansion.

FIG. 8A, FIG. 8B, FIG. 8C: Patient's treatment individualization. Individual prediction of PK profile in a given patient when only data at cycle 1 is used (circle). Prediction at further cycle is shown in dashed line together with observation (not used to calibrate the model) for the same individual (stars) (FIG. 8A). Predicted tumor uptake for this given individual. The dashed line is the reference uptake for 20 mg QW without applying correction for target expansion (FIG. 8B). Predicted uptake with dose given every 5 days, starting at 20 mg and incrementing by 5 mg at each cycle. The resulting uptake is comparable to the theoretical uptake without expansion (dashed line) (FIG. 8C).

DEFINITIONS

Figure 1:
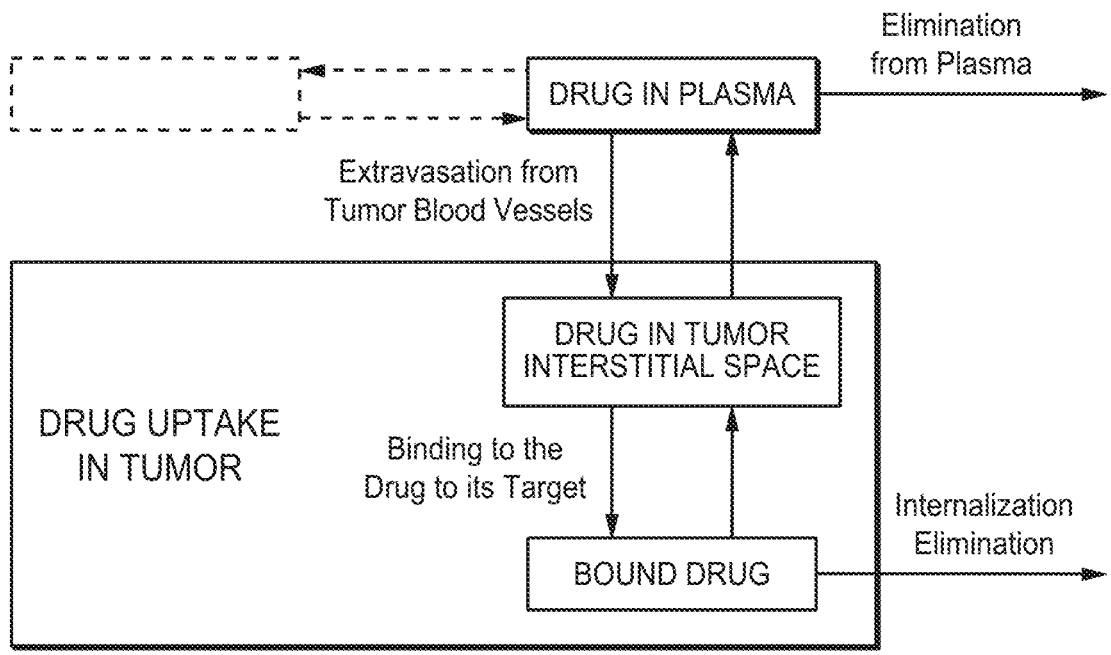
FIG. 1: Schematic representation of the modelling formalism for antibody tumor uptake. From plasma, the drug can distribute in different tissues including tumor. After extravasion from tumor blood vessels, the drug will diffuse into the interstitial space and will bind to specific antigen (e.g. CEA or FAP).

As used herein, the term "cytokine" refers to a molecule that mediates and/or regulates a biological or cellular function or process (e.g. immunity, inflammation, and hematopoiesis).

The term "cytokine" as used herein includes "lymphokines," "chemokines," "monokines," and "interleukins". Examples of useful cytokines include, but are not limited to, GM-CSF, IL-1α, IL-1β, IL-2, IL-3, IL-4, IL-5, IL-6, IL-7, IL-8, IL-10, IL-12, IL-15, IFN-α, IFN-β, IFN-γ, MIP-1α, MIP-1β, TGF-β, TNF-α, and TNF-β. A particular cytokines is IL-2. The term "cytokine" as used herein is meant to also include cytokine variants comprising one or more amino acid mutations in the amino acid sequences of the corresponding wild-type cytokine, such as for example the IL-2 variants described in Sauve et al., Proc Natl Acad Sci USA 88, 4636-40 (1991); Hu et al., Blood 101, 4853-4861 (2003) and US Pat. Publ. No. 2003/0124678; Shanafelt et al., Nature Biotechnol 18, 1197-1202 (2000); Heaton et al., Cancer Res 53, 2597-602 (1993) and U.S. Pat. No. 5,229,109; US Pat. Publ. No. 2007/0036752; WO 2008/0034473; WO 2009/061853; or in WO 2012/107417.

The term "interleukin-2" or "IL-2" as used herein, refers to any native IL-2 from any vertebrate source, including mammals such as primates (e.g. humans) and rodents (e.g., mice and rats), unless otherwise indicated. The term encompasses unprocessed IL-2 as well as any form of IL-2 that results from processing in the cell. The term also encompasses naturally occurring variants of IL-2, e.g. splice variants or allelic variants. The amino acid sequence of an exemplary human IL-2 is shown in SEQ ID NO: 1. Unprocessed human IL-2 additionally comprises an N-terminal 20 amino acid signal peptide having the sequence of SEQ ID NO: 20, which is absent in the mature IL-2 molecule.

The term "interleukin-2" as used herein is meant to also include IL-2 variants comprising one or more amino acid mutations in the amino acid sequences of the corresponding wild-type cytokine, such as for example the IL-2 variants described in Sauvé et al., Proc Natl Acad Sci USA 88, 4636-40 (1991); Hu et al., Blood 101, 4853-4861 (2003) and US Pat. Publ. No. 2003/0124678; Shanafelt et al., Nature Biotechnol 18, 1197-1202 (2000); Heaton et al., Cancer Res 53, 2597-602 (1993) and U.S. Pat. No. 5,229,109; US Pat. Publ. No. 2007/0036752; WO 2008/0034473; WO 2009/061853; or in WO 2012/107417.

The term "IL-2 mutant" or "mutant IL-2 polypeptide" as used herein is intended to encompass any mutant forms of various forms of the IL-2 molecule including full-length IL-2, truncated forms of IL-2 and forms where IL-2 is linked to another molecule such as by fusion or chemical conjugation. "Full-length" when used in reference to IL-2 is intended to mean the mature, natural length IL-2 molecule. For example, full-length human IL-2 refers to a molecule that has 133 amino acids (see e.g. SEQ ID NO: 1). The various forms of IL-2 mutants are characterized in having a at least one amino acid mutation affecting the interaction of IL-2 with CD25. This mutation may involve substitution, deletion, truncation or modification of the wild-type amino acid residue normally located at that position. Mutants obtained by amino acid substitution are preferred. Unless otherwise indicated, an IL-2 mutant may be referred to herein as an IL-2 mutant peptide sequence, an IL-2 mutant polypeptide, IL-2 mutant protein or IL-2 mutant analog. Designation of various forms of IL-2 is herein made with respect to the sequence shown in SEQ ID NO: 1. Various designations may be used herein to indicate the same mutation. For example a mutation from phenylalanine at position 42 to alanine can be indicated as 42A, A42, $A_{42}$, F42A, or Phe42Ala.

The term "amino acid mutation" as used herein is meant to encompass amino acid substitutions, deletions, insertions, and modifications. Any combination of substitution, deletion, insertion, and modification can be made to arrive at the final construct, provided that the final construct possesses the desired characteristics, e.g., reduced binding to CD25. Amino acid sequence deletions and insertions include amino- and/or carboxy-terminal deletions and insertions of amino acids. Particular amino acid mutations are amino acid substitutions. For the purpose of altering e.g. the binding characteristics of an IL-2 polypeptide or an Fc region, non-conservative amino acid substitutions, i.e. replacing one amino acid with another amino acid having different structural and/or chemical properties, are particularly preferred. Amino acid substitutions include replacement by non-naturally occurring amino acids or by naturally occurring amino acid derivatives of the twenty standard amino acids (e.g. 4-hydroxyproline, 3-methylhistidine, ornithine, homoserine, 5-hydroxylysine). Amino acid mutations can be generated using genetic or chemical methods well known in the art. Genetic methods may include site-directed mutagenesis, PCR, gene synthesis and the like. It is contemplated that methods of altering the side chain group of an amino acid by methods other than genetic engineering, such as chemical modification, may also be useful. Various designations may be used herein to indicate the same amino acid mutation. For example, a substitution from proline at position 329 of the Fc region to glycine can be indicated as 329G, G329, $G_{329}$, P329G, or Pro329Gly.

The term "CD25" or "α-subunit of the IL-2 receptor" as used herein, refers to any native CD25 from any vertebrate source, including mammals such as primates (e.g. humans) and rodents (e.g., mice and rats), unless otherwise indicated. The term encompasses "full-length", unprocessed CD25 as well as any form of CD25 that results from processing in the cell. The term also encompasses naturally occurring variants of CD25, e.g. splice variants or allelic variants. In certain embodiments CD25 is human CD25. The amino acid sequence of human CD25 is shown in UniProt (www.uniprot.org) accession no. P01589, or NCBI (www.ncbi.nlm.nih.gov/) Ref Seq NP_000408.

The term "high-affinity IL-2 receptor" as used herein refers to the heterotrimeric form of the IL-2 receptor, consisting of the receptor γ-subunit (also known as common cytokine receptor γ-subunit, $γ_c$, or CD132), the receptor β-subunit (also known as CD122 or p70) and the receptor α-subunit (also known as CD25 or p55). The term "intermediate-affinity IL-2 receptor" by contrast refers to the IL-2 receptor including only the γ-subunit and the β-subunit, without the α-subunit (for a review see e.g. Olejniczak and Kasprzak, Med Sci Monit 14, RA179-189 (2008)).

"Affinity" refers to the strength of the sum total of non-covalent interactions between a single binding site of a molecule (e.g., a receptor) and its binding partner (e.g., a ligand). Unless indicated otherwise, as used herein, "binding affinity" refers to intrinsic binding affinity which reflects a 1:1 interaction between members of a binding pair (e.g., receptor and a ligand). The affinity of a molecule X for its partner Y can generally be represented by the dissociation constant ($K_D$), which is the ratio of dissociation and association rate constants ($k_{off}$ and $k_{on}$, respectively). Thus, equivalent affinities may comprise different rate constants, as long as the ratio of the rate constants remains the same. Affinity can be measured by well established methods known in the art. A particular method for measuring affinity is Surface Plasmon Resonance (SPR).

"Reduction" (and grammatical variations thereof such as "reduce" or "reducing"), for example reduction of the number of B cells or the formation of ADAs, refers to a decrease in the respective quantity, as measured by appropriate methods known in the art. For clarity the term includes also reduction to zero (or below the detection limit of the analytical method), i.e. complete abolishment or elimination. Conversely, "increased" refers to an increase in the respective quantity.

By "regulatory T cell" or "$T_{reg}$ cell" is meant a specialized type of CD4+ T cell that can suppress the responses of other T cells. $T_{reg}$ cells are characterized by expression of the α-subunit of the IL-2 receptor (CD25) and the transcription factor forkhead box P3 (FOXP3) (Sakaguchi, Annu Rev Immunol 22, 531-62 (2004)) and play a critical role in the induction and maintenance of peripheral self-tolerance to antigens, including those expressed by tumors. $T_{reg}$ cells require IL-2 for their function and development and induction of their suppressive characteristics.

As used herein, the term "antigen binding moiety" refers to a polypeptide molecule that specifically binds to an antigenic determinant. In one embodiment, an antigen binding moiety is able to direct the entity to which it is attached (e.g. a cytokine or a second antigen binding moiety) to a target site, for example to a specific type of tumor cell bearing the antigenic determinant. Antigen binding moieties include antibodies and fragments thereof as further defined herein. Preferred antigen binding moieties include an antigen binding domain of an antibody, comprising an antibody heavy chain variable region and an antibody light chain variable region. In certain embodiments, the antigen binding moieties may include antibody constant regions as further defined herein and known in the art. Useful heavy chain constant regions include any of the five isotypes: α, δ, ε, γ, or μ. Useful light chain constant regions include any of the two isotypes: κ and λ.

By "specifically binds" is meant that the binding is selective for the antigen and can be discriminated from unwanted or non-specific interactions. The ability of an antigen binding moiety to bind to a specific antigenic determinant can be measured either through an enzyme-linked immunosorbent assay (ELISA) or other techniques familiar to one of skill in the art, e.g. surface plasmon resonance technique (analyzed on a BIAcore instrument) (Liljeblad et al., Glyco J 17, 323-329 (2000)), and traditional binding assays (Heeley, Endocr Res 28, 217-229 (2002)).

As used herein, the term "antigenic determinant" is synonymous with "antigen" and "epitope," and refers to a site (e.g. a contiguous stretch of amino acids or a conformational configuration made up of different regions of non-contiguous amino acids) on a polypeptide macromolecule to which an antigen binding moiety binds, forming an antigen binding moiety-antigen complex. Useful antigenic determinants can be found, for example, on the surfaces of tumor cells, on the surfaces of virus-infected cells, on the surfaces of other diseased cells, free in blood serum, and/or in the extracellular matrix (ECM).

As used herein, term "polypeptide" refers to a molecule composed of monomers (amino acids) linearly linked by amide bonds (also known as peptide bonds). The term "polypeptide" refers to any chain of two or more amino acids, and does not refer to a specific length of the product. Thus, peptides, dipeptides, tripeptides, oligopeptides, "protein," "amino acid chain," or any other term used to refer to a chain of two or more amino acids, are included within the definition of "polypeptide," and the term "polypeptide" may be used instead of, or interchangeably with any of these terms. The term "polypeptide" is also intended to refer to the products of post-expression modifications of the polypeptide, including without limitation glycosylation, acetylation, phosphorylation, amidation, derivatization by known protecting/blocking groups, proteolytic cleavage, or modification by non-naturally occurring amino acids. A polypeptide may be derived from a natural biological source or produced by recombinant technology, but is not necessarily translated from a designated nucleic acid sequence. It may be generated in any manner, including by chemical synthesis. A polypeptide of the invention may be of a size of about 3 or more, 5 or more, 10 or more, 20 or more, 25 or more, 50 or more, 75 or more, 100 or more, 200 or more, 500 or more, 1,000 or more, or 2,000 or more amino acids. Polypeptides may have a defined three-dimensional structure, although they do not necessarily have such structure. Polypeptides with a defined three-dimensional structure are referred to as folded, and polypeptides which do not possess a defined three-dimensional structure, but rather can adopt a large number of different conformations, and are referred to as unfolded.

By an "isolated" polypeptide or a variant, or derivative thereof is intended a polypeptide that is not in its natural milieu. No particular level of purification is required. For example, an isolated polypeptide can be removed from its native or natural environment. Recombinantly produced polypeptides and proteins expressed in host cells are considered isolated for the purpose of the invention, as are native or recombinant polypeptides which have been separated, fractionated, or partially or substantially purified by any suitable technique.

"Percent (%) amino acid sequence identity" with respect to a reference polypeptide sequence is defined as the percentage of amino acid residues in a candidate sequence that are identical with the amino acid residues in the reference polypeptide sequence, after aligning the sequences and introducing gaps, if necessary, to achieve the maximum percent sequence identity, and not considering any conservative substitutions as part of the sequence identity. Alignment for purposes of determining percent amino acid sequence identity can be achieved in various ways that are within the skill in the art, for instance, using publicly available computer software such as BLAST, BLAST-2, ALIGN or Megalign (DNASTAR) software. Those skilled in the art can determine appropriate parameters for aligning sequences, including any algorithms needed to achieve maximal alignment over the full length of the sequences being compared. For purposes herein, however, % amino acid sequence identity values are generated using the sequence comparison computer program ALIGN-2. The ALIGN-2 sequence comparison computer program was authored by Genentech, Inc., and the source code has been filed with user documentation in the U.S. Copyright Office, Washington D.C., 20559, where it is registered under U.S. Copyright Registration No. TXU510087. The ALIGN-2 program is publicly available from Genentech, Inc., South San Francisco, California, or may be compiled from the source code. The ALIGN-2 program should be compiled for use on a UNIX operating system, including digital UNIX V4.0D. All sequence comparison parameters are set by the ALIGN-2 program and do not vary. In situations where ALIGN-2 is employed for amino acid sequence comparisons, the % amino acid sequence identity of a given amino acid sequence A to, with, or against a given amino acid sequence B (which can alternatively be phrased as a given amino acid sequence A that has or comprises a certain % amino acid sequence identity to, with, or against a given amino acid sequence B) is calculated as follows:

$$100 \text{ times the fraction } X/Y$$

where X is the number of amino acid residues scored as identical matches by the sequence alignment program ALIGN-2 in that program's alignment of A and B, and where Y is the total number of amino acid residues in B. It will be appreciated that where the length of amino acid sequence A is not equal to the length of amino acid sequence B, the % amino acid sequence identity of A to B will not equal the % amino acid sequence identity of B to A. Unless specifically stated otherwise, all % amino acid sequence identity values used herein are obtained as described in the immediately preceding paragraph using the ALIGN-2 computer program.

As used herein, the term "effector moiety" refers to a polypeptide, e.g., a protein or glycoprotein that influences cellular activity, for example, through signal transduction or other cellular pathways. Accordingly, the effector moiety can be associated with receptor-mediated signaling that transmits a signal from outside the cell membrane to modulate a response in a cell bearing one or more receptors for the effector moiety. In one embodiment, an effector moiety can elicit a cytotoxic response in cells bearing one or more receptors for the effector moiety. In another embodiment, an effector moiety can elicit a proliferative response in cells bearing one or more receptors for the effector moiety. In another embodiment, an effector moiety can elicit differentiation in cells bearing receptors for the effector moiety. In another embodiment, an effector moiety can alter expression (i.e. upregulate or downregulate) of an endogenous cellular protein in cells bearing receptors for the effector moiety. Non-limiting examples of effector moieties include cytokines, growth factors, hormones, enzymes, substrates, and cofactors. An effector moiety can be associated with an antigen binding moiety such as an antibody in a variety of configurations to form an immunoconjugate.

The term "cytotoxic agent" as used herein refers to a substance that inhibits or prevents a cellular function and/or causes cell death or destruction. Cytotoxic agents include, but are not limited to, radioactive isotopes (e.g., $At^{211}$, $I^{131}$, $I^{125}$, $Y^{90}$, $Re^{186}$, $Re^{188}$, $Sm^{153}$, $Bi^{212}$, $P^{32}$, $Pb^{212}$ and radioactive isotopes of Lu); chemotherapeutic agents or drugs (e.g., methotrexate, adriamicin, *vinca* alkaloids (vincristine, vinblastine, etoposide), doxorubicin, melphalan, mitomycin C, chlorambucil, daunorubicin or other intercalating agents); growth inhibitory agents; enzymes and fragments thereof such as nucleolytic enzymes; antibiotics; toxins such as small molecule toxins or enzymatically active toxins of bacterial, fungal, plant or animal origin, including fragments and/or variants thereof; and the various antitumor or anticancer agents disclosed below.

The term "antibody" herein is used in the broadest sense and encompasses various antibody structures, including but not limited to monoclonal antibodies, polyclonal antibodies, multispecific antibodies (e.g. bispecific antibodies), and antibody fragments so long as they exhibit the desired antigen binding activity.

The terms "full length antibody," "intact antibody," and "whole antibody" are used herein interchangeably to refer to an antibody having a structure substantially similar to a native antibody structure or having heavy chains that contain an Fc region as defined herein.

An "antibody fragment" refers to a molecule other than an intact antibody that comprises a portion of an intact antibody that binds the antigen to which the intact antibody binds. Examples of antibody fragments include but are not limited to Fv, Fab, Fab', Fab'-SH, F(ab')$_2$, diabodies, linear antibodies, single-chain antibody molecules (e.g. scFv), and multispecific antibodies formed from antibody fragments.

The term "immunoglobulin molecule" refers to a protein having the structure of a naturally occurring antibody. For example, immunoglobulins of the IgG class are heterotetrameric glycoproteins of about 150,000 daltons, composed of two light chains and two heavy chains that are disulfide-bonded. From N- to C-terminus, each heavy chain has a variable region (VH), also called a variable heavy domain or a heavy chain variable domain, followed by three constant domains (CH1, CH2, and CH3), also called a heavy chain constant region. Similarly, from N- to C-terminus, each light chain has a variable region (VL), also called a variable light domain or a light chain variable domain, followed by a constant light (CL) domain, also called a light chain constant region. The heavy chain of an immunoglobulin may be assigned to one of five classes, called α (IgA), δ (IgD), ε (IgE), γ (IgG), μ (IgM), some of which may be further divided into subclasses, e.g. $γ_1$ ($IgG_1$), $γ_2$ ($IgG_2$), $γ_3$ ($IgG_3$), $γ_4$ ($IgG_4$), $α_1$ ($IgA_1$) and $α_2$ ($IgA_2$). The light chain of an immunoglobulin may be assigned to one of two types, called kappa (κ) and lambda (λ), based on the amino acid sequence of its constant domain. An immunoglobulin essentially consists of two Fab molecules and an Fc domain, linked via the immunoglobulin hinge region.

The term "antigen binding domain" refers to the part of an antibody that comprises the area which specifically binds to and is complementary to part or all of an antigen. An antigen binding domain may be provided by, for example, one or more antibody variable domains (also called antibody variable regions). Preferably, an antigen binding domain comprises an antibody light chain variable region (VL) and an antibody heavy chain variable region (VH).

The term "variable region" or "variable domain" refers to the domain of an antibody heavy or light chain that is involved in binding the antibody to antigen. The variable domains of the heavy chain and light chain (VH and VL, respectively) of a native antibody generally have similar structures, with each domain comprising four conserved framework regions (FRs) and three hypervariable regions (HVRs). See, e.g., Kindt et al., Kuby Immunology, 6$^{th}$ ed., W.H. Freeman and Co., page 91 (2007). A single VH or VL domain may be sufficient to confer antigen binding specificity.

A "human antibody" is one which possesses an amino acid sequence which corresponds to that of an antibody produced by a human or a human cell or derived from a non-human source that utilizes human antibody repertoires or other human antibody-encoding sequences. This definition of a human antibody specifically excludes a humanized antibody comprising non-human antigen-binding residues.

A "humanized" antibody refers to a chimeric antibody comprising amino acid residues from non-human HVRs and amino acid residues from human FRs. In certain embodiments, a humanized antibody will comprise substantially all of at least one, and typically two, variable domains, in which all or substantially all of the HVRs (e.g., CDRs) correspond to those of a non-human antibody, and all or substantially all of the FRs correspond to those of a human antibody. A humanized antibody optionally may comprise at least a portion of an antibody constant region derived from a human antibody. A "humanized form" of an antibody, e.g., a non-human antibody, refers to an antibody that has undergone humanization.

The term "hypervariable region" or "HVR" as used herein refers to each of the regions of an antibody variable domain which are hypervariable in sequence ("complementarity determining regions" or "CDRs") and/or form structurally defined loops ("hypervariable loops") and/or contain the antigen-contacting residues ("antigen contacts"). Generally, antibodies comprise six HVRs: three in the VH (H1, H2, H3), and three in the VL (L1, L2, L3). Exemplary HVRs herein include:

(a) hypervariable loops occurring at amino acid residues 26-32 (L1), 50-52 (L2), 91-96 (L3), 26-32 (H1), 53-55 (H2), and 96-101 (H3) (Chothia and Lesk, *J. Mol. Biol.* 196:901-917 (1987));

(b) CDRs occurring at amino acid residues 24-34 (L1), 50-56 (L2), 89-97 (L3), 31-35b (H1), 50-65 (H2), and 95-102 (H3) (Kabat et al., *Sequences of Proteins of Immunological Interest,* 5th Ed. Public Health Service, National Institutes of Health, Bethesda, MD (1991));

(c) antigen contacts occurring at amino acid residues 27c-36 (L1), 46-55 (L2), 89-96 (L3), 30-35b (H1), 47-58 (H2), and 93-101 (H3) (MacCallum et al. *J. Mol. Biol.* 262: 732-745 (1996)); and (d) combinations of (a), (b), and/or (c), including HVR amino acid residues 46-56 (L2), 47-56 (L2), 48-56 (L2), 49-56 (L2), 26-35 (H1), 26-35b (H1), 49-65 (H2), 93-102 (H3), and 94-102 (H3).

Unless otherwise indicated, HVR residues and other residues in the variable domain (e.g., FR residues) are numbered herein according to Kabat et al., supra.

"Framework" or "FR" refers to variable domain residues other than hypervariable region (HVR) residues. The FR of a variable domain generally consists of four FR domains: FR1, FR2, FR3, and FR4. Accordingly, the HVR and FR sequences generally appear in the following sequence in VH (or VL): FR1-H1(L)-FR2-H2(L2)-FR3-H3(L3)-FR4.

The "class" of an antibody refers to the type of constant domain or constant region possessed by its heavy chain. There are five major classes of antibodies: IgA, IgD, IgE, IgG, and IgM, and several of these may be further divided into subclasses (isotypes), e.g., $IgG_1$, $IgG_2$, $IgG_3$, $IgG_4$, $IgA_1$, and $IgA_2$. The heavy chain constant domains that correspond to the different classes of immunoglobulins are called $\alpha$, $\delta$, $\varepsilon$, $\gamma$, and $\mu$, respectively.

The term "Fc domain" or "Fc region" herein is used to define a C-terminal region of an immunoglobulin heavy chain that contains at least a portion of the constant region. The term includes native sequence Fc regions and variant Fc regions. Although the boundaries of the Fc region of an IgG heavy chain might vary slightly, the human IgG heavy chain Fc region is usually defined to extend from Cys226, or from Pro230, to the carboxyl-terminus of the heavy chain. However, antibodies produced by host cells may undergo post-translational cleavage of one or more, particularly one or two, amino acids from the C-terminus of the heavy chain. Therefore an antibody produced by a host cell by expression of a specific nucleic acid molecule encoding a full-length heavy chain may include the full-length heavy chain, or it may include a cleaved variant of the full-length heavy chain (also referred to herein as a "cleaved variant heavy chain"). This may be the case where the final two C-terminal amino acids of the heavy chain are glycine (G446) and lysine (K447, numbering according to Kabat EU index). Therefore, the C-terminal lysine (Lys447), or the C-terminal glycine (Gly446) and lysine (K447), of the Fc region may or may not be present. Unless otherwise specified herein, numbering of amino acid residues in the Fc region or constant region is according to the EU numbering system, also called the EU index, as described in Kabat et al., Sequences of Proteins of Immunological Interest, 5th Ed. Public Health Service, National Institutes of Health, Bethesda, MD, 1991 (see also above). A "subunit" of an Fc domain as used herein refers to one of the two polypeptides forming the dimeric Fc domain, i.e. a polypeptide comprising C-terminal constant regions of an immunoglobulin heavy chain, capable of stable self-association. For example, a subunit of an IgG Fc domain comprises an IgG CH2 and an IgG CH3 constant domain.

A "modification promoting heterodimerization" is a manipulation of the peptide backbone or the post-translational modifications of a polypeptide, e.g. an immunoglobulin heavy chain that reduces or prevents the association of the polypeptide with an identical polypeptide to form a homodimer. A modification promoting heterodimerization as used herein particularly includes separate modifications made to each of two polypeptides desired to form a dimer, wherein the modifications are complementary to each other so as to promote association of the two polypeptides. For example, a modification promoting heterodimerization may alter the structure or charge of one or both of the polypeptides desired to form a dimer so as to make their association sterically or electrostatically favorable, respectively. Heterodimerization occurs between two non-identical polypeptides, such as two immunoglobulin heavy chains wherein further immunoconjugate components fused to each of the heavy chains (e.g. IL-2 polypeptide) are not the same. In the immunoconjugates of the present invention, the modification promoting heterodimerization is in the heavy chain(s), specifically in the Fc domain, of an immunoglobulin molecule. In some embodiments the modification promoting heterodimerziation comprises an amino acid mutation, specifically an amino acid substitution. In a particular embodiment, the modification promoting heterodimerization comprises a separate amino acid mutation, specifically an amino acid substitution, in each of the two immunoglobulin heavy chains.

An "activating Fc receptor" is an Fc receptor that following engagement by an Fc region of an antibody elicits signaling events that stimulate the receptor-bearing cell to perform effector functions. Activating Fc receptors include FcγRIIIa (CD16a), FcγRI (CD64), FcγRIIa (CD32), and FcαRI (CD89).

The term "effector functions" when used in reference to antibodies refer to those biological activities attributable to the Fc region of an antibody, which vary with the antibody isotype. Examples of antibody effector functions include: C1q binding and complement dependent cytotoxicity (CDC), Fc receptor binding, antibody-dependent cell-mediated cytotoxicity (ADCC), antibody-dependent cellular phagocytosis (ADCP), cytokine secretion, immune complex-mediated antigen uptake by antigen presenting cells, down regulation of cell surface receptors (e.g. B cell receptor), and B cell activation.

As used herein, the term "effector cells" refers to a population of lymphocytes that display effector moiety receptors, e.g. cytokine receptors, and/or Fc receptors on their surface through which they bind an effector moiety, e.g. a cytokine, and/or an Fc region of an antibody and contribute to the destruction of target cells, e.g. tumor cells. Effector cells may for example mediate cytotoxic or phagocytic effects. Effector cells include, but are not limited to, effector T cells such as $CD8^+$ cytotoxic T cells, $CD4^+$ helper T cells, γδ T cells, NK cells, lymphokine-activated killer (LAK) cells and macrophages/monocytes.

Antibody-dependent cell-mediated cytotoxicity (ADCC) is an immune mechanism leading to the lysis of antibody-coated target cells by immune effector cells. The target cells are cells to which antibodies or fragments thereof comprising an Fc region specifically bind, generally via the protein part that is N-terminal to the Fc region. As used herein, the term "increased/reduced ADCC" is defined as either an increase/reduction in the number of target cells that are lysed in a given time, at a given concentration of antibody in the medium surrounding the target cells, by the mechanism of ADCC defined above, and/or a reduction/increase in the concentration of antibody, in the medium surrounding the target cells, required to achieve the lysis of a given number of target cells in a given time, by the mechanism of ADCC. The increase/reduction in ADCC is relative to the ADCC mediated by the same antibody produced by the same type of host cells, using the same standard production, purification, formulation and storage methods (which are known to those skilled in the art), but that has not been engineered. For example the increase in ADCC mediated by an antibody produced by host cells engineered to have an altered pattern of glycosylation (e.g. to express the glycosyltransferase, GnTIII, or other glycosyltransferases) by the methods described herein, is relative to the ADCC mediated by the same antibody produced by the same type of non-engineered host cells.

By "antibody having increased/reduced antibody dependent cell-mediated cytotoxicity (ADCC)" is meant an antibody having increased/reduced ADCC as determined by any suitable method known to those of ordinary skill in the art. One accepted in vitro ADCC assay is as follows:

1) the assay uses target cells that are known to express the target antigen recognized by the antigen-binding region of the antibody;
2) the assay uses human peripheral blood mononuclear cells (PBMCs), isolated from blood of a randomly chosen healthy donor, as effector cells;
3) the assay is carried out according to following protocol:
   i) the PBMCs are isolated using standard density centrifugation procedures and are suspended at $5 \times 10^6$ cells/ml in RPMI cell culture medium;
   ii) the target cells are grown by standard tissue culture methods, harvested from the exponential growth phase with a viability higher than 90%, washed in RPMI cell culture medium, labeled with 100 microCuries of $^{51}Cr$, washed twice with cell culture medium, and resuspended in cell culture medium at a density of $10^5$ cells/ml;
   iii) 100 microliters of the final target cell suspension above are transferred to each well of a 96-well microtiter plate;
   iv) the antibody is serially-diluted from 4000 ng/ml to 0.04 ng/ml in cell culture medium and 50 microliters of the resulting antibody solutions are added to the target cells in the 96-well microtiter plate, testing in triplicate various antibody concentrations covering the whole concentration range above;
   v) for the maximum release (MR) controls, 3 additional wells in the plate containing the labeled target cells, receive 50 microliters of a 2% (V/V) aqueous solution of non-ionic detergent (Nonidet, Sigma, St. Louis), instead of the antibody solution (point iv above);
   vi) for the spontaneous release (SR) controls, 3 additional wells in the plate containing the labeled target cells, receive 50 microliters of RPMI cell culture medium instead of the antibody solution (point iv above);
   vii) the 96-well microtiter plate is then centrifuged at $50 \times g$ for 1 minute and incubated for 1 hour at 4° C.;
   viii) 50 microliters of the PBMC suspension (point i above) are added to each well to yield an effector:target cell ratio of 25:1 and the plates are placed in an incubator under 5% $CO_2$ atmosphere at 37° C. for 4 hours;
   ix) the cell-free supernatant from each well is harvested and the experimentally released radioactivity (ER) is quantified using a gamma counter;
   x) the percentage of specific lysis is calculated for each antibody concentration according to the formula (ER-MR)/(MR-SR)×100, where ER is the average radioactivity quantified (see point ix above) for that antibody concentration, MR is the average radioactivity quantified (see point ix above) for the MR controls (see point v above), and SR is the average radioactivity quantified (see point ix above) for the SR controls (see point vi above);
4) "increased/reduced ADCC" is defined as either an increase/reduction in the maximum percentage of specific lysis observed within the antibody concentration range tested above, and/or a reduction/increase in the concentration of antibody required to achieve one half of the maximum percentage of specific lysis observed within the antibody concentration range tested above. The increase/reduction in ADCC is relative to the ADCC, measured with the above assay, mediated by the same antibody, produced by the same type of host cells, using the same standard production, purification, formulation and storage methods, which are known to those skilled in the art, but that has not been engineered.

As used herein, the term "immunoconjugate" refers to a polypeptide molecule that includes at least one effector moiety, such as a cytokine, and an antigen binding moiety, such as an antibody. In certain embodiments, the immunoconjugate comprises not more than one effector moiety. Particular immunoconjugates useful in the invention essentially consist of one effector moiety and an antibody joined by one or more peptide linkers. Particular immunoconjugates according to the invention are fusion proteins, i.e. the components of the immunconjugate are joined by peptide bonds.

The term "monoclonal antibody" as used herein refers to an antibody obtained from a population of substantially homogeneous antibodies, i.e., the individual antibodies comprising the population are identical and/or bind the same epitope, except for possible variant antibodies, e.g., containing naturally occurring mutations or arising during production of a monoclonal antibody preparation, such variants generally being present in minor amounts. In contrast to polyclonal antibody preparations, which typically include different antibodies directed against different determinants (epitopes), each monoclonal antibody of a monoclonal antibody preparation is directed against a single determinant on an antigen. Thus, the modifier "monoclonal" indicates the character of the antibody as being obtained from a substantially homogeneous population of antibodies, and is not to be construed as requiring production of the antibody by any particular method. For example, the monoclonal antibodies to be used in accordance with the present invention may be made by a variety of techniques, including but not limited to the hybridoma method, recombinant DNA methods, phage-display methods, and methods utilizing transgenic animals containing all or part of the human immunoglobulin loci, such methods and other exemplary methods for making monoclonal antibodies being described herein.

As used herein, the terms "first", "second", "third" etc. with respect to antigen binding moieties etc., are used for convenience of distinguishing when there is more than one of each type of moiety. Use of these terms is not intended to confer a specific order or orientation unless explicitly so stated.

By "fused" is meant that the components (e.g. a Fab molecule and an Fc domain subunit) are linked by peptide bonds, either directly or via one or more peptide linkers.

"Carcinoembryonic antigen" or "CEA" (also known as Carcinoembryonic antigen-related cell adhesion molecule 5 (CEACAM5)) refers to any native CEA from any vertebrate source, including mammals such as primates (e.g. humans), non-human primates (e.g. cynomolgus monkeys) and rodents (e.g. mice and rats), unless otherwise indicated. The term encompasses "full-length," unprocessed CEA as well as any form of CEA that results from processing in the cell. The term also encompasses naturally occurring variants of CEA, e.g., splice variants or allelic variants. In one embodiment, CEA is human CEA. The amino acid sequence of human CEA is shown in UniProt (www.uniprot.org) accession no. P06731, or NCBI (www.ncbi.nlm.nih.gov/) RefSeq NP_004354.2.

"Fibroblast activation protein" or "FAP" (also known as seprase) refers to any native FAP from any vertebrate source, including mammals such as primates (e.g. humans), non-human primates (e.g. cynomolgus monkeys) and rodents (e.g. mice and rats), unless otherwise indicated. The term encompasses "full-length," unprocessed FAP as well as any form of FAP that results from processing in the cell. The term also encompasses naturally occurring variants of FAP, e.g., splice variants or allelic variants. In one embodiment, FAP is human FAP. The amino acid sequence of human FAP is shown in UniProt (www.uniprot.org) accession no. Q12884, or NCBI (www.ncbi.nlm.nih.gov/) RefSeq NP_004451.2.

DETAILED DESCRIPTION

Described herein is an integrated modeling platform to quantify the impact of drug elimination caused by target expansion on the uptake of the drug by the target tissue (e.g. tumor). This model allows optimal dosing regimens to be calculated for either a population of individuals (e.g. for a universal dosing regimen) or for single individuals (e.g. for a personalised dosage regimen).

Mixed-Effect Modeling Techniques

In the present context, mixed-effect modelling technique[4] allows to analyze data from multiple individuals (a population) to characterize variability in the dynamic processes under investigation (e.g. antibody tumor uptake) and to provide information about the dynamic of this process for each single individual using the information at the population level. Briefly, this modelling process comprises two steps. In the first step, a likelihood function is minimized to estimate the mean values of the model parameters as well as their interindividual variability throughout the population. The resulting estimates are called "population parameters". In the second step, information on the population parameters is used to estimate the best model parameters for each individual on the basis individual information. These parameters are called "individual parameters." The Monolix software (Lixoft)[5], on the basis of the stochastic approximation of the expectation-maximization algorithm, was used to estimate the population and individual parameters.

In their general form, mixed-effect models can be written as follows:

$$y_{ij}=f(x_{ij},\phi_i)+g(x_{ij},\phi_i)\varepsilon_{ij};\ 1\leq i\leq N;\ 1\leq j\leq n_i$$

Where N is the number of individuals, $n_i$ the number of observations for individual i, x the regression variable (e.g. time), and y the observations (e.g. drug concentration in plasma). The term f is the structural model. The residual error model is written $g(x_{ij},\phi_i)\varepsilon_{ij}$, where $\varepsilon_{ij}\sim N(0,\sigma^2)$. The individual parameters ($\phi_i$) can be defined as follows:

$$\phi_i=h(\mu+\eta_i),\eta_i\sim N(0,\Omega), i=1,\ldots,N$$

Where μ is a p-vector of fixed population parameter (i.e. h(μ) is the median value across individuals for each of the p parameters), $\eta_i$ is a p-vector or random effects, Ω is the p×p variance-covariance matrix of the random effects and h is some predefined transformation. Here it is assumed that the individual parameters are log-normally distributed (i.e. $h(\mu)=e^\mu$).

The unknown set of parameters in the model is then:

$$\eta=(\mu,\Omega,\sigma^2)$$

For the models provided herein, the general formulation was extended to multi-response models as the inventors analyzed several variables dynamic simultaneously (e.g. drug concentration and immune cell number in plasma, drug concentration and drug uptake imaging data). In this case, the global likelihood function is the unbalanced sum of all likelihood functions written for each observation.

Parameter Estimates

From data collected from clinical trials, the inventors have provided parameter values for the PKPD model in accordance with the invention. These parameters values are preferably $k_{clear}$ has a value between 0.02 and 0.04 hour$^{-1}$;
$k_{on}$ has a value between 0.26 and 4.5 μM$\cdot^{-1}$ h$^{-1}$;
$k_{off}$ has a value between 0.0035 and 0.02 h$^{-1}$,
$k_{in}$ has a value between 0.0006 and 0.0144 μM·h$^{-1}$;
$k_{out}$ has a value between 0.0018 and 0.069 h$^{-1}$,
$k_{int}$ has a value between 0.0066 and 0.023 h$^{-1}$; and
η has a value between 1.02 and 3.31.

In some embodiments:

$k_{clear}$ is a value between 0.025 and 0.035 hour$^{-1}$;
$k_{on}$ is a value between 1 and 3.5 μM$\cdot^{-1}$ h$^{-1}$;
$k_{off}$ is a value between 0.006 and 0.018 h$^{-1}$,
$k_{in}$ is a value between 0.002 and 0.0035 μM·h$^{-1}$;
$k_{out}$ has a value between 0.005 and 0.02 h$^{-1}$,
$k_{int}$ has a value between 0.01 and 0.02 h$^{-1}$; and
η has a value between 1.5 and 2.0.

In some embodiments:

$k_{clear}$ is 0.0307 hour$^{-1}$ in the mean of the population (std. dev.=0.06);
$k_{on}$ is 1.09 μM$\cdot^{-1}$ h$^{-1}$ in the mean (std. dev.=0.467);
$k_{off}$ is 0.0061 h$^{-1}$ in the mean (std. dev.=0.177),
$k_{in}$ is 0.0029 μM·h$^{-1}$ in the mean (std. dev.=0.53);
$k_{out}$ is 0.011 h$^{-1}$ in the mean (std. dev.=0.606),
$k_{int}$ is 0.012 h$^{-1}$ in the mean (std. dev.=0.205); and
η is 1.84 in the mean (std. dev.=0.196).

The parameters for the model provided herein are provided as a value within a range. These ranges are based on detailed analysis of clinical trial data. There are several aspects that should be considered and which may lead to differences in parameter estimates, such as e.g. the number of patients the analysis is based on, or the software used.

A comparison between parameter estimates obtained with different software and based on different database sizes is shown below. Different parameterizations were used, the bold italic indicates derived parameters to allow comparison between the two. Different software were used (monolix and nonmem) for the First Analysis and for the Second Analysis.

| | First Analysis<br>74 patients<br>Monolix software | Second Analysis<br>105 patients<br>NONMEM software |
|---|---|---|
| V | 3.43 | 3.21 |
| $k_{clear}$ | 0.0307 | *0.02956* |
| CL | *0.105* | 0.0949 |
| kd | *0.005596* | 0.0057 |
| $k_{on}$ | 1.09 | *3.070* |
| $k_{off}$ | 0.0061 | 0.0175 |
| $k_{in}$ | 0.00294 | *0.00309* |
| Rbas | *0.265* | 0.372 |
| $k_{out}$ | 0.0111 | 0.0083 |
| $k_{int}$ | 0.0122 | 0.0123 |
| η | 1.84 | 1.62 |
| b | 0.351 | 0.363 |

Variability terms are not included in the comparison. Fewer variability terms are estimated with NONMEM compared to Monolix, which is a common difference between the two software.

Modeling Antibody Tumor Uptake

A major limitation to greater efficacy of therapeutic antibody is poor distribution in vivo. The large size of these molecules, combined with the abnormal physiology of tumors causes slow and heterogeneous uptake. As a major consequence, tissue distribution of antibodies occurs slowly, often in insufficient therapeutic amounts. Characterizing the time course of antibody tissue uptake is absolutely critical to determine when to take images or to deliver a secondary reagent in the context of pre-targeted therapeutic strategies. Recently, Schmidt, Wittrup and Thurber have proposed a mathematical framework to describe antibody tissue penetration[6,7]. The general framework is represented in FIG. 1.

In the model as represented in FIG. 1, three processes are described as fundamental:

1. Vascular extravasation and diffusion: Several factors must be taken into account, e.g. vascularized tumors have a network of poorly formed vessels, more permeable than normal capillaries, and characterized by a high interstitial fluid pressure. Once antibodies exit the blood vessel, they face a variety of other transport barriers hampering their diffusion within the tissue (e.g. extracellular matrix, cell density, . . . ).

To model this process, a hypothesis is formulated according to which antibody extravasation across the vasculature is the slowest and therefore rate limiting process due to the low permeability of the vasculature. The tumor interstitial space is described by a series of small and large circular cylindral pores called Krogh cylinder. To calculate the amount of drug that extravasates from the blood vessels and diffuses into the tissue, it is important to consider three factors:

a. the ratio of the capillary surface to the volume of the Krogh cylinder $$\frac{S}{V} = \frac{2\pi R_{Cap} L}{\pi R_{Kgrogh}^2 L} = \frac{2 R_{Cap}}{R_{Kgrogh}^2}$$

b. The permeability across capillary vessels denoted P
  c. The available volume fraction denoted ε

The available volume fraction denotes the interstitial space divided by the total tumor volume.

Following this process, the amount of antibody in tumor is governed by the following differential equation:

$$\frac{d[Ab]_{total}^T}{dt} = \frac{2 \cdot P \cdot R_{Cap}}{R_{Kgrogh}^2}\left([Ab]_{free} - \frac{[Ab]_{free}^T}{\varepsilon}\right)$$

wherein $[Ab]_{free}$ stands for the antibody concentration in plasma and $[Ab]_{free}^T$ is the concentration of antibody free of binding in the tumor tissue. Note that the volume fraction a can be estimated from literature in vitro and in vivo in mice (e.g. for an IgG, it is typically between 0.3 and 0.5)[6]. Permeability can also be calculated from in vivo xenograft experimental data reported in literature. Schmidt and Wittrup have proposed an empirical formula to calculate permeability as a function of compound molecular size[6]. As an example, for CEA-IL2v (160 kDa), the permeability P through capillaries is estimated at 3.78e-7 cm/s.

2. Binding of the antibody to the antigen: Antibody binds to a tumor antigen, with a different timescale as compared to vascular transport and extravasation (order of seconds)

The modelling of the process of therapeutic binding to the antigen relies on three main hypotheses.

a. Antibody binding occurs quickly (seconds), thus a local equilibrium between free and bound antibody is reached in the tissue
  b. Internalization occurs on a slower time scale (minutes to hours), this is assumed to not affect the local equilibrium
  c. The tumor is not saturated, therefore the concentration of antigen in the tumor is greater than the concentration of antibody In consequence, the relative amounts of bound and free Ab depend on the Ab dissociation constant, antigen concentration and available volume fraction:

$$[Ab]_{free} \equiv \left(\frac{K_d}{\left(\frac{[Ag]}{\varepsilon}\right) + K_D}\right)[Ab]_{total}$$

$$[Ab]_{bound} \equiv \left(\frac{\frac{[Ag]}{\varepsilon}}{\left(\frac{[Ag]}{\varepsilon}\right) + K_D}\right)[Ab]_{total}$$

where [Ag] denotes the concentration of antigen in tissue and $K_D$ the dissociation constant.

3. Internalization and elimination: Increased affinity results in greater internalization and degradation Finally, by assuming that the loss of signal from internalization and degradation is governed by a first order process, the equation becomes:

$$\frac{d[Ab]_{total}}{dt} = \frac{2 \cdot P \cdot R_{Cap}}{R_{Kgrogh}^2}\left([Ab]_{plasma} - \frac{[Ab]_{free}}{\varepsilon}\right) - k_e[Ab]_{bound}$$

Development of the Modeling Platform

The development of the modeling platform was done through the analysis of clinical data collected during the first stage of the clinical development of CEA-IL2v. Overall, this dataset included:

1. Peripheral pharmacokinetic: CEA-IL2v concentration in plasma—measured at different time points—in 74 cancer patients receiving CEA-IL2v Q2W or QW were used to develop the model. Overall, this represents 824 observations (11.14 observations on average per patient).

2. Peripheral pharmacodynamic: Immune cell kinetics data in peripheral blood (CD8+, CD4+ T cells, NK and B cells) from 74 patients treated with CEA-IL2v Q2W or QW were used for model development. Overall, 273 evaluations were used (3.69 on average per patient).

3. Imaging uptake: Patients with advanced and/or metastatic solid CEA-positive (CEA+) or CEA-negative (CEA-) tumors were eligible for an imaging sub-study of an ongoing Phase I trial. CEA-IL2v was administered intravenously q2W at a total dose of 6, 20 or 30 mg (including approx. 50 MBq of $^{89}$Zr-CEA-IL2v). All patients underwent up to three $^{89}$Zr-PET assessments during cycle 1 (i.e. within the two weeks after the first CEA-IL2v administration), while a subset of patients underwent additional $^{89}$Zr-PET assessment 6 weeks after the first $^{89}$Zr-PET. Overall, data for 14 patients (6 mg (4 pts CEA+; 3 pts CEA-) or 30 mg (4 pts CEA+; 3 pts CEA-)) were analyzed—per protocol—at three time points (day 1, 4, 8). Overall, a total of 38 uptake evaluations were used for model building (2.71 evaluations on average per patient). Data from patients treated with 20 mg (total n=8) were used as external patients for validation analysis, including those patients that underwent additional $^{89}$Zr-PET assessment 6 weeks after the first $^{89}$Zr-PET First, a PKPD model was developed to analyze simultaneously the CEA-IL2v concentration and immune cell data. Following the approach described by Gibiansly and Gibiansly[8], the inventors developed the following model:

$$\frac{d[Ab]_{free}}{dt} = -k_{clear} \cdot [Ab]_{free} - (k_{on} \cdot [Ab]_{free} \cdot [IL2R]_{free} - k_{off} \cdot [Complex])$$

$$\frac{d[IL2R]_{free}}{dt} = k_{in} - k_{out} \cdot [IL2R]_{free} -$$

$$(k_{on} \cdot [Ab]_{free} \cdot [IL2R]_{free} - k_{off} \cdot [Complex]) + \eta \cdot k_{int} \cdot [Complex]$$

$$\frac{d[Complex]}{dt} = k_{on} \cdot [Ab]_{free} \cdot [IL2R]_{free} - k_{off} \cdot [Complex] - k_{int} \cdot [Complex]$$

Where $[Ab]_{free}$ is the concentration of unbound therapeutic agent in plasma, $[IL2R]_{free}$ is the concentration of unbound immune cells expressing IL2 receptors (IL2R+ cells) in blood and [Complex] is the concentration of complex between therapeutic agent and IL2R+ cells. $k_{clear}$ stands for the constant rate of elimination of therapeutic agent from plasma; $k_{on}$ is an association rate of the complex between therapeutic agent and IL2R+ cells; $k_{off}$ a dissociation rate of the complex between therapeutic agent and IL2R+ cells, $k_{in}$ a constant influx rate of IL2R+ cells in plasma; $k_{out}$ a natural decay rate of IL2R+ cells in plasma, $k_{int}$ the internalization rate of the therapeutic agent and $\eta$ a constant rate of expansion of IL2R+ cells in plasma as a result of the binding (internalization) of the therapeutic agent.

These parameters were estimated through mixed-effect modelling techniques by simultaneously fitting peripheral PK and PD information.

The PKPD-Uptake Coupling Model

Secondly the model was extended to incorporate the uptake process. A last equation was then added:

$$\frac{d[Ab]_{total}}{dt} = \frac{2 \cdot P \cdot R_{Cap}}{R_{Kgrogh}^2}\left([Ab]_{plasma} - \left(\frac{Kd}{\left(\frac{[Ag]}{\varepsilon}\right) + K_d}\right)\frac{[Ab]_{total}}{\varepsilon}\right) -$$

$$k_e\left(\frac{\frac{[Ag]}{\varepsilon}}{\left(\frac{[Ag]}{\varepsilon}\right) + K_d}\right)[Ab]_{total}$$

Following the assumption that tumor uptake does not impact peripheral PK, the inventors fixed all parameters related to peripheral PK to the population values reported above and analyzed simultaneously the peripheral PK and uptake imaging data from an imaging substudy with $^{89}$Zr-radiolabeled CEA-IL2v.

Figure 2:
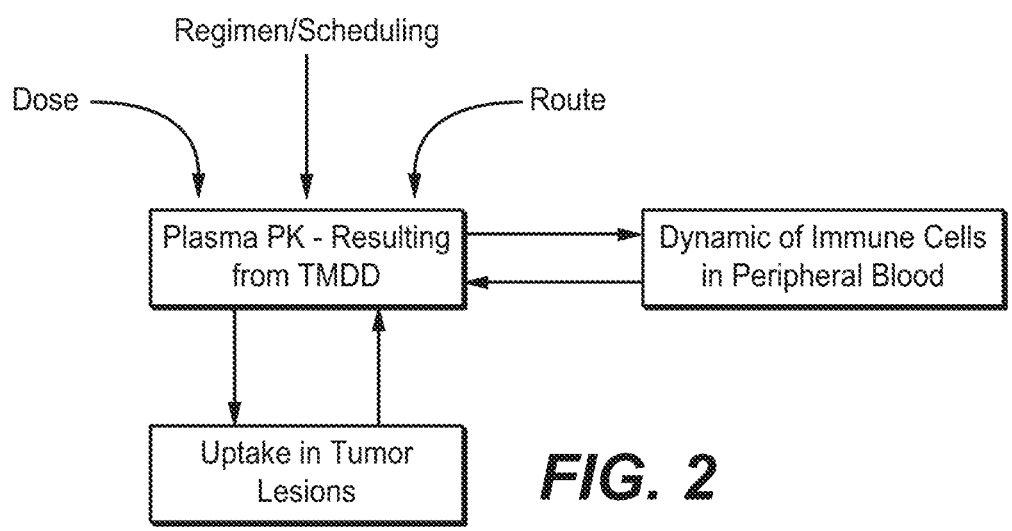
FIG. 2: Schematic representation of the processes by which the modelling framework is used. The presented model can be simulated to evaluate the impact of dose, scheduling and route of administration on tumor uptake.

Overall the PKPD—uptake coupling model allows the user to evaluate the impact of doses, route of administration, and scheduling on the tumor uptake. FIG. 2 proposes a diagram illustrating the process by which the model can be used.

Figure 3A:
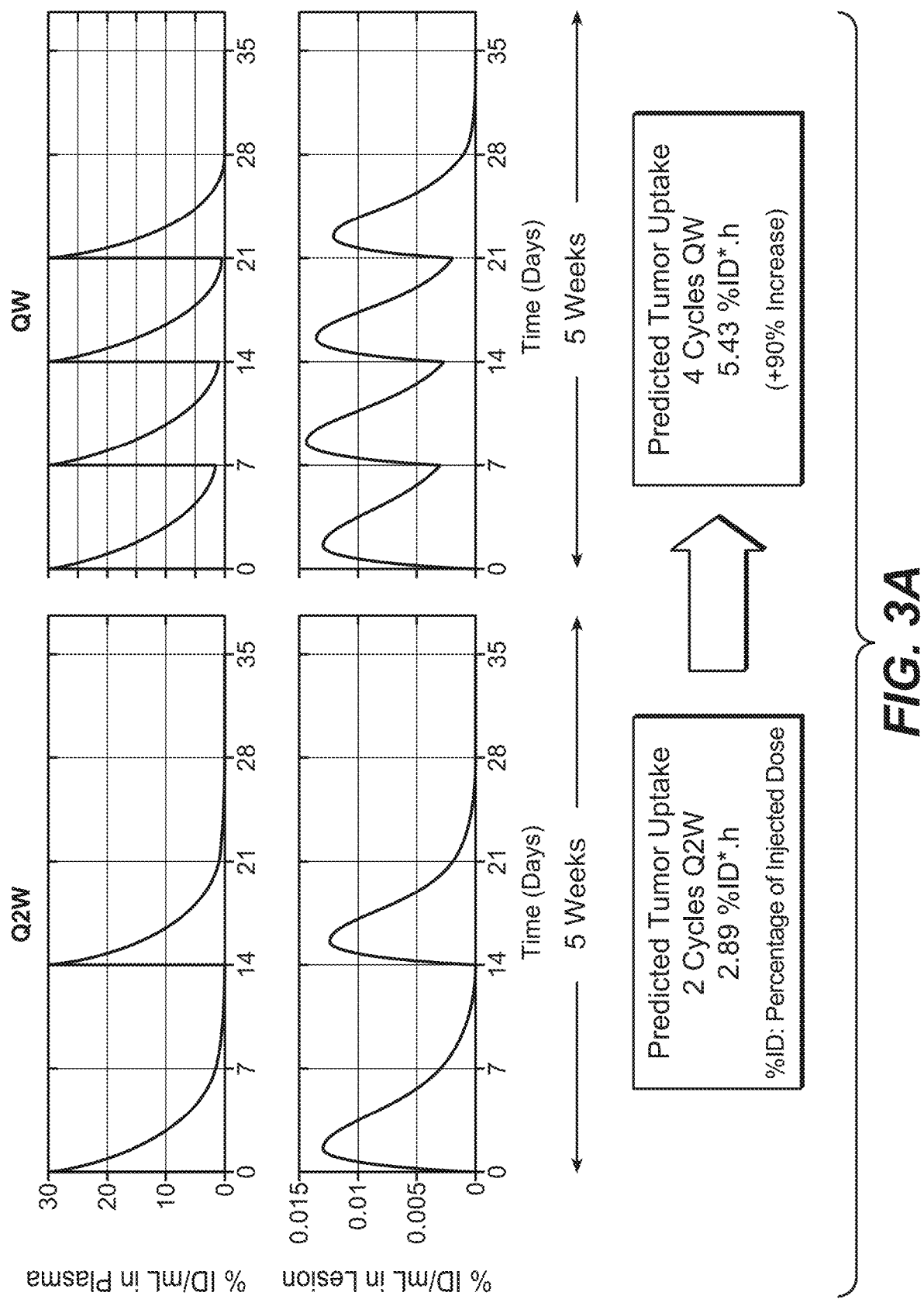
FIG. 3A: Comparison of Q2W and QW regimen. In the absence of expansion of IL2R expressing cells in the blood, giving twice more drug (QW) would theoretically result in doubling tumor uptake (+100% with respect to Q2W). Model simulations indicate that the actual expansion of IL2R expressing cells in QW negatively affects the uptake which, nevertheless, still reaches+90% increase with respect to Q2W.
Figure 3C:
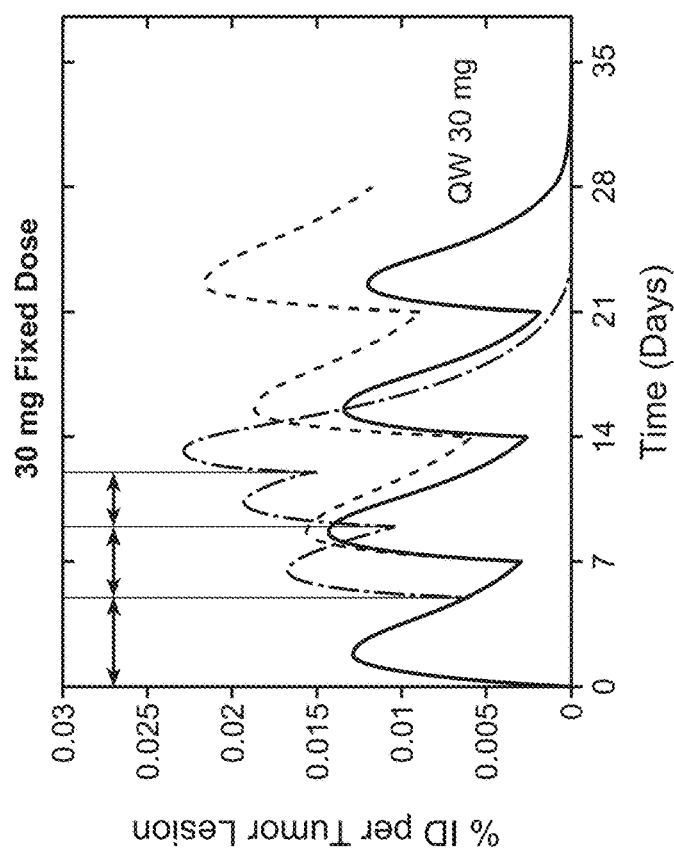
FIG. 3B and FIG. 3C: Increasing the dose at each cycle (upper solid curve, FIG. 3B) or shortening the time interval between cycles (upper solid curve, FIG. 3C) can compensate for the reduction of tumor uptake due to expansion of IL2R expressing cells (lower solid curves, FIG. 3B and FIG. 3C), resulting in tumor uptake as predicted for the absence of expansion of IL2R expressing cells (dashed curves, FIG. 3B and FIG. 3C).
Figure 3B:
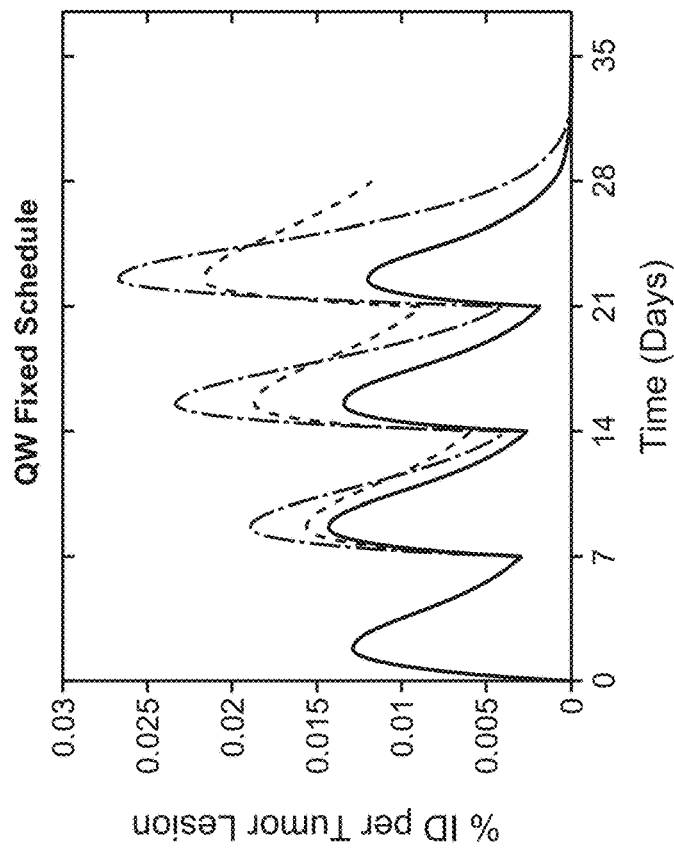
Figure 4:
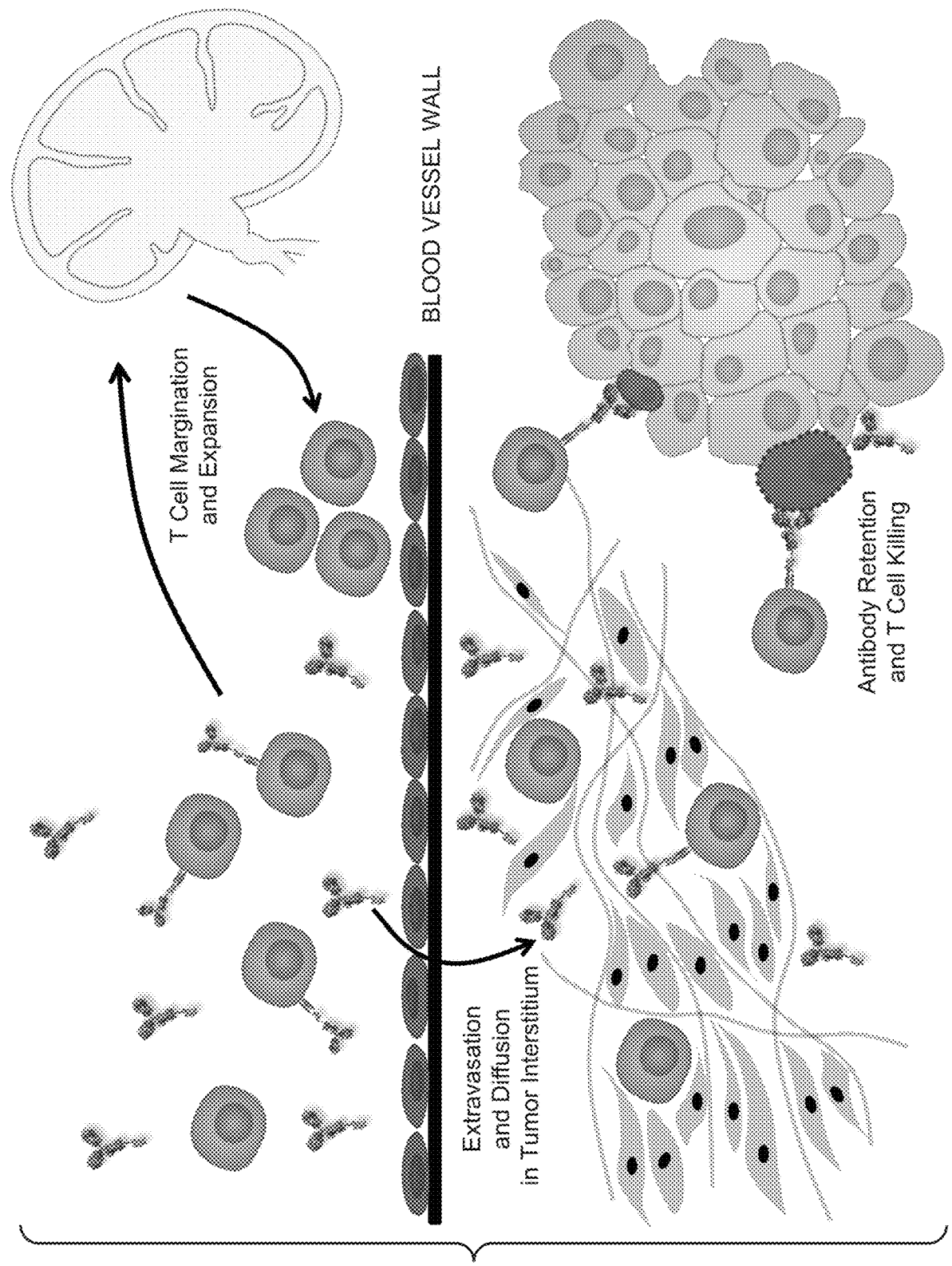
FIG. 4: Schematic view of the model developed to integrate simultaneously CEA-IL2v peripheral pharmacokinetic and tumor uptake data. The mathematical model is written as ordinary differential equations and describes the two main simultaneous processes. First part (upper part) shows the binding of the therapeutic antibody to immune cells in periphery with subsequent cell margination hypothetically resulting into expansion of drug target. Second part (lower part) shows antibody extravasation, diffusion, and binding to tumor CEA antigen to mediate T cell cytotoxicity.
Figure 5A:
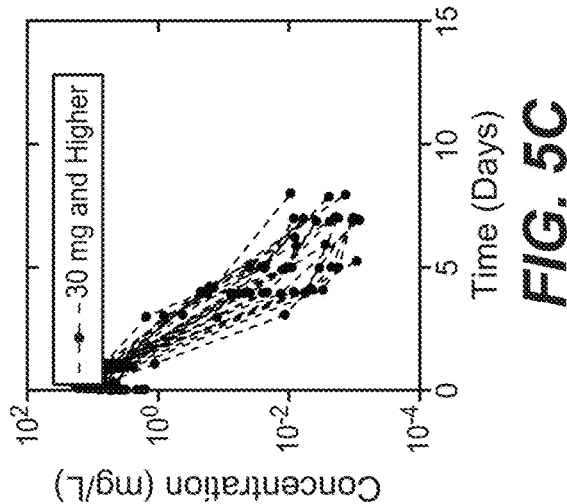
FIG. 5A, FIG. 5B, FIG. 5C, FIG. 5D, FIG. 5E: Summary of CEA-IL2v pharmacokinetic and uptake imaging data.
Figure 5B:
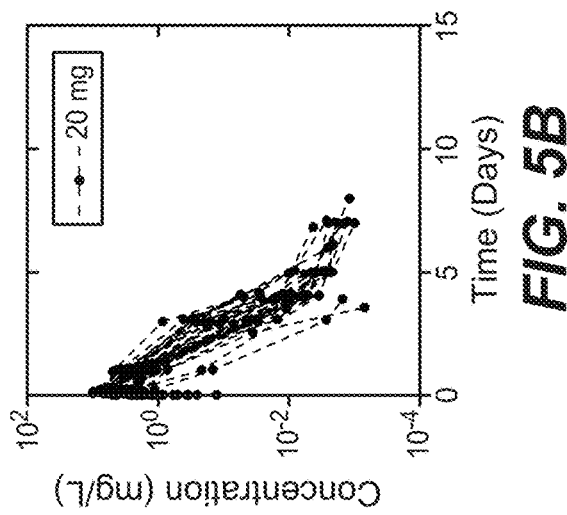
Figure 5C:
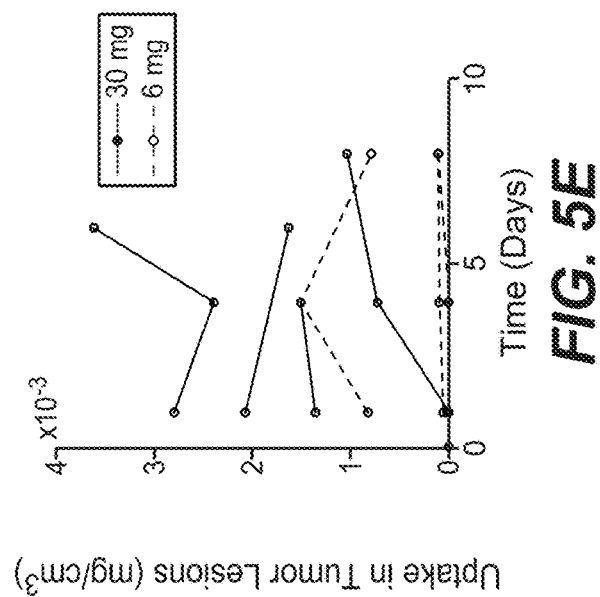
Figure 5D:
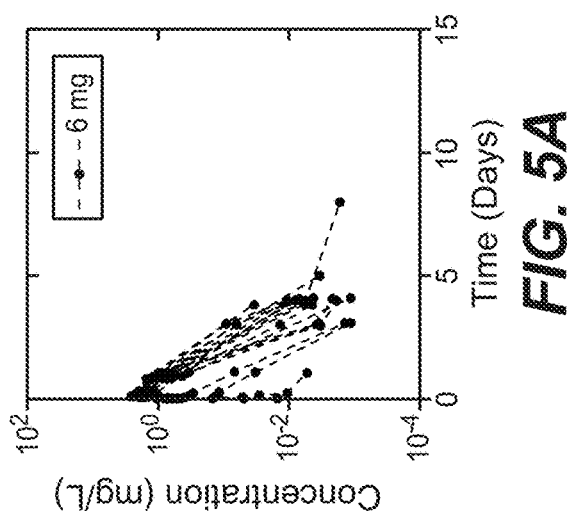
Figure 5E:
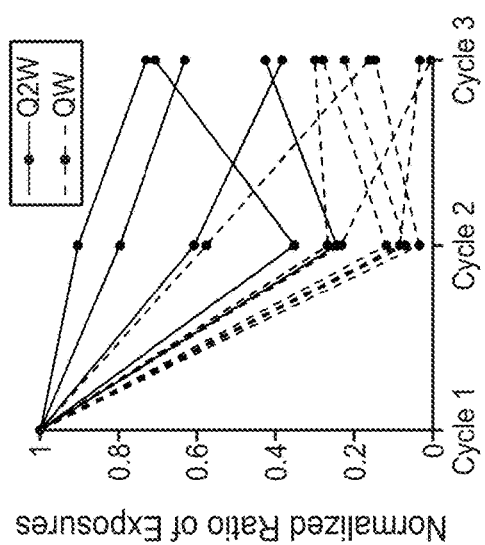
Figure 6A:
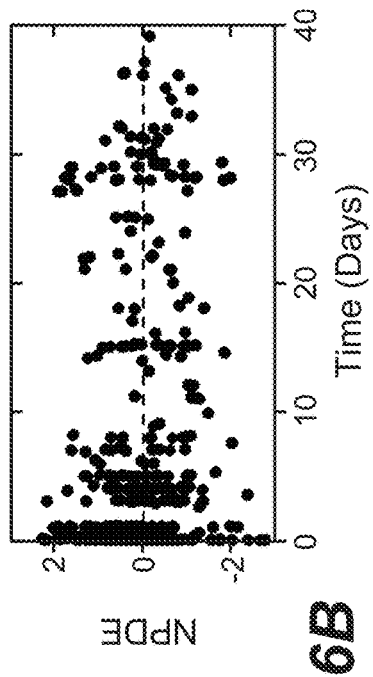
Figure 6B:
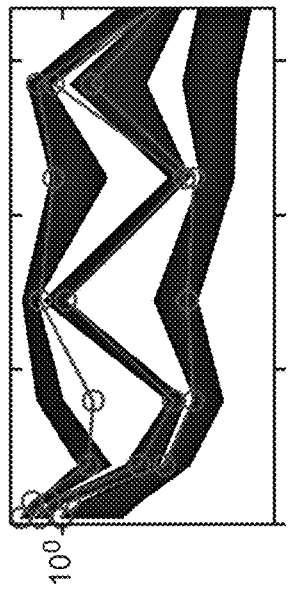
Figure 6D:
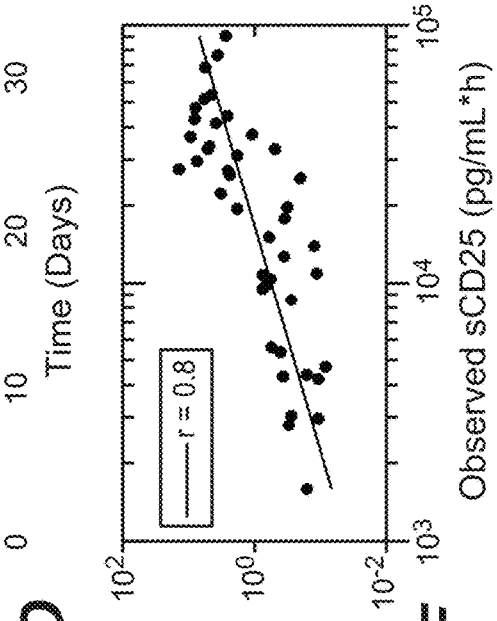
Figure 6C:
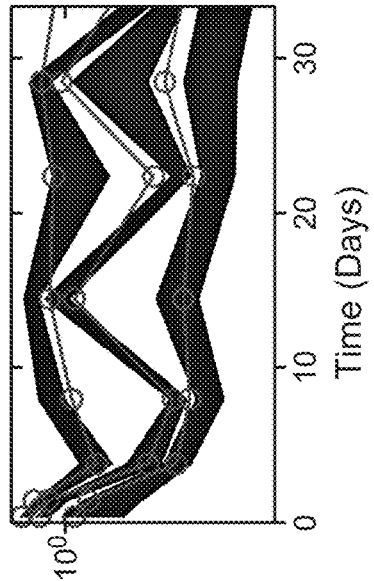
Figure 6E:
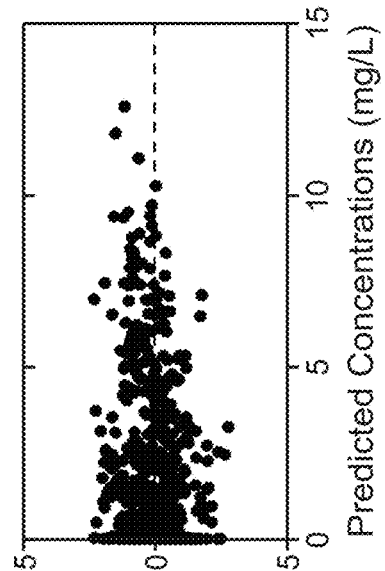
Figure 6F:
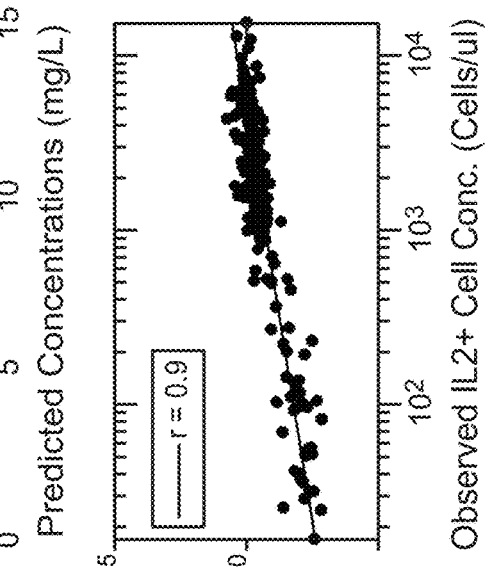
Figure 7A:
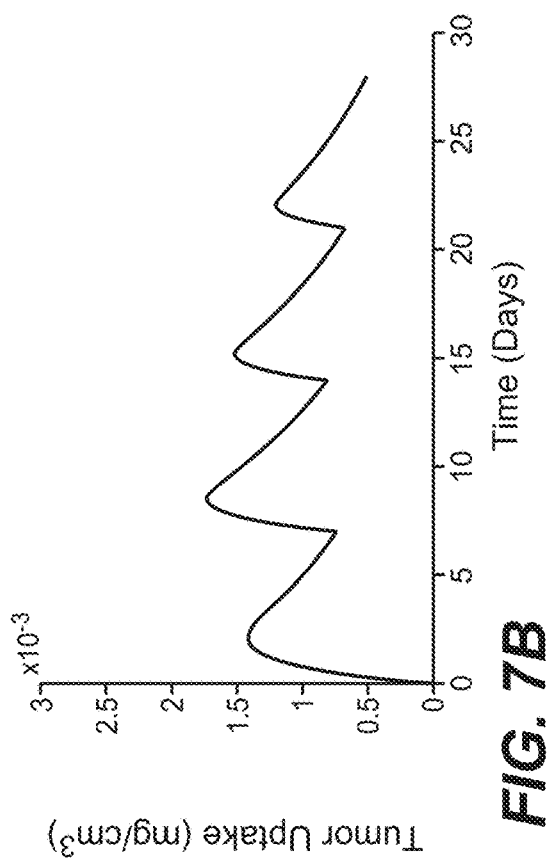
FIG. 7A, FIG. 7B, FIG. 7C, FIG. 7D: Exploration, by means of model simulations, of the impact of dosing regimen on CEA-IL2v tumor uptake.
Figure 7B:
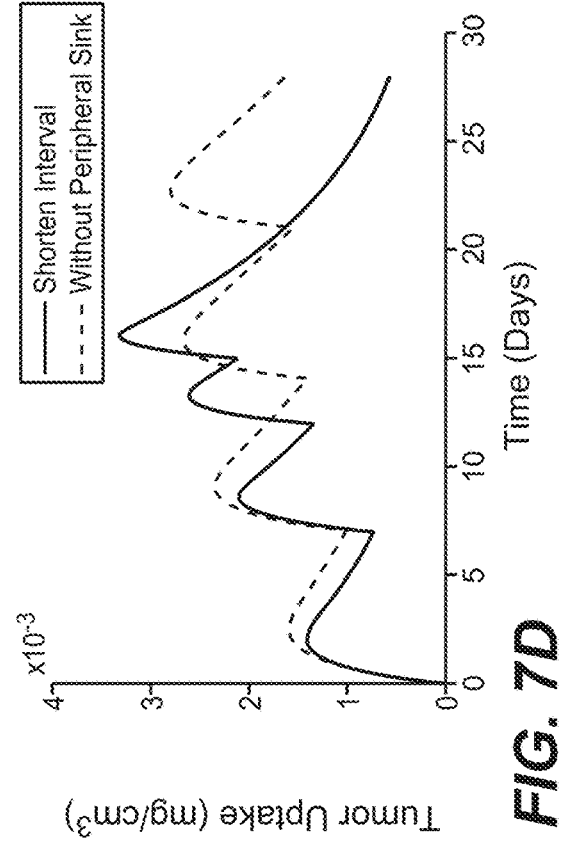
Figure 7C:
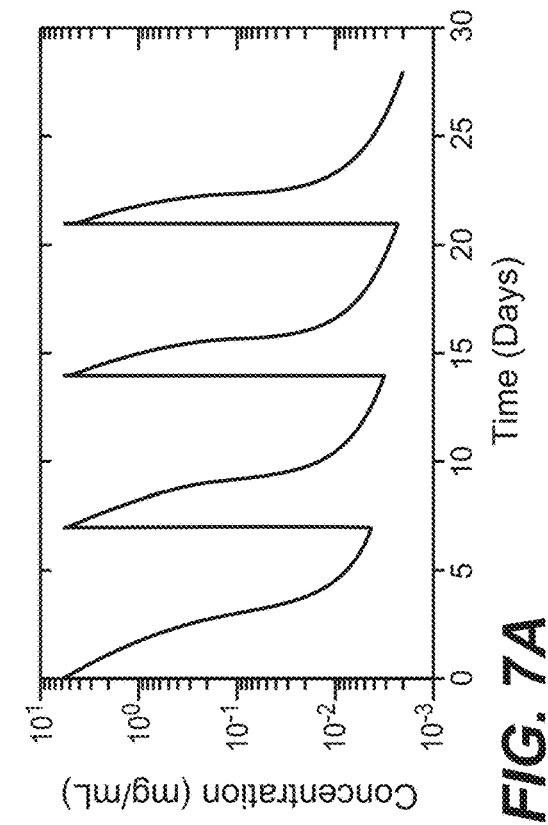
Figure 7D:
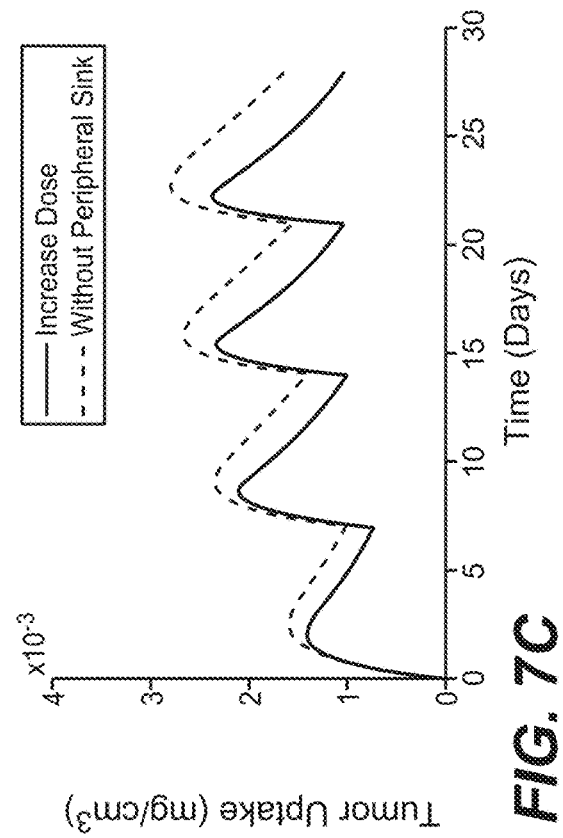
Figure 9:
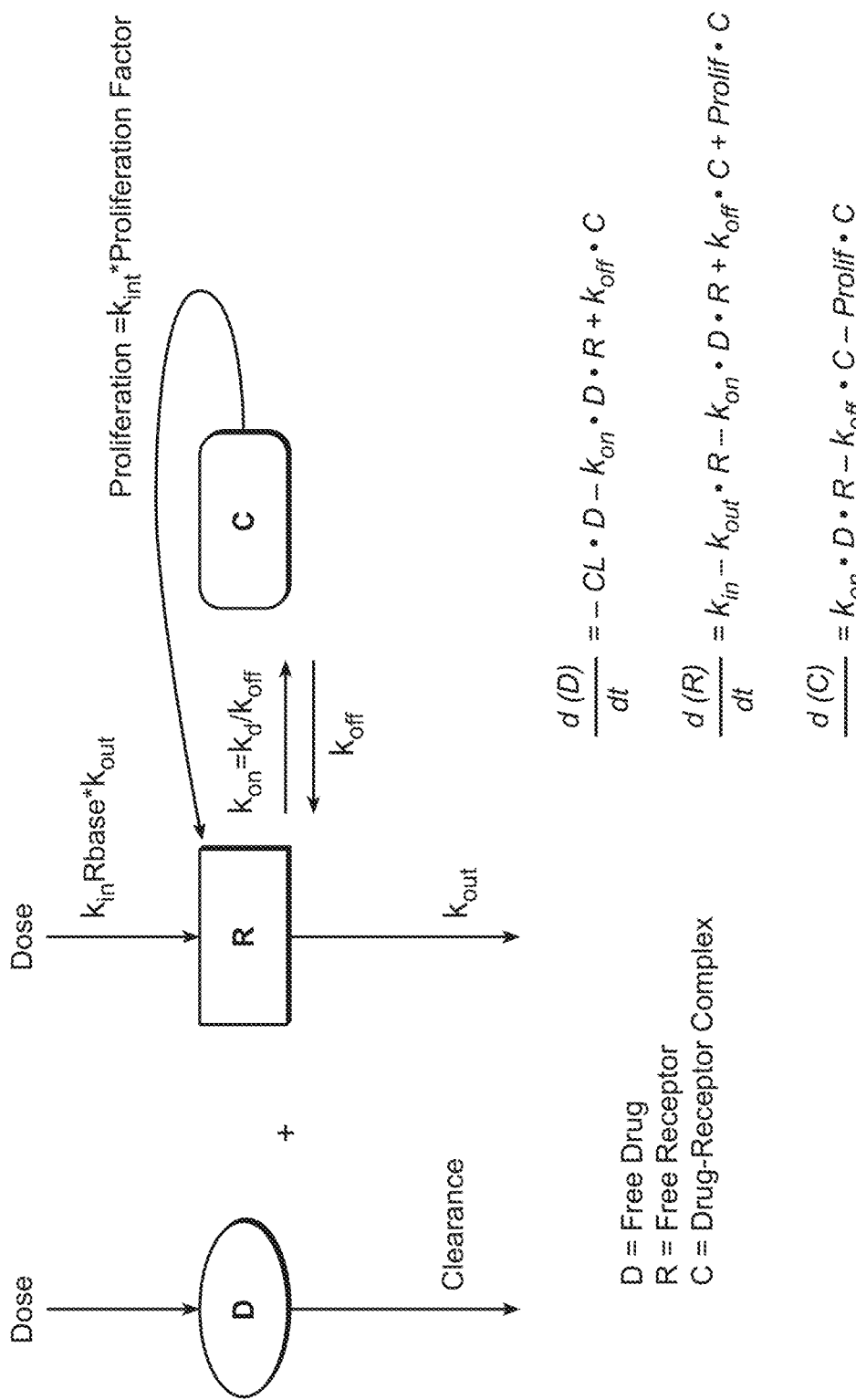
FIG. 9: Schematic for the model for CEA-IL2v and the equations. D=Free drug (equivalent to $[Ab]_{free}$); R=Free receptor (equivalent to $[IL2R]_{free}$); and C=Drug-receptor complex (equivalent to [Complex]).

The model is currently applied to select a dosing regimen based on its ability to increase tumor uptake. As intensification of the dosing regimen will lead to expansion of IL2R+ cells in periphery, it is not straightforward to determine how much a dosing regimen should be intensified to increase tumor uptake. The model allows the user to calculate how much the compound dose should be increased and/or by what the time interval between doses should be reduced to compensate for expansion of IL2R+ cells in the periphery and achieve optimal tumor uptake (see FIG. 3A, FIG. 3B, FIG. 3C).

Pharmacokinetic Data

Pharmacokinetic (PK) data often includes parameters such as clearance, bioavailability, and elimination half-life. In the present case, therapeutic agent concentration is measured in a biological sample obtained from an individual following dose administration of the therapeutic agent. The biological sample may be selected from plasma, serum, saliva, urine and even tissue. Preferably the sample is blood or serum. The PK data particularly includes the concentration of unbound therapeutic agent in blood, serum or plasma (particularly plasma).

Analysis of the sample is usually carried out in a clinical chemistry laboratory or by a clinical pharmacokinetics laboratory. A variety of clinical techniques are available for drug measurement, such as high-pressure liquid chromatography (HPLC) optionally coupled with mass spectrometry (LCMS); immunoassay, ELISA, Fluorescence-activated cell sorting (FACS), flow cytometry and other techniques known in the art.

The methods used by the analytic laboratory may depend on such factors as the physicochemical characteristics of the therapeutic agent, target therapeutic drug concentration, amount (volume) and nature of the sample (serum, urine, saliva etc.).

After the serum or plasma concentrations of the therapeutic agent are measured, the data must be evaluated. This may require a report on the total concentration of therapeutic agent (i.e. free therapeutic agent and bound therapeutic agent) as well as the concentration of free therapeutic agent and the concentration of bound therapeutic agent (complex). This assay data may be applied to the PKPD model of the invention in order to quantify the predicted reduction in free therapeutic agent and a dosage regimen may be designed to compensate for this reduction.

Pharmacodynamic Data

Pharmacodynamic data includes considerations of biochemical and physiological effects of the therapeutic agent on the body. For IL2-based therapeutic agents measurements include immunological components that may interact (be a target for) the therapeutic agent (drug-receptor interaction). Such immunological components include IL2R+ cells such as CD8+ and CD4+ T cells, NK cells and B-cells. The PD data particularly includes the concentration of immune cells expressing IL-2R in blood.

The concentration of such immunological components may be determined using techniques such as FACS analysis. It is further proposed that the concentration of these components could be determined by measuring the level of soluble CD25.

The pharmacodynamics data analyses in the periphery described herein are currently limited to enumeration of immune cell numbers. It is envisaged that specific subpopulations of those immune cells, e.g. memory NK cells or memory T cells, or Th17 cells, etc. may be discriminated. Further, functional parameters of those cells like intracellular cytokine or effector molecule production (i.e. IFNγ, TNFα, IL2, Grzm A/B, etc.) may be of value. Additionally, there is the possibility that measuring a number of plasma cytokines will identify a robust association between a plasma cytokine, immune cells, PK, Exposure, or response to therapy. For example, it might be that the TMDD effect size is coupled to a specific cytokine profile that governs the target cells or vice versa. In a similar way, other circulating factors such as metabolites, exosomes, DNA or RNA molecules could be predictors of TMDD and immune cell proliferative potential.

Imaging Data

It may be useful to know the amount of therapeutic agent that is taken up by the therapeutic target tissue, e.g. tumor. This information can be obtained by administering a labelled version of the therapeutic agent, e.g. radio labelled, and measuring the concentration of therapeutic agent taken up into the therapeutic target tissue over one or more time points. For example an isotopically-labelled therapeutic agent could be administered and its uptake into the target tissue (e.g. tumor) may be determined using techniques such as mass spectrometry. Other techniques include using C-14 labelled therapeutic agent and accelerator mass spectrometry (AMS) to measure the uptake into the therapeutic target tissue. Other labelling techniques are available in the art, for example fluorescent labelling. Any functional in vivo imaging, independent of the nature of the tracer may be used. For example, ultrasound with the use of resonance tracers, X-ray/CT with radiodense tracers, MRI with ferromagnetic tracers, szintigraphy, PET, SPECT with gamma emitting tracers, or photo detectors with photon emitting tracers.

Sampling and Time Intervals

Measurement of drug and metabolite concentrations (levels) in blood, serum or plasma is the most direct approach to assessing pharmacokinetics and pharmacodynamics of the therapeutic agent in an individual. Whole blood contains cellular elements including red and white blood cells, platelets, and various other proteins such as albumins and globulins. It is preferable to use blood samples from the individuals being treated to measure pharmacodynamic data for the PKPD model of the invention. For PK data it is preferable to use serum or plasma samples. To obtain serum, whole blood is allowed to clot and the serum is collected from the supernatant after centrifugation. Plasma is obtained from the supernatant of centrifuged whole blood to which an anticoagulant, such as heparin, has been added. As a result, the protein content of plasma and serum is not the same. Plasma perfuses all of the tissues of the body, including cellular elements in blood. Changes in therapeutic agent concentration in plasma will be reflective of changes in tissue concentration of the therapeutic agent.

Determining unbound therapeutic agent concentration as compared to bound (e.g. to IL2R+ cells) therapeutic agent may be achieved using various bioanalytical techniques. Cell-bound IL2v may be measured in the cellular compartment of the blood. Usually, IL2v would be internalized quickly once it is bound to the receptor. Unbound IL2v would be found in the plasma fraction of the blood and can easily be measured e.g. by ELISA.

In respect of all aspects of the invention, samples may be obtained from the individual(s) at one or more time points following a dose administration of the therapeutic agent to the individual. It is preferable that PK and PD data are collected following the initial (first) dose administration, but data may be collected after any previous dose administration.

Following dose administration, PK data is collected from samples taken at one or more time points. In some embodiments, PK data is collected from samples taken at at least three time points. In some embodiments, PK data is collected from samples taken at at least five time points. In some embodiments, the time points are selected from 0, 1, 2, 4, 6, 24, 48, 72, 96, and 120 hours. In some embodiments samples are taken at each of these time points.

PD data may additionally be collected. In some embodiments, data obtained from the individual includes (i) PK data relating to the concentration of unbound therapeutic agent in plasma; and (ii) PD data relating to the concentration of immune cells expressing IL2 receptor in blood.

Following dose administration, PD data is collected from samples at one or more time points. In some embodiments, PD data is collected from samples taken at at least three time points. In some embodiments, PD data is collected from samples taken at at least five time points. In some embodiments, the time points are selected from 0, 24, 48, 72, 96 and 120 hours. In some embodiments samples are taken at each of these time points.

Therapeutic Target Tissue

The therapeutic agents are capable of activating and expanding NK and CD8$^+$ effector T cells through IL-2R in the periphery and in the therapeutic target tissue microenvironment. They are therefore ideally suited for treating tumors, particularly malignant tumors. Accordingly, in a preferred embodiment, the therapeutic target tissue is a tumor. In some embodiments, the therapeutic target tissue is a solid tumor.

The tumor to be treated may be a solid tumor or a haematological cancer. Solid tumors to be treated include, but not limited to, liver cancer (e.g. HCC), breast cancer (including HER2 breast cancer and triple negative breast cancer), lung cancer, prostate cancer, colon cancer, stomach cancer, bladder cancer, bowel cancer, bone cancer, brain tumor (e.g. astrocytomas), cervical cancer, ovarian cancer, testicular cancer, glioma, melanoma, myeloma, neuroblastoma, pancreatic cancer, thyroid cancer, sarcoma, forms of skin cancer, kidney cancer (renal cell carcinoma). The tumor may be a squamous cell carcimona, for example of skin, lung, esophagus, cervix, head or neck.

Haematological cancers include, but are not limited to, lymphoma (non-Hodgkin and Hodgkin), and leukemia.

In some embodiments, the cancer is selected from the group consisting of metastatic melanoma, metastatic renal cell carcinoma, bladder cancer, lung cancer, head and neck squamous cell carcinoma, HER2 breast cancer, triple negative breast cancer (TNBC).

FAP- and CEA-IL2v

Recent studies suggest that FAP- and CEA-IL2v completely lack binding to CD25, but retain IL-Rβγ binding, show μM binding affinity to respective antigens, FAP on fibroblasts and CEA on tumor cells (Klein; J. Immunother. Cancer 2014; 2 (suppl.2):18). As a consequence of abolished binding to CD25 these molecules do not preferentially activate T-regs. The treatment of effector cells with IL2v reduces their sensitivity for Fas-mediated apoptosis (also known as activation induced cell death) as compared to wild-type IL-2 based immunocytokine. IL-2Rβγ bioactivity is retained and FAP- and CEA-IL2v activate NK, CD4+ and CD8+ T cells as shown by induction of activation markers, cell proliferation and cytokine release. Furthermore, CEA-IL2v and FAP-IL2v enhanced the cytotoxic activity of NK cells when combined with ADCC-competent antibodies. Mechanism of action studies in fully immunocompetent mice showed that the molecules strongly expand and activate NK, CD8+ T cells and gamma delta (gd) T cells (up to 100-fold) and skew the CD4:CD8 ratio strongly towards CD8+ T cells in the peripheral blood, lymphoid tissues, and in the tumor. In C57Bl/6 mice, CEA- and FAP-IL2v demonstrate improved safety despite a higher exposure and circulatory half-life than the analogous IL-2 based immunocytokine. MicroSPECT/CT imaging with radioactively labeled FAP-IL2v revealed good FAP-mediated tumor targeting in the orthotopic syngeneic Renca model with low normal tissue uptake and low accumulation in lymphoid tissues, contrary to analogous IL-2 based immunocytokine that showed preferential targeting to lymphoid tissue. Studies in tumor-bearing mice showed dose-dependent antitumor efficacy of FAP-IL2v and CEA-IL2v in syngeneic models. Additional studies in xenograft models in SCID mice transgenic for human CD16A showed that CEA-IL2v strongly enhances the antitumor efficacy and/or survival mediated by ADCC-competent antibodies, including trastuzumab and cetuximab.

CEA- and FAP-IL2v demonstrate superior safety, PK and tumor targeting, while lacking preferential induction of T-regs due to abolished CD25 binding, monovalency and high-affinity tumor-targeting as compared to classical IL-2-based immunocytokines. They retain capacity to activate and expand NK and CD8+ effector T cells through IL-2βγ in the periphery and the tumor microenvironment.

Therapeutic Agents

In one embodiment, the therapeutic agent comprises a polypeptide, variant or fragment thereof capable of targeting IL2 receptor (IL2R), e.g. IL-2Rβ (CD122) and/or IL-2Rγ (CD132). Accordingly, the therapeutic agent may comprise a CD122 and/or CD132 ligand. The polypeptide is preferably a cytokine polypeptide, for example, an IL2 polypeptide, variant or fragment. More preferably, the therapeutic agent comprises a variant IL-2 polypeptide having reduced binding affinity to the α-subunit of the IL-2 receptor as compared to wild-type IL-2.

Together with the β- and γ-subunits (also known as CD122 and CD132, respectively), the α-subunit (also known as CD25) forms the heterotrimeric high-affinity IL-2 receptor, while the dimeric receptor consisting only of the β- and γ-subunits is termed the intermediate-affinity IL-2 receptor. A variant IL-2 polypeptide with reduced binding to the α-subunit of the IL-2 receptor has a reduced ability to induce IL-2 signaling in regulatory T ($T_{reg}$) cells, induces less activation-induced cell death (AICD) in T cells, and has a reduced toxicity profile in vivo, compared to a wild-type IL-2 polypeptide (see e.g. WO 2012/107417, incorporated herein by reference in its entirety).

In a more specific embodiment, the variant IL-2 polypeptide comprises three amino acid substitutions at the positions corresponding to residue 42, 45 and 72 of human IL-2. In an even more specific embodiment, the variant IL-2 polypeptide is a human IL-2 polypeptide comprising the amino acid substitutions F42A, Y45A and L72G (numbering relative to the human IL-2 sequence SEQ ID NO: 1). In one embodiment the variant IL-2 polypeptide additionally comprises an amino acid mutation at a position corresponding to position 3 of human IL-2, which eliminates the O-glycosylation site of IL-2. In one embodiment said amino acid mutation which eliminates the O-glycosylation site of IL-2 at a position corresponding to residue 3 of human IL-2 is an amino acid substitution selected from the group of T3A, T3G, T3Q, T3E, T3N, T3D, T3R, T3K, and T3P. Particularly, said additional amino acid mutation is an amino acid substitution replacing a threonine residue by an alanine residue. A particular variant IL-2 polypeptide useful in the invention comprises four amino acid substitutions at positions corresponding to residues 3, 42, 45 and 72 of human IL-2. Specific amino acid substitutions are T3A, F42A, Y45A and L72G. This variant IL-2 polypeptide exhibits no detectable binding to CD25, reduced ability to induce apoptosis in T cells, reduced ability to induce IL-2 signaling in $T_{reg}$ cells, and a reduced toxicity profile in vivo (see e.g. WO 2012/107417, incorporated herein by reference in its entirety). However, it retains ability to activate IL-2 signaling in effector cells, to induce proliferation of effector cells, and to generate IFN-γ as a secondary cytokine by NK cells.

The IL-2 or variant IL-2 polypeptide according to any of the above embodiments may comprise additional mutations that provide further advantages such as increased expression or stability. For example, the cysteine at position 125 may be replaced with a neutral amino acid such as serine, alanine, threonine or valine, yielding C125S IL-2, C125A IL-2, C125T IL-2 or C125V IL-2 respectively, as described in U.S. Pat. No. 4,518,584. As described therein, one may also delete the N-terminal alanine residue of IL-2 yielding such mutants as des-A1 C125S or des-A1 C125A. Alternatively or conjunctively, the IL-2 variant may include a mutation whereby methionine normally occurring at position 104 of wild-type human IL-2 is replaced by a neutral amino acid such as alanine (see U.S. Pat. No. 5,206,344). The resulting variants, e. g., des-A1 M104A IL-2, des-A1 M104A C125S IL-2, M104A IL-2, M104A C125A IL-2, des-A1 M104A C125A IL-2, or M104A C125S IL-2 (these and other variants may be found in U.S. Pat. No. 5,116,943 and in Weiger et al., Eur J Biochem 180, 295-300 (1989)) may be used in conjunction with the particular IL-2 mutations described herein.

Thus, in certain embodiments the IL-2 or variant IL-2 polypeptide comprises an additional amino acid mutation at a position corresponding to residue 125 of human IL-2. In one embodiment said additional amino acid mutation is the amino acid substitution C125A.

In certain embodiments the variant IL-2 polypeptide is essentially a full-length IL-2 molecule, particularly a human full-length IL-2 molecule. In one embodiment, the variant IL-2 polypeptide comprises a polypeptide sequence that is at least 80%, at least 85%, at least 90%, or at least 95% identical to the sequence of SEQ ID NO: 1.

In a specific embodiment the variant IL-2 polypeptide comprises the polypeptide sequence of SEQ ID NO: 2.

In some embodiments, the therapeutic agent comprises an immunoconjugate. Particular immunoconjugates are described in WO 2012/107417 and WO 2012/146628 (each incorporated herein by reference in its entirety).

In one embodiment, the immunoconjugate comprises an antibody that specifically binds to CEA as described herein, and a variant IL-2 polypeptide as described herein. In one embodiment, the antibody is a full-length antibody.

In one embodiment, the antibody that specifically binds to CEA comprises a heavy chain variable region comprising the heavy chain CDR (HCDR) 1 of SEQ ID NO: 3, the HCDR2 of SEQ ID NO: 4, and the HCDR3 of SEQ ID NO: 5; and a light chain variable region comprising the light chain CDR (LCDR) 1 of SEQ ID NO: 6, the LCDR2 of SEQ ID NO: 7 and the LCDR3 of SEQ ID NO: 8. In a further embodiment, the antibody that specifically binds CEA comprises a heavy chain variable region sequence that is at least 80%, 85%, 90%, 95%, 96%, 97%, 98%, or 99% identical to of SEQ ID NO: 9 and a light chain variable region sequence that is at least 80%, 85%, 90%, 95%, 96%, 97%, 98%, or 99% identical to the sequence of SEQ ID NO: 10. In a further embodiment, the antibody that specifically binds CEA comprises the heavy chain variable region sequence of SEQ ID NO: 9 and the light chain variable region sequence of SEQ ID NO: 10.

In one embodiment, the antibody that specifically binds to CEA is a full-length antibody. In one embodiment, the antibody that specifically binds to CEA is an antibody of the human IgG class, particularly an antibody of the human IgG$_1$ class. In one embodiment, the antibody that specifically binds to CEA is an antibody fragment, particularly a Fab molecule or a scFv molecule, more particularly a Fab molecule. In one embodiment, the antibody that specifically binds to CEA is a humanized antibody.

In one embodiment the therapeutic agent comprises an immunoconjugate comprising
  (i) an antibody of the human IgG$_1$ subclass that specifically binds to CEA and comprises a heavy chain variable region comprising the heavy chain CDR (HCDR) 1 of SEQ ID NO: 3, the HCDR2 of SEQ ID NO: 4, and the HCDR3 of SEQ ID NO: 5; and a light chain variable region comprising the light chain CDR (LCDR) 1 of SEQ ID NO: 6, the LCDR2 of SEQ ID NO: 7 and the LCDR3 of SEQ ID NO: 8; and
  (ii) a variant human IL-2 polypeptide comprising the amino acid substitutions F42A, Y45A and L72G (numbering relative to the human IL-2 sequence SEQ ID NO: 1).

In one embodiment, the immunoconjugate comprises an antibody that specifically binds to FAP as described herein, and a variant IL-2 polypeptide as described herein. In one embodiment, the antibody is a full-length antibody.

In one embodiment, the antibody that specifically binds FAP comprises a heavy chain variable region sequence that is at least 80%, 85%, 90%, 95%, 96%, 97%, 98%, or 99% identical to of SEQ ID NO: 14 and a light chain variable region sequence that is at least 80%, 85%, 90%, 95%, 96%, 97%, 98%, or 99% identical to the sequence of SEQ ID NO: 15. In a further embodiment, the antibody that specifically binds FAP comprises the heavy chain variable region sequence of SEQ ID NO: 14 and the light chain variable region sequence of SEQ ID NO: 15.

In one embodiment, the antibody that specifically binds to FAP is a full-length antibody. In 5 one embodiment, the antibody that specifically binds to FAP is an antibody of the human IgG class, particularly an antibody of the human IgG$_1$ class. In one embodiment, the antibody that specifically binds to FAP is an antibody fragment, particularly a Fab molecule or a scFv molecule, more particularly a Fab molecule. In one embodiment, the antibody that specifically binds to FAP is a human antibody.

In one embodiment the therapeutic agent comprises an immunoconjugate comprising
  (i) an antibody of the human IgG$_1$ subclass that specifically binds to FAP and comprises the heavy chain variable region of SEQ ID NO: 14; and the light chain variable region of SEQ ID NO: 15; and
  (ii) a variant human IL-2 polypeptide comprising the amino acid substitutions F42A, Y45A and L72G (numbering relative to the human IL-2 sequence SEQ ID NO: 1).

In one embodiment, the immunoconjugate comprises no more than one variant IL-2 polypeptide. In one embodiment, the variant IL-2 polypeptide is fused to the carboxy-terminal amino acid of one of the antibody heavy chains, optionally through a linker peptide. Suitable, non-immunogenic linker peptides include, for example, (G$_4$S)$_n$, (SG$_4$)$_n$ or G$_4$(SG$_4$)$_n$ linker peptides, wherein n is generally a number between 1 and 10, typically between 2 and 4. In one embodiment, the linker peptide is (G$_4$S)$_3$.

In one embodiment, the immunoconjugate comprises a polypeptide comprising a sequence that is at least 80%, 85%, 90%, 95%, 96%, 97%, 98%, or 99% identical to the sequence of SEQ ID NO: 11, a polypeptide comprising a sequence that is at least 80%, 85%, 90%, 95%, 96%, 97%, 98%, or 99% identical to the sequence of SEQ ID NO: 12, and a polypeptide comprising a sequence that is at least 80%, 85%, 90%, 95%, 96%, 97%, 98%, or 99% identical to the sequence of SEQ ID NO: 13.

In one embodiment, the immunoconjugate comprises a polypeptide comprising the sequence of SEQ ID NO: 11, a polypeptide comprising the sequence of SEQ ID NO: 12, and a polypeptide comprising the sequence of SEQ ID NO: 13.

In one embodiment, the immunoconjugate is cergutuzumab amunaleukin (WHO Drug Information (International Nonproprietary Names for Pharmaceutical Substances), Recommended INN: List 75, 2016, pre-publication copy). In one embodiment, the therapeutic agent comprises cergutuzumab amunaleukin. In one embodiment, the therapeutic agent is cergutuzumab amunaleukin.

In one embodiment, the immunoconjugate comprises a polypeptide comprising a sequence that is at least 80%, 85%, 90%, 95%, 96%, 97%, 98%, or 99% identical to the sequence of SEQ ID NO: 16, a polypeptide comprising a sequence that is at least 80%, 85%, 90%, 95%, 96%, 97%, 98%, or 99% identical to the sequence of SEQ ID NO: 17, and a polypeptide comprising a sequence that is at least 80%, 85%, 90%, 95%, 96%, 97%, 98%, or 99% identical to the sequence of SEQ ID NO: 18.

In one embodiment, the immunoconjugate comprises a polypeptide comprising the sequence of SEQ ID NO: 16, a polypeptide comprising the sequence of SEQ ID NO: 17, and a polypeptide comprising the sequence of SEQ ID NO: 18. (FAP IL2v)

Fc Domain

An antibody, e.g. an immunoconjugate, comprised in the therapeutic agent may comprise an Fc domain which consists of a pair of polypeptide chains comprising heavy chain domains of an antibody molecule. For example, the Fc domain of an immunoglobulin G (IgG) molecule is a dimer, each subunit of which comprises the CH2 and CH3 IgG heavy chain constant domains. The two subunits of the Fc domain are capable of stable association with each other.

In one embodiment, the Fc domain is an IgG Fc domain. In a particular embodiment the Fc domain is an IgG$_1$ Fc domain. In another embodiment the Fc domain is an IgG$_4$ Fc domain.

In a more specific embodiment, the Fc domain is an $IgG_4$ Fc domain comprising an amino acid substitution at position S228 (EU numbering according to Kabat), particularly the amino acid substitution S228P. This amino acid substitution reduces in vivo Fab arm exchange of $IgG_4$ antibodies (see Stubenrauch et al., Drug Metabolism and Disposition 38, 84-91 (2010)). In a further particular embodiment the Fc domain is human. An exemplary sequence of a human $IgG_1$ Fc region is given in SEQ ID NO: 19.

Fc Domain Modifications Promoting Heterodimerization

Antibodies, e.g. immunoconjugates, comprised in the therapeutic agent may comprise different components (e.g. antigen binding domains, cytokines) fused to one or the other of the two subunits of the Fc domain, thus the two subunits of the Fc domain are typically comprised in two non-identical polypeptide chains. Recombinant co-expression of these polypeptides and subsequent dimerization leads to several possible combinations of the two polypeptides. To improve the yield and purity of such antibodies in recombinant production, it will thus be advantageous to introduce in the Fc domain of the antibody a modification promoting the association of the desired polypeptides.

Accordingly, in particular embodiments the Fc domain comprises a modification promoting the association of the first and the second subunit of the Fc domain. The site of most extensive protein-protein interaction between the two subunits of a human IgG Fc domain is in the CH3 domain of the Fc domain. Thus, in one embodiment said modification is in the CH3 domain of the Fc domain.

There exist several approaches for modifications in the CH3 domain of the Fc domain in order to enforce heterodimerization, which are well described e.g. in WO 96/27011, WO 98/050431, EP 1870459, WO 2007/110205, WO 2007/147901, WO 2009/089004, WO 2010/129304, WO 2011/90754, WO 2011/143545, WO 2012058768, WO 2013157954, WO 2013096291.

Typically, in all such approaches the CH3 domain of the first subunit of the Fc domain and the CH3 domain of the second subunit of the Fc domain are both engineered in a complementary manner so that each CH3 domain (or the heavy chain comprising it) can no longer homodimerize with itself but is forced to heterodimerize with the complementarily engineered other CH3 domain (so that the first and second CH3 domain heterodimerize and no homodimers between the two first or the two second CH3 domains are formed). These different approaches for improved heavy chain heterodimerization are contemplated as different alternatives in combination with heavy-light chain modifications (e.g. variable or constant region exchange/replacement in Fab arms, or introduction of substitutions of charged amino acids with opposite charges in the CH1/CL interface) which reduce light chain mispairing and Bence Jones-type side products.

In a specific embodiment said modification promoting the association of the first and the second subunit of the Fc domain is a so-called "knob-into-hole" modification, comprising a "knob" modification in one of the two subunits of the Fc domain and a "hole" modification in the other one of the two subunits of the Fc domain.

The knob-into-hole technology is described e.g. in U.S. Pat. Nos. 5,731,168; 7,695,936; Ridgway et al., Prot Eng 9, 617-621 (1996) and Carter, J Immunol Meth 248, 7-15 (2001). Generally, the method involves introducing a protuberance ("knob") at the interface of a first polypeptide and a corresponding cavity ("hole") in the interface of a second polypeptide, such that the protuberance can be positioned in the cavity so as to promote heterodimer formation and hinder homodimer formation. Protuberances are constructed by replacing small amino acid side chains from the interface of the first polypeptide with larger side chains (e.g. tyrosine or tryptophan). Compensatory cavities of identical or similar size to the protuberances are created in the interface of the second polypeptide by replacing large amino acid side chains with smaller ones (e.g. alanine or threonine).

Accordingly, in a particular embodiment, in the CH3 domain of the first subunit of the Fc domain an amino acid residue is replaced with an amino acid residue having a larger side chain volume, thereby generating a protuberance within the CH3 domain of the first subunit which is positionable in a cavity within the CH3 domain of the second subunit, and in the CH3 domain of the second subunit of the Fc domain an amino acid residue is replaced with an amino acid residue having a smaller side chain volume, thereby generating a cavity within the CH3 domain of the second subunit within which the protuberance within the CH3 domain of the first subunit is positionable.

Preferably said amino acid residue having a larger side chain volume is selected from the group consisting of arginine (R), phenylalanine (F), tyrosine (Y), and tryptophan (W). Preferably said amino acid residue having a smaller side chain volume is selected from the group consisting of alanine (A), serine (S), threonine (T), and valine (V).

The protuberance and cavity can be made by altering the nucleic acid encoding the polypeptides, e.g. by site-specific mutagenesis, or by peptide synthesis.

In a specific embodiment, in the CH3 domain of the first subunit of the Fc domain (the "knobs" subunit) the threonine residue at position 366 is replaced with a tryptophan residue (T366W), and in the CH3 domain of the second subunit of the Fc domain (the "hole" subunit) the tyrosine residue at position 407 is replaced with a valine residue (Y407V). In one embodiment, in the second subunit of the Fc domain additionally the threonine residue at position 366 is replaced with a serine residue (T366S) and the leucine residue at position 368 is replaced with an alanine residue (L368A) (numberings according to Kabat EU index).

In yet a further embodiment, in the first subunit of the Fc domain additionally the serine residue at position 354 is replaced with a cysteine residue (S354C) or the glutamic acid residue at position 356 is replaced with a cysteine residue (E356C), particularly the serine residue at position 354 is replaced with a cysteine residue (S354C), and in the second subunit of the Fc domain additionally the tyrosine residue at position 349 is replaced by a cysteine residue (Y349C) (numberings according to Kabat EU index). Introduction of these two cysteine residues results in formation of a disulfide bridge between the two subunits of the Fc domain, further stabilizing the dimer (Carter, J Immunol Methods 248, 7-15 (2001)).

In a particular embodiment, the first subunit of the Fc domain comprises amino acid substitutions S354C and T366W, and the second subunit of the Fc domain comprises amino acid substitutions Y349C, T366S, L368A and Y407V (numbering according to Kabat EU index).

In a particular embodiment the mutant 11-2 polypeptide in the immunoconjugate described herein is fused to the first subunit of the Fc domain (comprising the "knob" modification). Without wishing to be bound by theory, fusion of the 11-2 polypeptide to the knob-containing subunit of the Fc domain will (further) minimize the generation of immunoconjugates comprising two 11-2 polypeptides (steric clash of two knob-containing polypeptides).

Other techniques of CH3-modification for enforcing the heterodimerization are contemplated as alternatives according to the invention and are described e.g. in WO 96/27011, WO 98/050431, EP 1870459, WO 2007/110205, WO 2007/147901, WO 2009/089004, WO 2010/129304, WO 2011/90754, WO 2011/143545, WO 2012/058768, WO 2013/157954, WO 2013/096291.

In one embodiment the heterodimerization approach described in EP 1870459 A1, is used alternatively. This approach is based on the introduction of charged amino acids with opposite charges at specific amino acid positions in the CH3/CH3 domain interface between the two subunits of the Fc domain. One preferred embodiment are amino acid mutations R409D; K370E in one of the two CH3 domains (of the Fc domain) and amino acid mutations D399K; E357K in the other one of the CH3 domains of the Fc domain (numbering according to Kabat EU index).

In another embodiment the antibody comprises amino acid mutation T366W in the CH3 domain of the first subunit of the Fc domain and amino acid mutations T366S, L368A, Y407V in the CH3 domain of the second subunit of the Fc domain, and additionally amino acid mutations R409D; K370E in the CH3 domain of the first subunit of the Fc domain and amino acid mutations D399K; E357K in the CH3 domain of the second subunit of the Fc domain (numberings according to Kabat EU index).

In another embodiment the antibody comprises amino acid mutations S354C, T366W in the CH3 domain of the first subunit of the Fc domain and amino acid mutations Y349C, T366S, L368A, Y407V in the CH3 domain of the second subunit of the Fc domain, or the antibody comprises amino acid mutations Y349C, T366W in the CH3 domain of the first subunit of the Fc domain and amino acid mutations S354C, T366S, L368A, Y407V in the CH3 domains of the second subunit of the Fc domain and additionally amino acid mutations R409D; K370E in the CH3 domain of the first subunit of the Fc domain and amino acid mutations D399K; E357K in the CH3 domain of the second subunit of the Fc domain (all numberings according to Kabat EU index).

In one embodiment the heterodimerization approach described in WO 2013/157953 is used alternatively. In one embodiment a first CH3 domain comprises amino acid mutation T366K and a second CH3 domain comprises amino acid mutation L351D (numberings according to Kabat EU index). In a further embodiment the first CH3 domain comprises further amino acid mutation L351K. In a further embodiment the second CH3 domain comprises further an amino acid mutation selected from Y349E, Y349D and L368E (preferably L368E) (numberings according to Kabat EU index).

In one embodiment the heterodimerization approach described in WO 2012/058768 is used alternatively. In one embodiment a first CH3 domain comprises amino acid mutations L351Y, Y407A and a second CH3 domain comprises amino acid mutations T366A, K409F. In a further embodiment the second CH3 domain comprises a further amino acid mutation at position T411, D399, S400, F405, N390, or K392, e.g. selected from a) T41 IN, T411R, T411Q, T411K, T411D, T411E or T411W, b) D399R, D399W, D399Y or D399K, c) S400E, S400D, S400R, or S400K, d) F405I, F405M, F405T, F405S, F405V or F405W, e) N390R, N390K or N390D, f) K392V, K392M, K392R, K392L, K392F or K392E (numberings according to Kabat EU index). In a further embodiment a first CH3 domain comprises amino acid mutations L351Y, Y407A and a second CH3 domain comprises amino acid mutations T366V, K409F. In a further embodiment a first CH3 domain comprises amino acid mutation Y407A and a second CH3 domain comprises amino acid mutations T366A, K409F. In a further embodiment the second CH3 domain further comprises amino acid mutations K392E, T411E, D399R and S400R (numberings according to Kabat EU index).

In one embodiment the heterodimerization approach described in WO 2011/143545 is used alternatively, e.g. with the amino acid modification at a position selected from the group consisting of 368 and 409 (numbering according to Kabat EU index).

In one embodiment the heterodimerization approach described in WO 2011/090762, which also uses the knobs-into-holes technology described above, is used alternatively. In one embodiment a first CH3 domain comprises amino acid mutation T366W and a second CH3 domain comprises amino acid mutation Y407A. In one embodiment a first CH3 domain comprises amino acid mutation T366Y and a second CH3 domain comprises amino acid mutation Y407T (numberings according to Kabat EU index).

In one embodiment the antibody or its Fc domain is of IgG$_2$ subclass and the heterodimerization approach described in WO 2010/129304 is used alternatively.

In an alternative embodiment a modification promoting association of the first and the second subunit of the Fc domain comprises a modification mediating electrostatic steering effects, e.g. as described in PCT publication WO 2009/089004. Generally, this method involves replacement of one or more amino acid residues at the interface of the two Fc domain subunits by charged amino acid residues so that homodimer formation becomes electrostatically unfavorable but heterodimerization electrostatically favorable. In one such embodiment a first CH3 domain comprises amino acid substitution of K392 or N392 with a negatively charged amino acid (e.g. glutamic acid (E), or aspartic acid (D), preferably K392D or N392D) and a second CH3 domain comprises amino acid substitution of D399, E356, D356, or E357 with a positively charged amino acid (e.g. lysine (K) or arginine (R), preferably D399K, E356K, D356K, or E357K, and more preferably D399K and E356K). In a further embodiment the first CH3 domain further comprises amino acid substitution of K409 or R409 with a negatively charged amino acid (e.g. glutamic acid (E), or aspartic acid (D), preferably K409D or R409D). In a further embodiment the first CH3 domain further or alternatively comprises amino acid substitution of K439 and/or K370 with a negatively charged amino acid (e.g. glutamic acid (E), or aspartic acid (D)) (all numberings according to Kabat EU index).

In yet a further embodiment the heterodimerization approach described in WO 2007/147901 is used alternatively. In one embodiment a first CH3 domain comprises amino acid mutations K253E, D282K, and K322D and a second CH3 domain comprises amino acid mutations D239K, E240K, and K292D (numberings according to Kabat EU index).

In still another embodiment the heterodimerization approach described in WO 2007/110205 can be used alternatively.

In one embodiment, the first subunit of the Fc domain comprises amino acid substitutions K392D and K409D, and the second subunit of the Fc domain comprises amino acid substitutions D356K and D399K (numbering according to Kabat EU index).

Fc Domain Modifications Reducing Fc Receptor Binding and/or Effector Function

The Fc domain confers to an antibody, such as an immunoconjugate, favorable pharmacokinetic properties, including a long serum half-life which contributes to good accumulation in the target tissue and a favorable tissue-blood distribution ratio. At the same time it may, however, lead to undesirable targeting of the antibody to cells expressing Fc receptors rather than to the preferred antigen-bearing cells. Moreover, the co-activation of Fc receptor signaling pathways may lead to cytokine release which, in combination with other immunostimulatory properties the antibody may have and the long half-life of the antibody, results in excessive activation of cytokine receptors and severe side effects upon systemic administration.

Accordingly, in particular embodiments, the Fc domain of the antibody, particularly immunoconjugate, comprised in the therapeutic agent exhibits reduced binding affinity to an Fc receptor and/or reduced effector function, as compared to a native $IgG_1$ Fc domain. In one such embodiment the Fc domain (or the molecule, e.g. antibody, comprising said Fc domain) exhibits less than 50%, preferably less than 20%, more preferably less than 10% and most preferably less than 5% of the binding affinity to an Fc receptor, as compared to a native $IgG_1$ Fc domain (or a corresponding molecule comprising a native $IgG_1$ Fc domain), and/or less than 50%, preferably less than 20%, more preferably less than 10% and most preferably less than 5% of the effector function, as compared to a native $IgG_1$ Fc domain domain (or a corresponding molecule comprising a native $IgG_1$ Fc domain). In one embodiment, the Fc domain (or the molecule, e.g. antibody, comprising said Fc domain) does not substantially bind to an Fc receptor and/or induce effector function. In a particular embodiment the Fc receptor is an Fcγ receptor. In one embodiment the Fc receptor is a human Fc receptor. In one embodiment the Fc receptor is an activating Fc receptor. In a specific embodiment the Fc receptor is an activating human Fcγ receptor, more specifically human FcγRIIIa, FcγRI or FcγRIIa, most specifically human FcγRIIIa. In one embodiment the effector function is one or more selected from the group of CDC, ADCC, ADCP, and cytokine secretion. In a particular embodiment the effector function is ADCC. In one embodiment the Fc domain exhibits substantially similar binding affinity to neonatal Fc receptor (FcRn), as compared to a native $IgG_1$ Fc domain. Substantially similar binding to FcRn is achieved when the Fc domain (or the molecule, e.g. antibody, comprising said Fc domain) exhibits greater than about 70%, particularly greater than about 80%, more particularly greater than about 90% of the binding affinity of a native $IgG_1$ Fc domain (or the corresponding molecule comprising a native $IgG_1$ Fc domain) to FcRn.

In certain embodiments the Fc domain is engineered to have reduced binding affinity to an Fc receptor and/or reduced effector function, as compared to a non-engineered Fc domain. In particular embodiments, the Fc domain comprises one or more amino acid mutation that reduces the binding affinity of the Fc domain to an Fc receptor and/or effector function. Typically, the same one or more amino acid mutation is present in each of the two subunits of the Fc domain. In one embodiment the amino acid mutation reduces the binding affinity of the Fc domain to an Fc receptor. In one embodiment the amino acid mutation reduces the binding affinity of the Fc domain to an Fc receptor by at least 2-fold, at least 5-fold, or at least 10-fold. In embodiments where there is more than one amino acid mutation that reduces the binding affinity of the Fc domain to the Fc receptor, the combination of these amino acid mutations may reduce the binding affinity of the Fc domain to an Fc receptor by at least 10-fold, at least 20-fold, or even at least 50-fold. In one embodiment the molecule, e.g. antibody, comprising an engineered Fc domain exhibits less than 20%, particularly less than 10%, more particularly less than 5% of the binding affinity to an Fc receptor as compared to a corresponding molecule comprising a non-engineered Fc domain. In a particular embodiment the Fc receptor is an Fcγ receptor. In some embodiments the Fc receptor is a human Fc receptor. In some embodiments the Fc receptor is an activating Fc receptor. In a specific embodiment the Fc receptor is an activating human Fcγ receptor, more specifically human FcγRIIIa, FcγRI or FcγRIIa, most specifically human FcγRIIIa. Preferably, binding to each of these receptors is reduced.

In some embodiments binding affinity to a complement component, specifically binding affinity to C1q, is also reduced. In one embodiment binding affinity to neonatal Fc receptor (FcRn) is not reduced. Substantially similar binding to FcRn, i.e. preservation of the binding affinity of the Fc domain to said receptor, is achieved when the Fc domain (or the molecule, e.g. antibody, comprising said Fc domain) exhibits greater than about 70% of the binding affinity of a non-engineered form of the Fc domain (or a corresponding molecule comprising said non-engineered form of the Fc domain) to FcRn. The Fc domain, or molecule (e.g. antibody) comprising said Fc domain, may exhibit greater than about 80% and even greater than about 90% of such affinity. In certain embodiments the Fc domain is engineered to have reduced effector function, as compared to a non-engineered Fc domain. The reduced effector function can include, but is not limited to, one or more of the following: reduced complement dependent cytotoxicity (CDC), reduced antibody-dependent cell-mediated cytotoxicity (ADCC), reduced antibody-dependent cellular phagocytosis (ADCP), reduced cytokine secretion, reduced immune complex-mediated antigen uptake by antigen-presenting cells, reduced binding to NK cells, reduced binding to macrophages, reduced binding to monocytes, reduced binding to polymorphonuclear cells, reduced direct signaling inducing apoptosis, reduced crosslinking of target-bound antibodies, reduced dendritic cell maturation, or reduced T cell priming.

In one embodiment the reduced effector function is one or more selected from the group of reduced CDC, reduced ADCC, reduced ADCP, and reduced cytokine secretion. In a particular embodiment the reduced effector function is reduced ADCC. In one embodiment the reduced ADCC is less than 20% of the ADCC induced by a non-engineered Fc domain (or a corresponding molecule comprising a non-engineered Fc domain).

In one embodiment the amino acid mutation that reduces the binding affinity of the Fc domain to an Fc receptor and/or effector function is an amino acid substitution. In one embodiment the Fc domain comprises an amino acid substitution at a position selected from the group of E233, L234, L235, N297, P331 and P329 (numberings according to Kabat EU index). In a more specific embodiment the Fc domain comprises an amino acid substitution at a position selected from the group of L234, L235 and P329 (numberings according to Kabat EU index). In some embodiments the Fc domain comprises the amino acid substitutions L234A and L235A (numberings according to Kabat EU index). In one such embodiment, the Fc domain is an $IgG_1$ Fc domain, particularly a human $IgG_1$ Fc domain.

In one embodiment the Fc domain comprises an amino acid substitution at position P329. In a more specific embodiment the amino acid substitution is P329A or P329G, particularly P329G (numberings according to Kabat EU index). In one embodiment the Fc domain comprises an amino acid substitution at position P329 and a further amino acid substitution at a position selected from E233, L234, L235, N297 and P331 (numberings according to Kabat EU index).

In a more specific embodiment the further amino acid substitution is E233P, L234A, L235A, L235E, N297A, N297D or P331S. In particular embodiments the Fc domain comprises amino acid substitutions at positions P329, L234 and L235 (numberings according to Kabat EU index). In more particular embodiments the Fc domain comprises the amino acid mutations L234A, L235A and P329G ("P329G LALA"). In one such embodiment, the Fc domain is an $IgG_1$ Fc domain, particularly a human $IgG_1$ Fc domain. The "P329G LALA" combination of amino acid substitutions almost completely abolishes Fcγ receptor (as well as complement) binding of a human $IgG_1$ Fc domain, as described in PCT publication no. WO 2012/130831, incorporated herein by reference in its entirety. WO 2012/130831 also describes methods of preparing such mutant Fc domains and methods for determining its properties such as Fc receptor binding or effector functions.

$IgG_4$ antibodies exhibit reduced binding affinity to Fc receptors and reduced effector functions as compared to $IgG_1$ antibodies. Hence, in some embodiments the Fc domain is an $IgG_4$ Fc domain, particularly a human $IgG_4$ Fc domain. In one embodiment the $IgG_4$ Fc domain comprises amino acid substitutions at position S228, specifically the amino acid substitution S228P (numberings according to Kabat EU index). To further reduce its binding affinity to an Fc receptor and/or its effector function, in one embodiment the $IgG_4$ Fc domain comprises an amino acid substitution at position L235, specifically the amino acid substitution L235E (numberings according to Kabat EU index). In another embodiment, the $IgG_4$ Fc domain comprises an amino acid substitution at position P329, specifically the amino acid substitution P329G (numberings according to Kabat EU index). In a particular embodiment, the $IgG_4$ Fc domain comprises amino acid substitutions at positions S228, L235 and P329, specifically amino acid substitutions S228P, L235E and P329G (numberings according to Kabat EU index). Such $IgG_4$ Fc domain mutants and their Fcγ receptor binding properties are described in PCT publication no. WO 2012/130831, incorporated herein by reference in its entirety.

In a particular embodiment the Fc domain exhibiting reduced binding affinity to an Fc receptor and/or reduced effector function, as compared to a native $IgG_1$ Fc domain, is a human $IgG_1$ Fc domain comprising the amino acid substitutions L234A, L235A and optionally P329G, or a human $IgG_4$ Fc domain comprising the amino acid substitutions S228P, L235E and optionally P329G (numberings according to Kabat EU index).

In certain embodiments N-glycosylation of the Fc domain has been eliminated. In one such embodiment the Fc domain comprises an amino acid mutation at position N297, particularly an amino acid substitution replacing asparagine by alanine (N297A) or aspartic acid (N297D) or glycine (N297G) (numberings according to Kabat EU index).

In addition to the Fc domains described hereinabove and in PCT publication no. WO 2012/130831, Fc domains with reduced Fc receptor binding and/or effector function also include those with substitution of one or more of Fc domain residues 238, 265, 269, 270, 297, 327 and 329 (U.S. Pat. No. 6,737,056) (numberings according to Kabat EU index). Such Fc mutants include Fc mutants with substitutions at two or more of amino acid positions 265, 269, 270, 297 and 327, including the so-called "DANA" Fc mutant with substitution of residues 265 and 297 to alanine (U.S. Pat. No. 7,332,581).

Mutant Fc domains can be prepared by amino acid deletion, substitution, insertion or modification using genetic or chemical methods well known in the art. Genetic methods may include site-specific mutagenesis of the encoding DNA sequence, PCR, gene synthesis, and the like. The correct nucleotide changes can be verified for example by sequencing.

Binding to Fc receptors can be easily determined e.g. by ELISA, or by Surface Plasmon Resonance (SPR) using standard instrumentation such as a BIAcore instrument (GE Healthcare), and Fc receptors such as may be obtained by recombinant expression. Alternatively, binding affinity of Fc domains or molecules comprising an Fc domain for Fc receptors may be evaluated using cell lines known to express particular Fc receptors, such as human NK cells expressing FcγIIIa receptor.

Effector function of an Fc domain, or a molecule (e.g. an antibody) comprising an Fc domain, can be measured by methods known in the art. A suitable assay for measuring ADCC is described herein. Other examples of in vitro assays to assess ADCC activity of a molecule of interest are described in U.S. Pat. No. 5,500,362; Hellstrom et al. Proc Natl Acad Sci USA 83, 7059-7063 (1986) and Hellstrom et al., Proc Natl Acad Sci USA 82, 1499-1502 (1985); U.S. Pat. No. 5,821,337; Bruggemann et al., J Exp Med 166, 1351-1361 (1987). Alternatively, non-radioactive assays methods may be employed (see, for example, ACTI™ non-radioactive cytotoxicity assay for flow cytometry (CellTechnology, Inc. Mountain View, CA); and CytoTox 96® non-radioactive cytotoxicity assay (Promega, Madison, WI)). Useful effector cells for such assays include peripheral blood mononuclear cells (PBMC) and Natural Killer (NK) cells. Alternatively, or additionally, ADCC activity of the molecule of interest may be assessed in vivo, e.g. in a animal model such as that disclosed in Clynes et al., Proc Natl Acad Sci USA 95, 652-656 (1998).

In some embodiments, binding of the Fc domain to a complement component, specifically to C1q, is reduced. Accordingly, in some embodiments wherein the Fc domain is engineered to have reduced effector function, said reduced effector function includes reduced CDC. C1q binding assays may be carried out to determine whether the Fc domain, or molecule (e.g. antibody) comprising the Fc domain, is able to bind C1q and hence has CDC activity. See e.g., C1q and C3c binding ELISA in WO 2006/029879 and WO 2005/100402. To assess complement activation, a CDC assay may be performed (see, for example, Gazzano-Santoro et al., J Immunol Methods 202, 163 (1996); Cragg et al., Blood 101, 1045-1052 (2003); and Cragg and Glennie, Blood 103, 2738-2743 (2004)).

Examples

Data:
To develop this method, we used pharmacokinetic, pharmacodynamic, and imaging data from CEA-IL2v phase I clinical study:
  Pharmacokinetic (PK): CEA-IL2v concentration measured at different times in 74 cancer patients receiving CEA-IL2v Q2W or QW (824 analyzed points in total, 11.14 in average per patient, min 4 and max 28)
  Pharmacodynamic (PD): concentration of CD8+ and CD4+ T cells, NK cells and B cells as an output of FACS analysis performed in the same 74 patients at different times (273 analyzed points in total, 3.69 in average per patient, min 0 and max 9)
  Imaging: data in 14 patients receiving radio labelled agent with compound concentration measured at three time points (day 1, 4, 8)

Developed Model:

Based on the previously described data, a mathematical model was developed (FIG. 1). The model predicts that QW delivery of the drug will result in expansion of immune cells in blood (see FIG. 2).

Working Example

In this example, a CEA-positive CRC patient with extensive PK measurement and dosed 20 mg in a QW regimen was chosen. At first, only the first seven PK measurements (until day 4: sampling 1 h, 2.5 h, 4.5 h, 6.5 h, 24 h, 72 h, 96 h; values 2.72, 6.54, 5.83, 5.72, 3.22, 0.193, 0.027 mg/mL) were analyzed and individual PK parameters, namely $k_{clear}$, $k_{on}$, $k_{off}$, $k_{in}$, $k_{out}$, $k_{int}$, and $\eta$, estimated using Bayesian method with population parameter values (as reported hereinabove) used as priors. This led to the following estimates:

kclear=0.036283;
kon=1.1229;
koff=0.0054365;
kin=0.0022355;
kout=0.010648;
kint=0.010352;

The parameter "$\eta$" for the uptake was fixed to the population values obtained in the two CRC patients out of 4 being CEA+ and with imaging data at 30 mg at cycle 1.

$\eta$=1.9224.

PK (estimated) and tumor uptake (fixed to CRC CEA+ typical values) parameters were used to simulate corresponding PK and uptake at successive cycles. PK predictions were checked by super-imposing remaining PK assessment at later cycles. The model was used to identify a dosing regimen able to compensate for the TMDD phenomenon in periphery. The proposed heuristic dosing schedules, which consists of a dose given every 5 days, starting at 20 mg and incrementing by 5 mg at each cycle give very similar uptake (calculated as area under the curve) than the theoretical in the absence of TMDD: 0.050 mg/cm3*day versus 0.048 mg/cm3*day in the absence of TMDD.

In FIG. 8, the left graph shows individual patient pharmacokinetic data (only circles are used to calibrate the model to this individual). The dashed line represents the prediction for this given patient and stars are observations not used to make this prediction.

The center graph is the corresponding predicted profile of antibody uptake in tumor (continuous line) for this patient. The dashed line represents the theoretical prediction if target peripheral expansion was not occurring (this is the uptake one would like to achieve by intensifying the dosing regimen).

The right graph is the predicted uptake when simulating an intensified dosing regimen for this patient. Here (continuous line), the antibody is given every 5 days instead of 7. Dose I was the start at 20 mg and this was followed by an increment of 5 mg each week. The uptake of this new "individualized" regimen is predicted to be similar to the theoretical uptake without immune cell expansion (dashed line).

CEA-IL2v/FAP-IL2v Dosing Regimen

The first dose of IL2v is the most critical because it is hitting a resting system where no target expansion has occurred yet. The exposure of the drug is the highest and hence, toxicity is most pronounced after the first administration. CEA-IL2v first dose can be up to 30 mg (MTD), for FAP-IL2v a preferred dose is 25 mg. However the inventors are still looking at dose escalation and have not yet reached the MTD. Accordingly, a dose of 30 mg or more may be possible.

There is a high variability in the exposure of the first dose between individuals and therefore there is a need to start the therapy with the highest safe dose for everyone possible to exploit maximal exposure.

Accordingly, the following model is proposed: start therapy with the highest dose which every patient can tolerate, i.e. 20 mg for CEA-IL2v. Determine PK and feed the model described herein with the data to predict TMDD. Then adjust the dose for the third administration to compensate for TMDD and repeat the PK sampling. It is preferable to repeat this loop until the immune cell expansion has reached a plateau or toxicity prohibits further up-dosing. The results will indicate that a personalized dosing could be done based on one individual's proliferative potential of the immune cells. E.g.:

Patient 1: Dose (D) 1=20 mg, D3=25 mg, D5 seqq=30 mg
Patient 2: D1=20 mg, D3=30 mg, D5=40 mg, D7 seqq=45 mg With regard to CEA-IL2v, the MTD has already been defined at 30 mg. The highest safe starting dose for CEA-IL2v has been defined at 20 mg.

In a preferred embodiment, the starting dose for CEA-IL2v would be 20 mg (week 1+2). Thereafter the patients will be assigned to the following up-titration schedules according to their immune cell proliferative potential as determined using the model described herein:

a) low TMDD→20 mg (week 3 seqq.),
b) intermediate TMDD→25 mg (week 3 seqq),
c) high TMDD→25 mg (week 3+4), 30 mg (week 5 seqq.).

For FAP-IL2v, a MTD has not yet been defined, but as it is greater than 25 mg, the dosing recommendation would follow the same logic as for CEA-IL2v, but potentially with more up-titration steps:

In a preferred embodiment, the starting dose for FAP-IL2v would be 20 mg (week 1 (w1)+w2). Thereafter the patients will be assigned to the following up-titration schedules according to their immune cell proliferative potential as determined using the model described herein:

a) low TMDD: 25 mg (w3+w4), 30 mg (w5 seqq.)
b) intermediate TMDD: 30 mg (w3+w4), 40 mg (w5 seqq)
c) high TMDD: 30 mg (w3+w4), 40 mg (w5+w6), 50 mg (w7 seqq.)

REFERENCES

[1] Proleukin package insert.
[2] Lode et al., Blood 1998.
[3] Mager. Targeted-mediated drug disposition and dynamics. Biochem Pharmacol 2006.
[4] Lindstrom and Bates. Nonlinear mixed effects models for repeated measures data. Biometrics 1990; 46:673-87
[5] www.lixoft.com
[6] Schmidt and Wittrup. A modeling analysis of the effects of molecular size and binding affinity on tumor targeting. Mol Cancer Ther 2009.
[7] Thurber and Wittrup. A mechanistic compartmental model for total antibody uptake in tumors. J Theor Biol 2012.
[8] Gibiansly and Gibiansky. Target-mediated drug disposition model: approximations, identifiability of model parameters and applications to the population pharmacokinetic-pharmacodynamic modeling of biologics. Expert Opin Drug Metab Toxicol. 2009.

The invention claimed is:

1. A method for treating an individual in need thereof with an effective dose of a therapeutic agent comprising
   a) requesting a test providing results of an analysis to determine an effective amount of said therapeutic agent for the individual; and
   b) administering said therapeutic agent to the individual at the determined effective amount;
   wherein said test comprises
   a) simulating a model, using data obtained from the individual at one or more time points following a first or previous dose administration of the therapeutic agent; wherein the data includes (i) PK data relating to the amount of unbound therapeutic agent; (ii) PD data relating to immune cells expressing IL2 receptor; and (iii) imaging data relating to the amount of therapeutic agent that is taken up by the therapeutic target tissue, wherein the model is:

$$\frac{d[Ab]_{free}}{dt} = -k_{clear} \cdot [Ab]_{free} - (k_{on} \cdot [Ab]_{free} \cdot [IL2R]_{free} - k_{off} \cdot [Complex])$$

$$\frac{d[ILR2]_{free}}{dt} = k_{in} - k_{out} \cdot [ILR2]_{free} -$$

$$(k_{on} \cdot [Ab]_{free} \cdot [IL2R]_{free} - k_{off} \cdot [Complex]) + \eta \cdot k_{int} \cdot [Complex]$$

$$\frac{d[Complex]}{dt} = k_{on} \cdot [Ab]_{free} \cdot [IL2R]_{free} - k_{off} \cdot [Complex] - k_{int} \cdot [Complex]$$

$$\frac{d[Ab]_{total}^T}{dt} =$$

$$\frac{2 \cdot P \cdot R_{Cap}}{R_{Kgrogh}^2} \left( [Ab]_{free} - \left( \frac{Kd}{\left(\frac{[Ag]}{\varepsilon}\right) + K_D} \right) \frac{d[Ab]_{total}^T}{\varepsilon} - k_e \left( \frac{\frac{[Ag]}{\varepsilon}}{\left(\frac{[Ag]}{\varepsilon}\right) + K_D} \right) [Ab]_{total}^T \right)$$

wherein:
   $[Ab]_{free}$ is the concentration of unbound therapeutic agent in plasma,
   $[IL2R]_{free}$ is the concentration of unbound immune cells expressing IL2 receptor in blood, which is given by $k_{in}/k_{out}$ if the data does not include the PD data, or it is obtained from the PD data if the data includes the PD data,
   [Complex] is the concentration of complex between the therapeutic agent and immune cells expressing IL-2 receptor (IL2R+ cells),
   $[Ab]_{total}^T$ is the concentration of therapeutic agent in the target tissue,
   $k_{clear}$ is a constant rate of elimination of therapeutic agent from plasma and has a value between 0.02 and 0.04 hour-1;
   $k_{on}$ is an association rate of complex between the therapeutic agent and immune cells expressing IL-2 receptor and has a value between 0.26 and 4.5 µM$^{-1}$h$^{-1}$,
   $k_{off}$ is a dissociation rate of complex between the therapeutic agent and immune cells expressing IL-2 receptor and has a value between 0.0035 and 0.02 h$^{-1}$,
   $k_{in}$ is a constant influx rate of IL2R+ cells in plasma and has a value between 0.0006 and 0.0144 µMh$^{-1}$;
   $k_{out}$ is a natural decay rate of IL2R+ cells in plasma and has a value between 0.0018 and 0.069 h$^{-1}$,
   $k_{int}$ is the internalization rate of the therapeutic agent and has a value between 0.0066 and 0.023 h$^{-1}$; and
   η is a constant rate of expansion of IL2R+ cells in plasma as a result of the binding (internalization) of the therapeutic agent and has a value between 1.02 and 3.31;
   P is the permeability across capillary vessels;
   $R_{Cap}$ is the capillary radius;
   $R_{Kgrogh}$ is the radius of the Krogh cylinder;
   $K_d$ is the dissociation constant;
   [Ag] is the concentration of antigen in the tissue;
   ε is the volume fraction; and
   $k_e$ is the constant rate of drug internalization and degradation from the target tissue;
   b) determining an effective dose for the individual based on the increase in therapeutic agent required to compensate for reduction in free therapeutic agent, wherein the optimal dosing regimen provides the best target tissue uptake compared to other simulated dosing regimens;
   wherein the therapeutic agent is a compound which is capable of targeting IL2R.

2. The method according to claim 1, further comprising the step of obtaining the PK and PD data from a sample obtained from the individual.

3. The method according to claim 1, further comprising the step of obtaining a sample from the individual following the dose administration.

4. The method according to claim 1, wherein the PK data is the concentration of unbound therapeutic agent in plasma at one or more time points following dose administration of the individual with the therapeutic agent.

5. The method according to claim 4, wherein the one or more time points include three or more time points between 0 and 120 hours following dose administration to the individual.

6. The method according to claim 1, wherein the PD data is the concentration of IL2R+ cells in blood at one or more time points following dose administration of the individual with the therapeutic agent.

7. The method according to claim 6, wherein the concentration of IL2R+ cells in blood is determined by measuring the concentration of soluble CD25.

8. The method according to claim 6, wherein the concentration of IL2R+ cells in blood is determined by measuring the concentration of one or more immune cells selected from the group consisting of CD4+, CD8+, NK cells, T-cells and B-cells.

9. The method according to claim 1, wherein the one or more time points follow the initial dose administration of the individual with the therapeutic agent.

10. The method according to claim 1, wherein $k_{clear}$ has a value between 0.025 and 0.035 hour$^{-1}$; $k_{on}$ has a value between 1 and 3.5 μM$^{-1}$h$^{-1}$; $k_{off}$ has a value between 0.006 and 0.018 h$^{-1}$, $k_{in}$ has a value between 0.002 and 0.0035 μM·h$^{-1}$; $k_{out}$ has a value between 0.005 and 0.02 h$^{-1}$, $k_{int}$ has a value between 0.01 and 0.02 h$^{-1}$; and η has a value between 1.5 and 2.0.

11. The method according to claim 1, wherein the therapeutic agent comprises an IL2 polypeptide, variant or fragment thereof.

12. The method according to claim 11, wherein said therapeutic agent is an immunoconjugate.

13. The method according to claim 12, wherein said immunoconjugate comprises an antibody or fragment thereof specific for a tumor cell.

14. The method according to claim 13, wherein said antibody or fragment thereof is specific for carcinoembryonic antigen (CEA).

15. The method according to claim 13, wherein said antibody or fragment thereof is specific for fibroblast activation protein (FAP).

16. The method according to claim 1, wherein said individual is being treated for cancer.

17. The method according to claim 1, wherein the effective dose comprises an increase in single dose amount of the therapeutic agent relative to a previous dose.

18. The method according to claim 1, wherein the effective dose comprises a reduced time interval between dose administrations relative to a time interval between previous dose administrations.

* * * * *

SEQUENCE LISTING

<160> NUMBER OF SEQ ID NOS: 20

<210> SEQ ID NO 1
<211> LENGTH: 133
<212> TYPE: PRT
<213> ORGANISM: Homo sapiens

<400> SEQUENCE: 1

Ala Pro Thr Ser Ser Ser Thr Lys Lys Thr Gln Leu Gln Leu Glu His
1               5                   10                  15

Leu Leu Leu Asp Leu Gln Met Ile Leu Asn Gly Ile Asn Asn Tyr Lys
            20                  25                  30

Asn Pro Lys Leu Thr Arg Met Leu Thr Phe Lys Phe Tyr Met Pro Lys
        35                  40                  45

Lys Ala Thr Glu Leu Lys His Leu Gln Cys Leu Glu Glu Glu Leu Lys
    50                  55                  60

Pro Leu Glu Glu Val Leu Asn Leu Ala Gln Ser Lys Asn Phe His Leu
65                  70                  75                  80

Arg Pro Arg Asp Leu Ile Ser Asn Ile Asn Val Ile Val Leu Glu Leu
                85                  90                  95

Lys Gly Ser Glu Thr Thr Phe Met Cys Glu Tyr Ala Asp Glu Thr Ala
            100                 105                 110

Thr Ile Val Glu Phe Leu Asn Arg Trp Ile Thr Phe Cys Gln Ser Ile
        115                 120                 125

Ile Ser Thr Leu Thr
    130

<210> SEQ ID NO 2
<211> LENGTH: 133
<212> TYPE: PRT
<213> ORGANISM: Artificial Sequence
<220> FEATURE:
<223> OTHER INFORMATION: IL2v

<400> SEQUENCE: 2

Ala Pro Ala Ser Ser Ser Thr Lys Lys Thr Gln Leu Gln Leu Glu His
1               5                   10                  15

Leu Leu Leu Asp Leu Gln Met Ile Leu Asn Gly Ile Asn Asn Tyr Lys
            20                  25                  30

Asn Pro Lys Leu Thr Arg Met Leu Thr Ala Lys Phe Ala Met Pro Lys
        35                  40                  45

Lys Ala Thr Glu Leu Lys His Leu Gln Cys Leu Glu Glu Glu Leu Lys
    50                  55                  60

Pro Leu Glu Glu Val Leu Asn Gly Ala Gln Ser Lys Asn Phe His Leu
65                  70                  75                  80

Arg Pro Arg Asp Leu Ile Ser Asn Ile Asn Val Ile Val Leu Glu Leu
                85                  90                  95

Lys Gly Ser Glu Thr Thr Phe Met Cys Glu Tyr Ala Asp Glu Thr Ala
            100                 105                 110

Thr Ile Val Glu Phe Leu Asn Arg Trp Ile Thr Phe Ala Gln Ser Ile
        115                 120                 125

Ile Ser Thr Leu Thr
    130

<210> SEQ ID NO 3
<211> LENGTH: 5
<212> TYPE: PRT
<213> ORGANISM: Artificial Sequence

```
<220> FEATURE:
<223> OTHER INFORMATION: CEA HCDR1

<400> SEQUENCE: 3

Glu Phe Gly Met Asn
1               5

<210> SEQ ID NO 4
<211> LENGTH: 17
<212> TYPE: PRT
<213> ORGANISM: Artificial Sequence
<220> FEATURE:
<223> OTHER INFORMATION: CEA HCDR2

<400> SEQUENCE: 4

Trp Ile Asn Thr Lys Thr Gly Glu Ala Thr Tyr Val Glu Glu Phe Lys
1               5                   10                  15

Gly

<210> SEQ ID NO 5
<211> LENGTH: 12
<212> TYPE: PRT
<213> ORGANISM: Artificial Sequence
<220> FEATURE:
<223> OTHER INFORMATION: CEA HCDR3

<400> SEQUENCE: 5

Trp Asp Phe Ala Tyr Tyr Val Glu Ala Met Asp Tyr
1               5                   10

<210> SEQ ID NO 6
<211> LENGTH: 11
<212> TYPE: PRT
<213> ORGANISM: Artificial Sequence
<220> FEATURE:
<223> OTHER INFORMATION: CEA LCDR1

<400> SEQUENCE: 6

Lys Ala Ser Ala Ala Val Gly Thr Tyr Val Ala
1               5                   10

<210> SEQ ID NO 7
<211> LENGTH: 7
<212> TYPE: PRT
<213> ORGANISM: Artificial Sequence
<220> FEATURE:
<223> OTHER INFORMATION: CEA LCDR2

<400> SEQUENCE: 7

Ser Ala Ser Tyr Arg Lys Arg
1               5

<210> SEQ ID NO 8
<211> LENGTH: 10
<212> TYPE: PRT
<213> ORGANISM: Artificial Sequence
<220> FEATURE:
<223> OTHER INFORMATION: CEA LCDR3

<400> SEQUENCE: 8

His Gln Tyr Tyr Thr Tyr Pro Leu Phe Thr
1               5                   10

<210> SEQ ID NO 9
<211> LENGTH: 121
<212> TYPE: PRT
```

<213> ORGANISM: Artificial Sequence
<220> FEATURE:
<223> OTHER INFORMATION: CEA VH

<400> SEQUENCE: 9

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Glu Phe
            20                  25                  30

Gly Met Asn Trp Val Arg Gln Ala Pro Gly Gln Gly Leu Glu Trp Met
        35                  40                  45

Gly Trp Ile Asn Thr Lys Thr Gly Glu Ala Thr Tyr Val Glu Glu Phe
    50                  55                  60

Lys Gly Arg Val Thr Phe Thr Thr Asp Thr Ser Thr Ser Thr Ala Tyr
65                  70                  75                  80

Met Glu Leu Arg Ser Leu Arg Ser Asp Asp Thr Ala Val Tyr Tyr Cys
                85                  90                  95

Ala Arg Trp Asp Phe Ala Tyr Tyr Val Glu Ala Met Asp Tyr Trp Gly
            100                 105                 110

Gln Gly Thr Thr Val Thr Val Ser Ser
        115                 120

<210> SEQ ID NO 10
<211> LENGTH: 108
<212> TYPE: PRT
<213> ORGANISM: Artificial Sequence
<220> FEATURE:
<223> OTHER INFORMATION: CEA VL

<400> SEQUENCE: 10

Asp Ile Gln Met Thr Gln Ser Pro Ser Ser Leu Ser Ala Ser Val Gly
1               5                   10                  15

Asp Arg Val Thr Ile Thr Cys Lys Ala Ser Ala Ala Val Gly Thr Tyr
            20                  25                  30

Val Ala Trp Tyr Gln Gln Lys Pro Gly Lys Ala Pro Lys Leu Leu Ile
        35                  40                  45

Tyr Ser Ala Ser Tyr Arg Lys Arg Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys His Gln Tyr Tyr Thr Tyr Pro Leu
                85                  90                  95

Phe Thr Phe Gly Gln Gly Thr Lys Leu Glu Ile Lys
            100                 105

<210> SEQ ID NO 11
<211> LENGTH: 598
<212> TYPE: PRT
<213> ORGANISM: Artificial Sequence
<220> FEATURE:
<223> OTHER INFORMATION: CEA IL2v HC

<400> SEQUENCE: 11

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Glu Phe
            20                  25                  30

Gly Met Asn Trp Val Arg Gln Ala Pro Gly Gln Gly Leu Glu Trp Met
        35                  40                  45

```
Gly Trp Ile Asn Thr Lys Thr Gly Glu Ala Thr Tyr Val Glu Glu Phe
     50                  55                  60

Lys Gly Arg Val Thr Phe Thr Thr Asp Thr Ser Thr Ser Thr Ala Tyr
 65                  70                  75                  80

Met Glu Leu Arg Ser Leu Arg Ser Asp Asp Thr Ala Val Tyr Tyr Cys
                 85                  90                  95

Ala Arg Trp Asp Phe Ala Tyr Tyr Val Glu Ala Met Asp Tyr Trp Gly
            100                 105                 110

Gln Gly Thr Thr Val Thr Val Ser Ser Ala Ser Thr Lys Gly Pro Ser
        115                 120                 125

Val Phe Pro Leu Ala Pro Ser Ser Lys Ser Thr Ser Gly Gly Thr Ala
130                 135                 140

Ala Leu Gly Cys Leu Val Lys Asp Tyr Phe Pro Glu Pro Val Thr Val
145                 150                 155                 160

Ser Trp Asn Ser Gly Ala Leu Thr Ser Gly Val His Thr Phe Pro Ala
                165                 170                 175

Val Leu Gln Ser Ser Gly Leu Tyr Ser Leu Ser Ser Val Val Thr Val
            180                 185                 190

Pro Ser Ser Ser Leu Gly Thr Gln Thr Tyr Ile Cys Asn Val Asn His
        195                 200                 205

Lys Pro Ser Asn Thr Lys Val Asp Lys Lys Val Glu Pro Lys Ser Cys
210                 215                 220

Asp Lys Thr His Thr Cys Pro Pro Cys Pro Ala Pro Glu Ala Ala Gly
225                 230                 235                 240

Gly Pro Ser Val Phe Leu Phe Pro Pro Lys Pro Lys Asp Thr Leu Met
                245                 250                 255

Ile Ser Arg Thr Pro Glu Val Thr Cys Val Val Val Asp Val Ser His
            260                 265                 270

Glu Asp Pro Glu Val Lys Phe Asn Trp Tyr Val Asp Gly Val Glu Val
        275                 280                 285

His Asn Ala Lys Thr Lys Pro Arg Glu Glu Gln Tyr Asn Ser Thr Tyr
290                 295                 300

Arg Val Val Ser Val Leu Thr Val Leu His Gln Asp Trp Leu Asn Gly
305                 310                 315                 320

Lys Glu Tyr Lys Cys Lys Val Ser Asn Lys Ala Leu Gly Ala Pro Ile
                325                 330                 335

Glu Lys Thr Ile Ser Lys Ala Lys Gly Gln Pro Arg Glu Pro Gln Val
            340                 345                 350

Tyr Thr Leu Pro Pro Cys Arg Asp Glu Leu Thr Lys Asn Gln Val Ser
        355                 360                 365

Leu Trp Cys Leu Val Lys Gly Phe Tyr Pro Ser Asp Ile Ala Val Glu
370                 375                 380

Trp Glu Ser Asn Gly Gln Pro Glu Asn Asn Tyr Lys Thr Thr Pro Pro
385                 390                 395                 400

Val Leu Asp Ser Asp Gly Ser Phe Phe Leu Tyr Ser Lys Leu Thr Val
                405                 410                 415

Asp Lys Ser Arg Trp Gln Gln Gly Asn Val Phe Ser Cys Ser Val Met
            420                 425                 430

His Glu Ala Leu His Asn His Tyr Thr Gln Lys Ser Leu Ser Leu Ser
        435                 440                 445

Pro Gly Gly Gly Gly Ser Gly Gly Gly Ser Gly Gly Gly Gly
450                 455                 460
```

```
Ser Ala Pro Ala Ser Ser Thr Lys Lys Thr Gln Leu Gln Leu Glu
465                 470                 475                 480

His Leu Leu Leu Asp Leu Gln Met Ile Leu Asn Gly Ile Asn Asn Tyr
                485                 490                 495

Lys Asn Pro Lys Leu Thr Arg Met Leu Thr Ala Lys Phe Ala Met Pro
            500                 505                 510

Lys Lys Ala Thr Glu Leu Lys His Leu Gln Cys Leu Glu Glu Glu Leu
        515                 520                 525

Lys Pro Leu Glu Glu Val Leu Asn Gly Ala Gln Ser Lys Asn Phe His
    530                 535                 540

Leu Arg Pro Arg Asp Leu Ile Ser Asn Ile Asn Val Ile Val Leu Glu
545                 550                 555                 560

Leu Lys Gly Ser Glu Thr Thr Phe Met Cys Glu Tyr Ala Asp Glu Thr
                565                 570                 575

Ala Thr Ile Val Glu Phe Leu Asn Arg Trp Ile Thr Phe Ala Gln Ser
                580                 585                 590

Ile Ile Ser Thr Leu Thr
            595

<210> SEQ ID NO 12
<211> LENGTH: 451
<212> TYPE: PRT
<213> ORGANISM: Artificial Sequence
<220> FEATURE:
<223> OTHER INFORMATION: CEA HC

<400> SEQUENCE: 12

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Glu Phe
                20                  25                  30

Gly Met Asn Trp Val Arg Gln Ala Pro Gly Gln Gly Leu Glu Trp Met
            35                  40                  45

Gly Trp Ile Asn Thr Lys Thr Gly Glu Ala Thr Tyr Val Glu Glu Phe
50                  55                  60

Lys Gly Arg Val Thr Phe Thr Thr Asp Thr Ser Thr Ser Thr Ala Tyr
65                  70                  75                  80

Met Glu Leu Arg Ser Leu Arg Ser Asp Asp Thr Ala Val Tyr Tyr Cys
                85                  90                  95

Ala Arg Trp Asp Phe Ala Tyr Tyr Val Glu Ala Met Asp Tyr Trp Gly
            100                 105                 110

Gln Gly Thr Thr Val Thr Val Ser Ser Ala Ser Thr Lys Gly Pro Ser
        115                 120                 125

Val Phe Pro Leu Ala Pro Ser Ser Lys Ser Thr Ser Gly Gly Thr Ala
    130                 135                 140

Ala Leu Gly Cys Leu Val Lys Asp Tyr Phe Pro Glu Pro Val Thr Val
145                 150                 155                 160

Ser Trp Asn Ser Gly Ala Leu Thr Ser Gly Val His Thr Phe Pro Ala
                165                 170                 175

Val Leu Gln Ser Ser Gly Leu Tyr Ser Leu Ser Ser Val Val Thr Val
            180                 185                 190

Pro Ser Ser Ser Leu Gly Thr Gln Thr Tyr Ile Cys Asn Val Asn His
        195                 200                 205

Lys Pro Ser Asn Thr Lys Val Asp Lys Lys Val Glu Pro Lys Ser Cys
    210                 215                 220
```

Asp Lys Thr His Thr Cys Pro Pro Cys Pro Ala Pro Glu Ala Ala Gly
225                 230                 235                 240

Gly Pro Ser Val Phe Leu Phe Pro Pro Lys Pro Lys Asp Thr Leu Met
            245                 250                 255

Ile Ser Arg Thr Pro Glu Val Thr Cys Val Val Val Asp Val Ser His
        260                 265                 270

Glu Asp Pro Glu Val Lys Phe Asn Trp Tyr Val Asp Gly Val Glu Val
    275                 280                 285

His Asn Ala Lys Thr Lys Pro Arg Glu Glu Gln Tyr Asn Ser Thr Tyr
290                 295                 300

Arg Val Val Ser Val Leu Thr Val Leu His Gln Asp Trp Leu Asn Gly
305                 310                 315                 320

Lys Glu Tyr Lys Cys Lys Val Ser Asn Lys Ala Leu Gly Ala Pro Ile
                325                 330                 335

Glu Lys Thr Ile Ser Lys Ala Lys Gly Gln Pro Arg Glu Pro Gln Val
            340                 345                 350

Cys Thr Leu Pro Pro Ser Arg Asp Glu Leu Thr Lys Asn Gln Val Ser
        355                 360                 365

Leu Ser Cys Ala Val Lys Gly Phe Tyr Pro Ser Asp Ile Ala Val Glu
370                 375                 380

Trp Glu Ser Asn Gly Gln Pro Glu Asn Asn Tyr Lys Thr Thr Pro Pro
385                 390                 395                 400

Val Leu Asp Ser Asp Gly Ser Phe Phe Leu Val Ser Lys Leu Thr Val
                405                 410                 415

Asp Lys Ser Arg Trp Gln Gln Gly Asn Val Phe Ser Cys Ser Val Met
            420                 425                 430

His Glu Ala Leu His Asn His Tyr Thr Gln Lys Ser Leu Ser Leu Ser
        435                 440                 445

Pro Gly Lys
        450

<210> SEQ ID NO 13
<211> LENGTH: 215
<212> TYPE: PRT
<213> ORGANISM: Artificial Sequence
<220> FEATURE:
<223> OTHER INFORMATION: CEA LC

<400> SEQUENCE: 13

Asp Ile Gln Met Thr Gln Ser Pro Ser Ser Leu Ser Ala Ser Val Gly
1               5                   10                  15

Asp Arg Val Thr Ile Thr Cys Lys Ala Ser Ala Ala Val Gly Thr Tyr
            20                  25                  30

Val Ala Trp Tyr Gln Gln Lys Pro Gly Lys Ala Pro Lys Leu Leu Ile
        35                  40                  45

Tyr Ser Ala Ser Tyr Arg Lys Arg Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys His Gln Tyr Tyr Thr Tyr Pro Leu
                85                  90                  95

Phe Thr Phe Gly Gln Gly Thr Lys Leu Glu Ile Lys Arg Thr Val Ala
            100                 105                 110

Ala Pro Ser Val Phe Ile Phe Pro Pro Ser Asp Glu Gln Leu Lys Ser
        115                 120                 125

```
Gly Thr Ala Ser Val Val Cys Leu Leu Asn Asn Phe Tyr Pro Arg Glu
    130                 135                 140

Ala Lys Val Gln Trp Lys Val Asp Asn Ala Leu Gln Ser Gly Asn Ser
145                 150                 155                 160

Gln Glu Ser Val Thr Glu Gln Asp Ser Lys Asp Ser Thr Tyr Ser Leu
                165                 170                 175

Ser Ser Thr Leu Thr Leu Ser Lys Ala Asp Tyr Glu Lys His Lys Val
            180                 185                 190

Tyr Ala Cys Glu Val Thr His Gln Gly Leu Ser Ser Pro Val Thr Lys
        195                 200                 205

Ser Phe Asn Arg Gly Glu Cys
    210                 215

<210> SEQ ID NO 14
<211> LENGTH: 117
<212> TYPE: PRT
<213> ORGANISM: Artificial Sequence
<220> FEATURE:
<223> OTHER INFORMATION: FAP VH

<400> SEQUENCE: 14

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Ala Met Ser Trp Val Arg Gln Ala Pro Gly Lys Gly Leu Glu Trp Val
        35                  40                  45

Ser Ala Ile Ile Gly Ser Gly Ala Ser Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Lys Gly Trp Phe Gly Gly Phe Asn Tyr Trp Gly Gln Gly Thr Leu
            100                 105                 110

Val Thr Val Ser Ser
        115

<210> SEQ ID NO 15
<211> LENGTH: 108
<212> TYPE: PRT
<213> ORGANISM: Artificial Sequence
<220> FEATURE:
<223> OTHER INFORMATION: FAP VL

<400> SEQUENCE: 15

Glu Ile Val Leu Thr Gln Ser Pro Gly Thr Leu Ser Leu Ser Pro Gly
1               5                   10                  15

Glu Arg Ala Thr Leu Ser Cys Arg Ala Ser Gln Ser Val Thr Ser Ser
            20                  25                  30

Tyr Leu Ala Trp Tyr Gln Gln Lys Pro Gly Gln Ala Pro Arg Leu Leu
        35                  40                  45

Ile Asn Val Gly Ser Arg Arg Ala Thr Gly Ile Pro Asp Arg Phe Ser
    50                  55                  60

Gly Ser Gly Ser Gly Thr Asp Phe Thr Leu Thr Ile Ser Arg Leu Glu
65                  70                  75                  80

Pro Glu Asp Phe Ala Val Tyr Tyr Cys Gln Gln Gly Ile Met Leu Pro
                85                  90                  95
```

-continued

```
Pro Thr Phe Gly Gln Gly Thr Lys Val Glu Ile Lys
            100                 105

<210> SEQ ID NO 16
<211> LENGTH: 594
<212> TYPE: PRT
<213> ORGANISM: Artificial Sequence
<220> FEATURE:
<223> OTHER INFORMATION: FAP IL2v HC

<400> SEQUENCE: 16

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Ala Met Ser Trp Val Arg Gln Ala Pro Gly Lys Gly Leu Glu Trp Val
        35                  40                  45

Ser Ala Ile Ile Gly Ser Gly Ala Ser Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Lys Gly Trp Phe Gly Gly Phe Asn Tyr Trp Gly Gln Gly Thr Leu
            100                 105                 110

Val Thr Val Ser Ser Ala Ser Thr Lys Gly Pro Ser Val Phe Pro Leu
        115                 120                 125

Ala Pro Ser Ser Lys Ser Thr Ser Gly Gly Thr Ala Ala Leu Gly Cys
    130                 135                 140

Leu Val Lys Asp Tyr Phe Pro Glu Pro Val Thr Val Ser Trp Asn Ser
145                 150                 155                 160

Gly Ala Leu Thr Ser Gly Val His Thr Phe Pro Ala Val Leu Gln Ser
                165                 170                 175

Ser Gly Leu Tyr Ser Leu Ser Ser Val Val Thr Val Pro Ser Ser Ser
            180                 185                 190

Leu Gly Thr Gln Thr Tyr Ile Cys Asn Val Asn His Lys Pro Ser Asn
        195                 200                 205

Thr Lys Val Asp Lys Lys Val Glu Pro Lys Ser Cys Asp Lys Thr His
    210                 215                 220

Thr Cys Pro Pro Cys Pro Ala Pro Glu Ala Ala Gly Gly Pro Ser Val
225                 230                 235                 240

Phe Leu Phe Pro Pro Lys Pro Lys Asp Thr Leu Met Ile Ser Arg Thr
                245                 250                 255

Pro Glu Val Thr Cys Val Val Val Asp Val Ser His Glu Asp Pro Glu
            260                 265                 270

Val Lys Phe Asn Trp Tyr Val Asp Gly Val Glu Val His Asn Ala Lys
        275                 280                 285

Thr Lys Pro Arg Glu Glu Gln Tyr Asn Ser Thr Tyr Arg Val Val Ser
    290                 295                 300

Val Leu Thr Val Leu His Gln Asp Trp Leu Asn Gly Lys Glu Tyr Lys
305                 310                 315                 320

Cys Lys Val Ser Asn Lys Ala Leu Gly Ala Pro Ile Glu Lys Thr Ile
                325                 330                 335

Ser Lys Ala Lys Gly Gln Pro Arg Glu Pro Gln Val Tyr Thr Leu Pro
            340                 345                 350
```

Pro Cys Arg Asp Glu Leu Thr Lys Asn Gln Val Ser Leu Trp Cys Leu
            355                 360                 365

Val Lys Gly Phe Tyr Pro Ser Asp Ile Ala Val Glu Trp Glu Ser Asn
    370                 375                 380

Gly Gln Pro Glu Asn Asn Tyr Lys Thr Thr Pro Pro Val Leu Asp Ser
385                 390                 395                 400

Asp Gly Ser Phe Phe Leu Tyr Ser Lys Leu Thr Val Asp Lys Ser Arg
                405                 410                 415

Trp Gln Gln Gly Asn Val Phe Ser Cys Ser Val Met His Glu Ala Leu
                420                 425                 430

His Asn His Tyr Thr Gln Lys Ser Leu Ser Leu Ser Pro Gly Gly Gly
            435                 440                 445

Gly Gly Ser Gly Gly Gly Ser Gly Gly Gly Ser Ala Pro Ala
            450                 455                 460

Ser Ser Ser Thr Lys Lys Thr Gln Leu Gln Leu Glu His Leu Leu Leu
465                 470                 475                 480

Asp Leu Gln Met Ile Leu Asn Gly Ile Asn Asn Tyr Lys Asn Pro Lys
                485                 490                 495

Leu Thr Arg Met Leu Thr Ala Lys Phe Ala Met Pro Lys Lys Ala Thr
            500                 505                 510

Glu Leu Lys His Leu Gln Cys Leu Glu Glu Glu Leu Lys Pro Leu Glu
            515                 520                 525

Glu Val Leu Asn Gly Ala Gln Ser Lys Asn Phe His Leu Arg Pro Arg
530                 535                 540

Asp Leu Ile Ser Asn Ile Asn Val Ile Val Leu Glu Leu Lys Gly Ser
545                 550                 555                 560

Glu Thr Thr Phe Met Cys Glu Tyr Ala Asp Glu Thr Ala Thr Ile Val
                565                 570                 575

Glu Phe Leu Asn Arg Trp Ile Thr Phe Ala Gln Ser Ile Ile Ser Thr
            580                 585                 590

Leu Thr

<210> SEQ ID NO 17
<211> LENGTH: 447
<212> TYPE: PRT
<213> ORGANISM: Artificial Sequence
<220> FEATURE:
<223> OTHER INFORMATION: FAP HC

<400> SEQUENCE: 17

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Ala Met Ser Trp Val Arg Gln Ala Pro Gly Lys Gly Leu Glu Trp Val
        35                  40                  45

Ser Ala Ile Ile Gly Ser Gly Ala Ser Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Lys Gly Trp Phe Gly Gly Phe Asn Tyr Trp Gly Gln Gly Thr Leu
            100                 105                 110

```
Val Thr Val Ser Ser Ala Ser Thr Lys Gly Pro Ser Val Phe Pro Leu
            115                 120                 125

Ala Pro Ser Ser Lys Ser Thr Ser Gly Gly Thr Ala Ala Leu Gly Cys
130                 135                 140

Leu Val Lys Asp Tyr Phe Pro Glu Pro Val Thr Val Ser Trp Asn Ser
145                 150                 155                 160

Gly Ala Leu Thr Ser Gly Val His Thr Phe Pro Ala Val Leu Gln Ser
                165                 170                 175

Ser Gly Leu Tyr Ser Leu Ser Ser Val Val Thr Val Pro Ser Ser Ser
            180                 185                 190

Leu Gly Thr Gln Thr Tyr Ile Cys Asn Val Asn His Lys Pro Ser Asn
        195                 200                 205

Thr Lys Val Asp Lys Lys Val Glu Pro Lys Ser Cys Asp Lys Thr His
    210                 215                 220

Thr Cys Pro Pro Cys Pro Ala Pro Glu Ala Ala Gly Gly Pro Ser Val
225                 230                 235                 240

Phe Leu Phe Pro Pro Lys Pro Lys Asp Thr Leu Met Ile Ser Arg Thr
                245                 250                 255

Pro Glu Val Thr Cys Val Val Val Asp Val Ser His Glu Asp Pro Glu
            260                 265                 270

Val Lys Phe Asn Trp Tyr Val Asp Gly Val Glu Val His Asn Ala Lys
        275                 280                 285

Thr Lys Pro Arg Glu Glu Gln Tyr Asn Ser Thr Tyr Arg Val Val Ser
    290                 295                 300

Val Leu Thr Val Leu His Gln Asp Trp Leu Asn Gly Lys Glu Tyr Lys
305                 310                 315                 320

Cys Lys Val Ser Asn Lys Ala Leu Gly Ala Pro Ile Glu Lys Thr Ile
                325                 330                 335

Ser Lys Ala Lys Gly Gln Pro Arg Glu Pro Gln Val Cys Thr Leu Pro
            340                 345                 350

Pro Ser Arg Asp Glu Leu Thr Lys Asn Gln Val Ser Leu Ser Cys Ala
        355                 360                 365

Val Lys Gly Phe Tyr Pro Ser Asp Ile Ala Val Glu Trp Glu Ser Asn
    370                 375                 380

Gly Gln Pro Glu Asn Asn Tyr Lys Thr Thr Pro Pro Val Leu Asp Ser
385                 390                 395                 400

Asp Gly Ser Phe Phe Leu Val Ser Lys Leu Thr Val Asp Lys Ser Arg
                405                 410                 415

Trp Gln Gln Gly Asn Val Phe Ser Cys Ser Val Met His Glu Ala Leu
            420                 425                 430

His Asn His Tyr Thr Gln Lys Ser Leu Ser Leu Ser Pro Gly Lys
        435                 440                 445

<210> SEQ ID NO 18
<211> LENGTH: 215
<212> TYPE: PRT
<213> ORGANISM: Artificial Sequence
<220> FEATURE:
<223> OTHER INFORMATION: FAP LC

<400> SEQUENCE: 18

Glu Ile Val Leu Thr Gln Ser Pro Gly Thr Leu Ser Leu Ser Pro Gly
1               5                   10                  15

Glu Arg Ala Thr Leu Ser Cys Arg Ala Ser Gln Ser Val Thr Ser Ser
            20                  25                  30
```

```
Tyr Leu Ala Trp Tyr Gln Gln Lys Pro Gly Gln Ala Pro Arg Leu Leu
         35                  40                  45

Ile Asn Val Gly Ser Arg Arg Ala Thr Gly Ile Pro Asp Arg Phe Ser
 50                  55                  60

Gly Ser Gly Ser Gly Thr Asp Phe Thr Leu Thr Ile Ser Arg Leu Glu
 65                  70                  75                  80

Pro Glu Asp Phe Ala Val Tyr Tyr Cys Gln Gln Gly Ile Met Leu Pro
                 85                  90                  95

Pro Thr Phe Gly Gln Gly Thr Lys Val Glu Ile Lys Arg Thr Val Ala
             100                 105                 110

Ala Pro Ser Val Phe Ile Phe Pro Pro Ser Asp Glu Gln Leu Lys Ser
         115                 120                 125

Gly Thr Ala Ser Val Val Cys Leu Leu Asn Asn Phe Tyr Pro Arg Glu
130                 135                 140

Ala Lys Val Gln Trp Lys Val Asp Asn Ala Leu Gln Ser Gly Asn Ser
145                 150                 155                 160

Gln Glu Ser Val Thr Glu Gln Asp Ser Lys Asp Ser Thr Tyr Ser Leu
                165                 170                 175

Ser Ser Thr Leu Thr Leu Ser Lys Ala Asp Tyr Glu Lys His Lys Val
            180                 185                 190

Tyr Ala Cys Glu Val Thr His Gln Gly Leu Ser Ser Pro Val Thr Lys
        195                 200                 205

Ser Phe Asn Arg Gly Glu Cys
        210                 215

<210> SEQ ID NO 19
<211> LENGTH: 225
<212> TYPE: PRT
<213> ORGANISM: Homo sapiens

<400> SEQUENCE: 19

Asp Lys Thr His Thr Cys Pro Pro Cys Pro Ala Pro Glu Leu Leu Gly
  1               5                  10                  15

Gly Pro Ser Val Phe Leu Phe Pro Pro Lys Pro Lys Asp Thr Leu Met
             20                  25                  30

Ile Ser Arg Thr Pro Glu Val Thr Cys Val Val Val Asp Val Ser His
         35                  40                  45

Glu Asp Pro Glu Val Lys Phe Asn Trp Tyr Val Asp Gly Val Glu Val
 50                  55                  60

His Asn Ala Lys Thr Lys Pro Arg Glu Glu Gln Tyr Asn Ser Thr Tyr
 65                  70                  75                  80

Arg Val Val Ser Val Leu Thr Val Leu His Gln Asp Trp Leu Asn Gly
                 85                  90                  95

Lys Glu Tyr Lys Cys Lys Val Ser Asn Lys Ala Leu Pro Ala Pro Ile
            100                 105                 110

Glu Lys Thr Ile Ser Lys Ala Lys Gly Gln Pro Arg Glu Pro Gln Val
        115                 120                 125

Tyr Thr Leu Pro Pro Ser Arg Asp Glu Leu Thr Lys Asn Gln Val Ser
130                 135                 140

Leu Thr Cys Leu Val Lys Gly Phe Tyr Pro Ser Asp Ile Ala Val Glu
145                 150                 155                 160

Trp Glu Ser Asn Gly Gln Pro Glu Asn Asn Tyr Lys Thr Thr Pro Pro
                165                 170                 175

Val Leu Asp Ser Asp Gly Ser Phe Phe Leu Tyr Ser Lys Leu Thr Val
            180                 185                 190
```

```
Asp Lys Ser Arg Trp Gln Gln Gly Asn Val Phe Ser Cys Ser Val Met
        195                 200                 205

His Glu Ala Leu His Asn His Tyr Thr Gln Lys Ser Leu Ser Leu Ser
        210                 215                 220

Pro
225

<210> SEQ ID NO 20
<211> LENGTH: 20
<212> TYPE: PRT
<213> ORGANISM: Artificial Sequence
<220> FEATURE:
<223> OTHER INFORMATION: leader sequence

<400> SEQUENCE: 20

Met Tyr Arg Met Gln Leu Leu Ser Cys Ile Ala Leu Ser Leu Ala Leu
1               5                   10                  15

Val Thr Asn Ser
            20
```